United States Patent
Jang et al.

(10) Patent No.: US 11,639,383 B2
(45) Date of Patent: May 2, 2023

(54) PHARMACEUTICAL COMPOSITION FOR TREATMENT OF CANCER, COMPRISING AN IMMUNE CHECKPOINT INHIBITOR ANTIBODY AND A FUSION PROTEIN COMPRISING AN IL-2 MUTANT AND A CD80 EXTRACELLULAR DOMAIN

(71) Applicant: GI INNOVATION, INC., Seoul (KR)

(72) Inventors: Myoung Ho Jang, Seoul (KR); Su Youn Nam, Seoul (KR); Young Jun Koh, Seoul (KR); Young-Gyu Cho, Daejeon (KR)

(73) Assignee: GI INNOVATION, INC., Seoul (KR)

( * ) Notice: Subject to any disclaimer, the term of this patent is extended or adjusted under 35 U.S.C. 154(b) by 0 days.

(21) Appl. No.: 17/780,364

(22) PCT Filed: Nov. 27, 2020

(86) PCT No.: PCT/KR2020/017097
§ 371 (c)(1),
(2) Date: May 26, 2022

(87) PCT Pub. No.: WO2021/107689
PCT Pub. Date: Jun. 3, 2021

(65) Prior Publication Data
US 2022/0403019 A1  Dec. 22, 2022

(30) Foreign Application Priority Data

Nov. 27, 2019  (KR) .................. 10-2019-0154632

(51) Int. Cl.
| | |
|---|---|
| C07K 16/24 | (2006.01) |
| A61P 35/00 | (2006.01) |
| C07K 16/28 | (2006.01) |
| C07K 16/30 | (2006.01) |
| A61K 39/00 | (2006.01) |
| A61K 47/64 | (2017.01) |

(52) U.S. Cl.
CPC .......... *C07K 16/249* (2013.01); *A61K 47/64* (2017.08); *A61P 35/00* (2018.01); *C07K 16/2803* (2013.01); *C07K 16/2818* (2013.01); *C07K 16/30* (2013.01); *A61K 2039/507* (2013.01)

(58) Field of Classification Search
None
See application file for complete search history.

(56) References Cited

U.S. PATENT DOCUMENTS

| 2017/0216402 A1 | 8/2017 | Wittrup et al. |
| 2019/0136186 A1 | 5/2019 | Germeroth et al. |

FOREIGN PATENT DOCUMENTS

| JP | 2017-524713 A | 8/2017 |
| KR | 10-2018-0100110 A | 9/2018 |
| KR | 10-2019-0032355 A | 3/2019 |
| WO | 2016/025642 A1 | 2/2016 |

OTHER PUBLICATIONS

Jae Chan Park et al., "3190—GI 101, a novel triple-targeting bispecific CD80-IgG4-IL2variant fusion protein, elicits synergistic anti-tumor effects in preclinical models", OncologyPROMeeting resourcesESMO 2019 Congress, Sep. 30, 2019, 4 pgs.
Jae Chan Park et al., "GI-101, a novel bispecific CD80-IgG4-IL2 variant fusion protein, elicits robust anti-tumor effects in preclinical models", ESMO Congress, Sep. 27, 2019, 1 pg.
Lucas Chan et al., "IL-2/B7.1 (CD80) Fusagene Transduction of AML Blasts by a Self-Inactivating Lentiviral Vector Stimulates T Cell Responses in Vitro: a Strategy to Generate Whole Cell Vaccines for AML", Molecular Therapy, Jan. 2005, pp. 120-131, vol. 11, No. 1.
Yoon-Mi Kim, "GI-101, which showed potential for new immunotherapy, will be confirmed in clinical trials next year" Oct. 18, 2020, 5 pgs.
International Search Report for PCT/KR2020/017097 dated, Mar. 10, 2021 (PCT/ISA/210).
"GI-101 showing the possibility of new immuno-cancer drugs, clinical confirmation next year", Oct. 28, 2019, pp. 1-3, <https://www.docdocdoc.co.kr/news/articleView.html?idxno=1073307, last edited Aug. 27, 2021 >, with full English translation.
Korean Patent Office, Notice of Allowance dated May 2, 2022 in counterpart Korean Application No. 10-2020-0162168 with verified English translation, and English translation of allowed claims.
Korean Patent Office, Request for the Submission of an Opinion dated Feb. 3, 2022 in counterpart Korean Application No. 10-2020-0162168 with Patentscope—provided English translation.

*Primary Examiner* — Elly-Gerald Stoica
(74) *Attorney, Agent, or Firm* — Sughrue Mion, PLLC

(57) ABSTRACT

There is provided a pharmaceutical composition for preventing or treating cancer comprising, as active ingredients, a fusion protein dimer comprising an IL-2 protein or a variant thereof and a CD80 protein or a fragment thereof, and an immune checkpoint inhibitor. The fusion protein containing an CD80 fragment, an Fc domain of an immunoglobulin, and an IL-2 variant in an embodiment can activate immune cells such as natural killer cells as well as control the immune cell regulatory activity of regulatory T cells. In addition, the combined administration of the fusion protein and an immune checkpoint inhibitor such as Keytruda known as a PD-1 inhibitor can effectively inhibit cancer. Therefore, a pharmaceutical composition containing, as active ingredients, a fusion protein dimer comprising an IL-2 protein or a variant thereof and a CD80 protein or a fragment thereof, and an immune checkpoint inhibitor can be effectively applied to the treatment of cancer and has high industrial applicability.

5 Claims, 52 Drawing Sheets
Specification includes a Sequence Listing.

[Fig. 1]
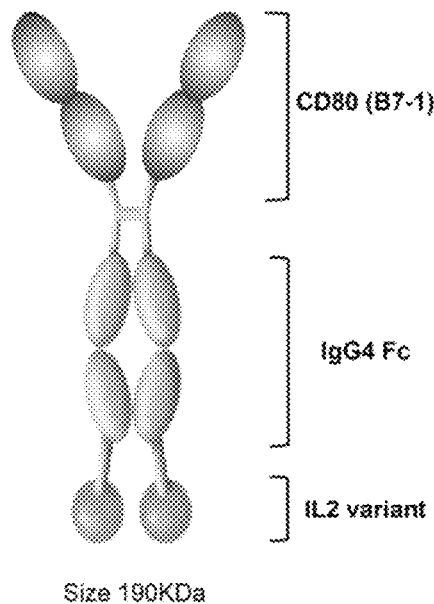
[Fig. 2]
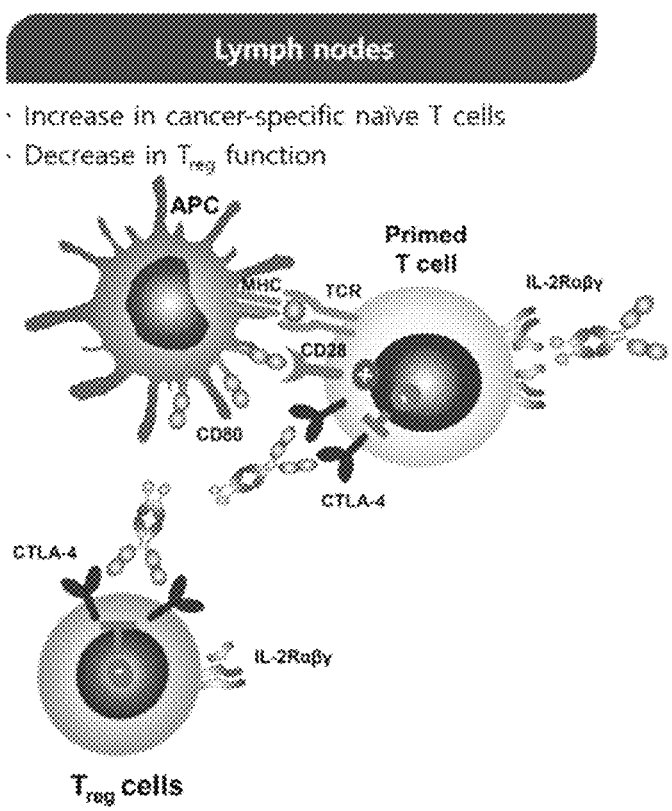

[Fig. 3]
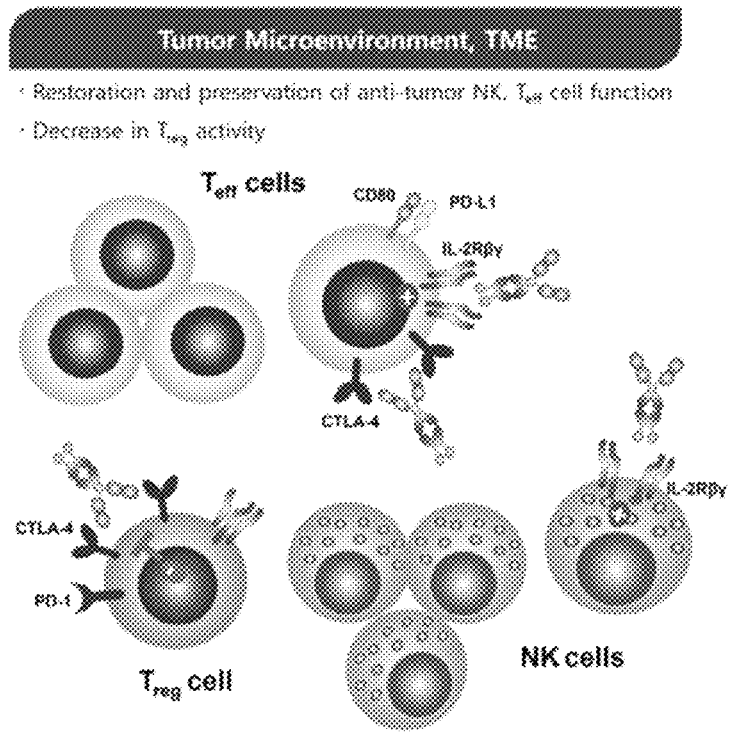
[Fig. 4]
GI101 
GI101C1 
GI101C2 
Mouse version
mGI101
Mouse version
mGI101C1

[Fig. 5]
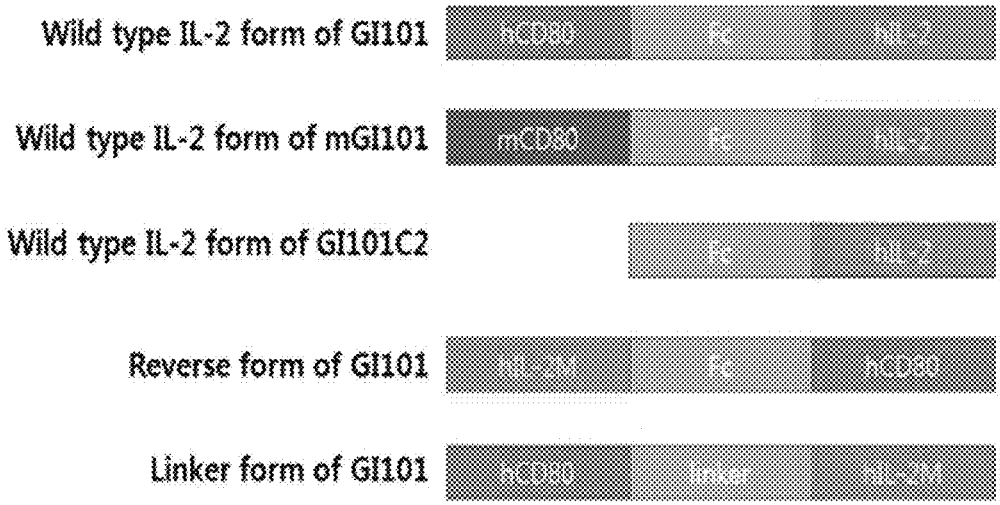
[Fig. 6]
SDS-PAGE
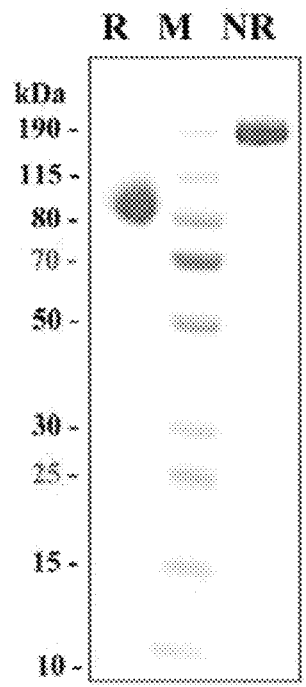

[Fig. 7]
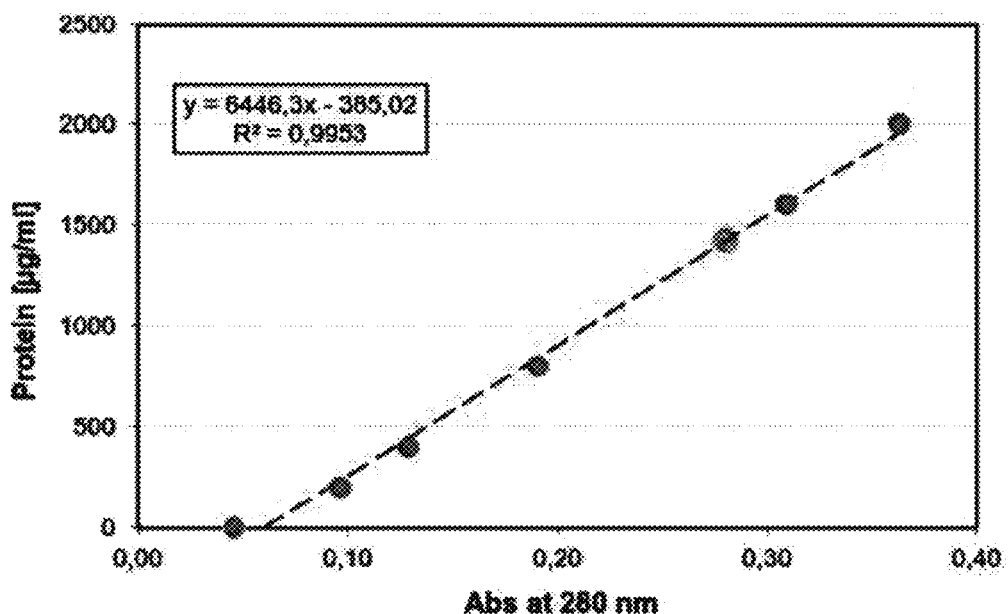
[Fig. 8]
Anlytical size exclusion chromatography (SEC)
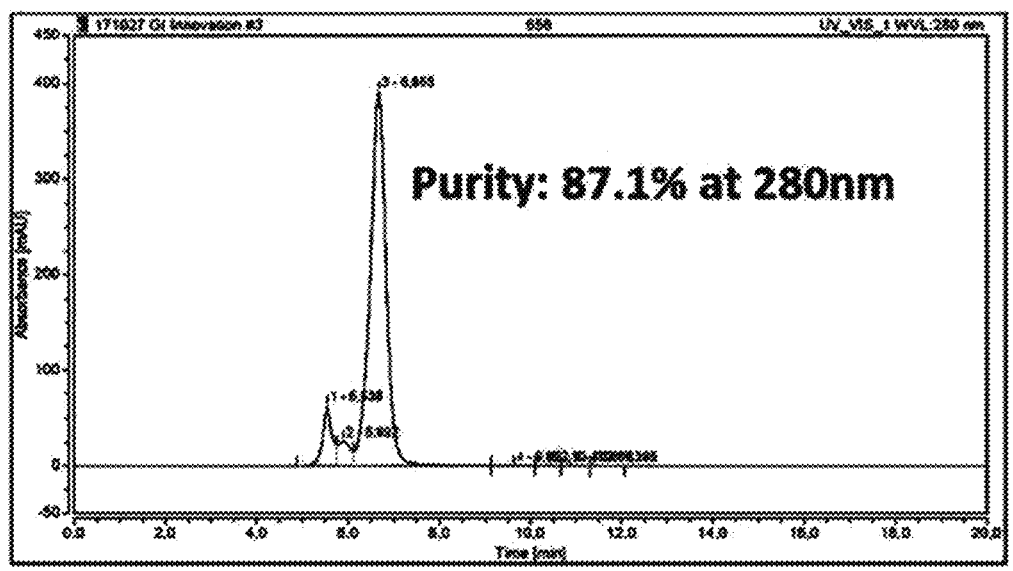

[Fig. 9]
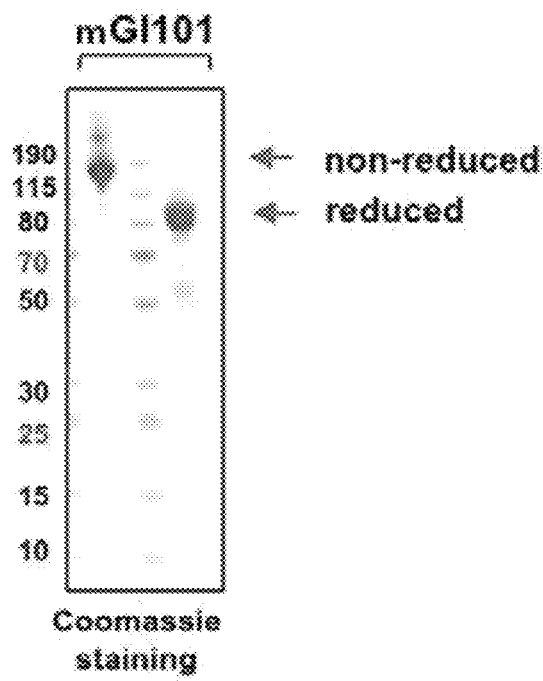
[Fig. 10]
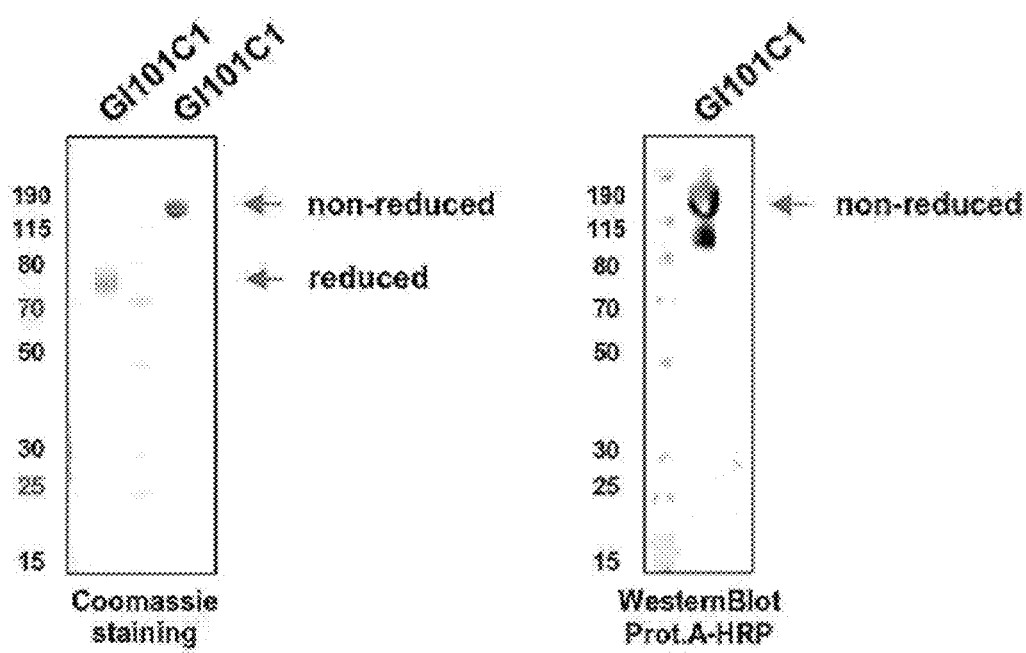

[Fig. 11]
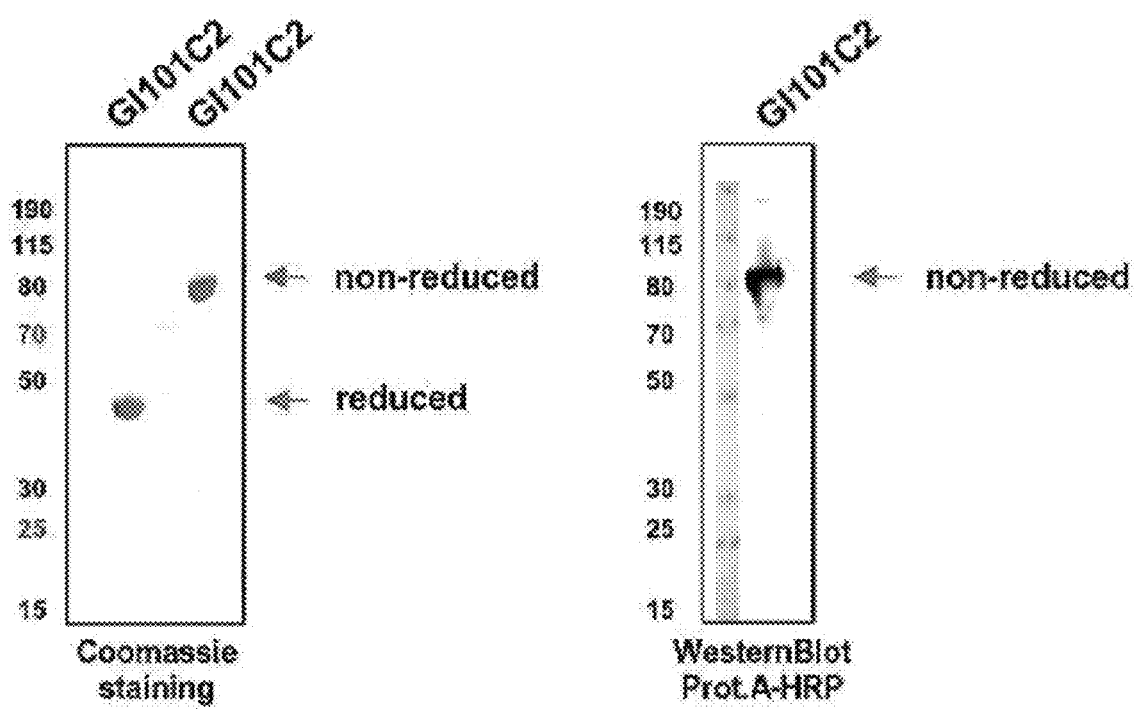
[Fig. 12]
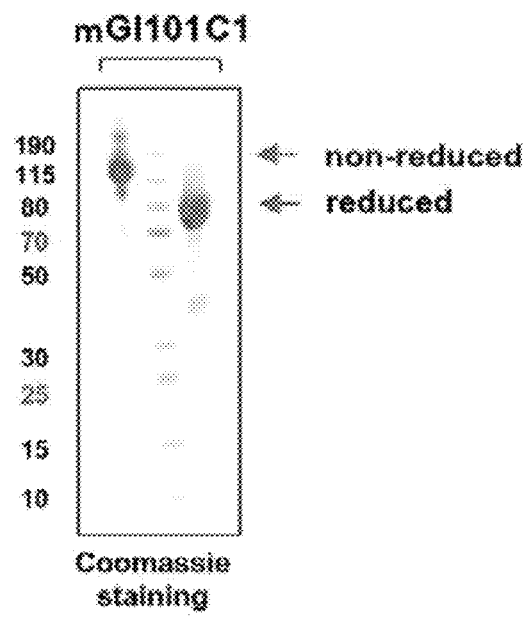

[Fig. 13]
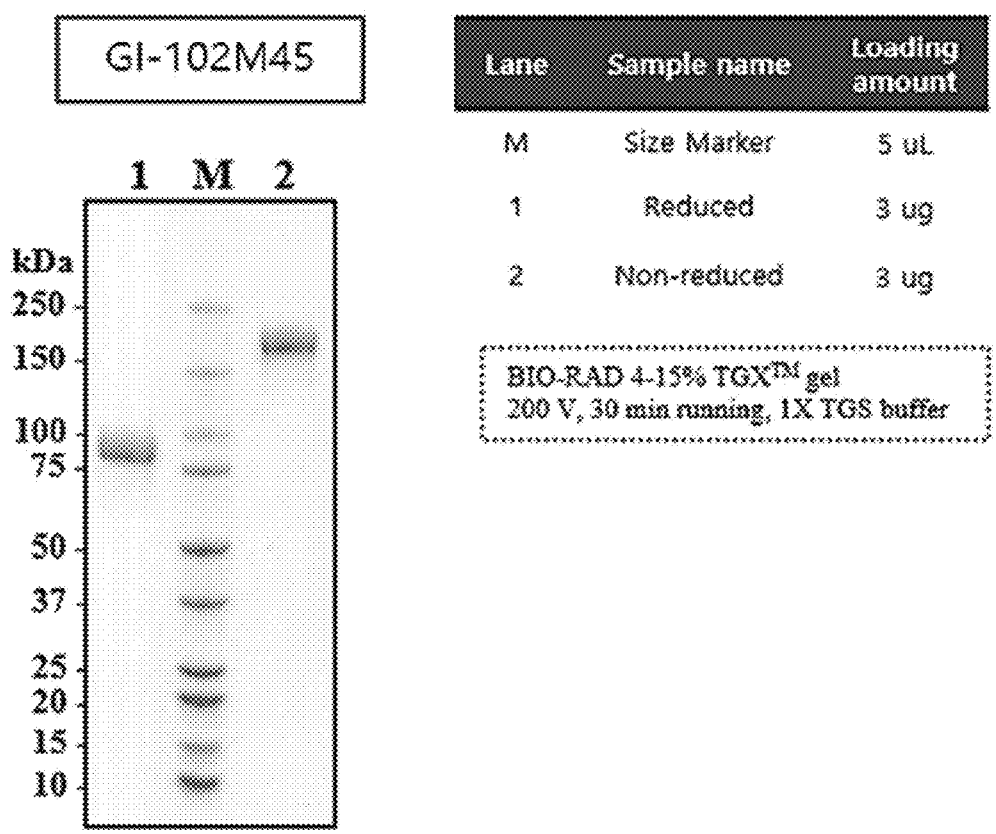

[Fig. 14]
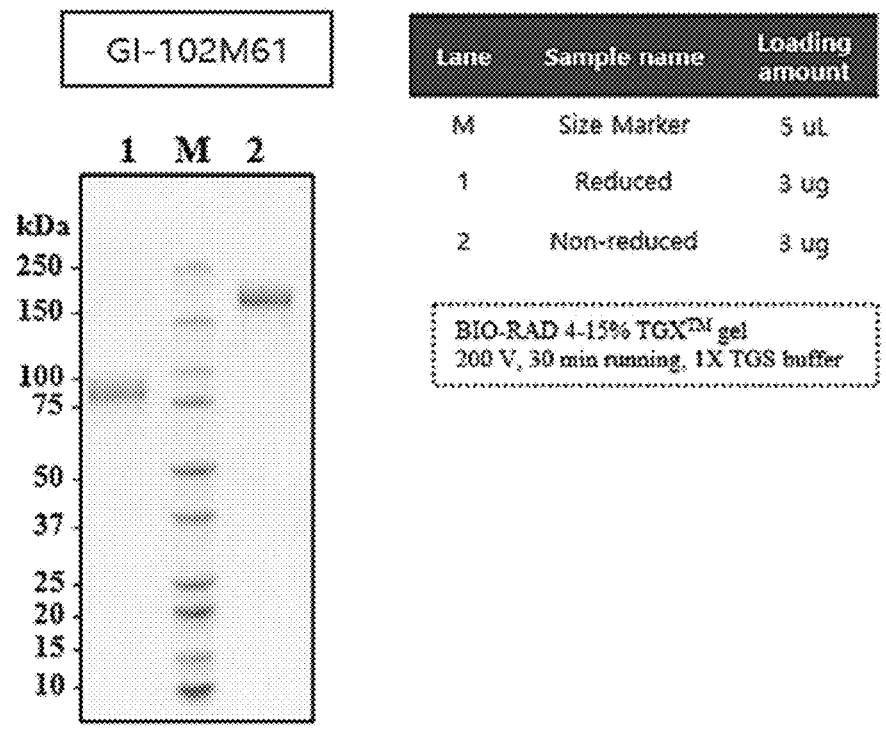
[Fig. 15]
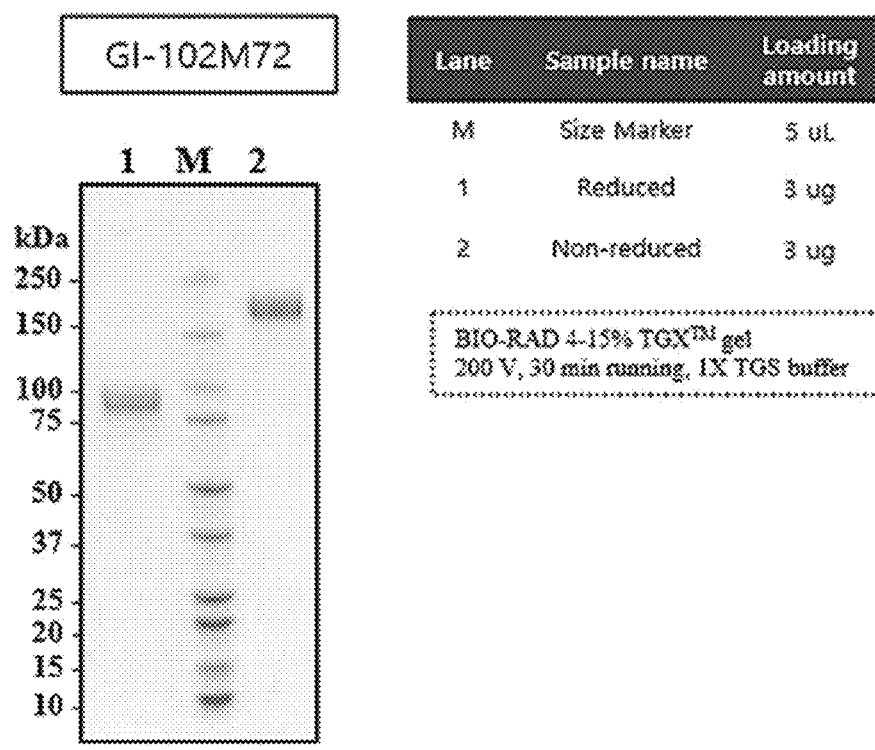

[Fig. 16]
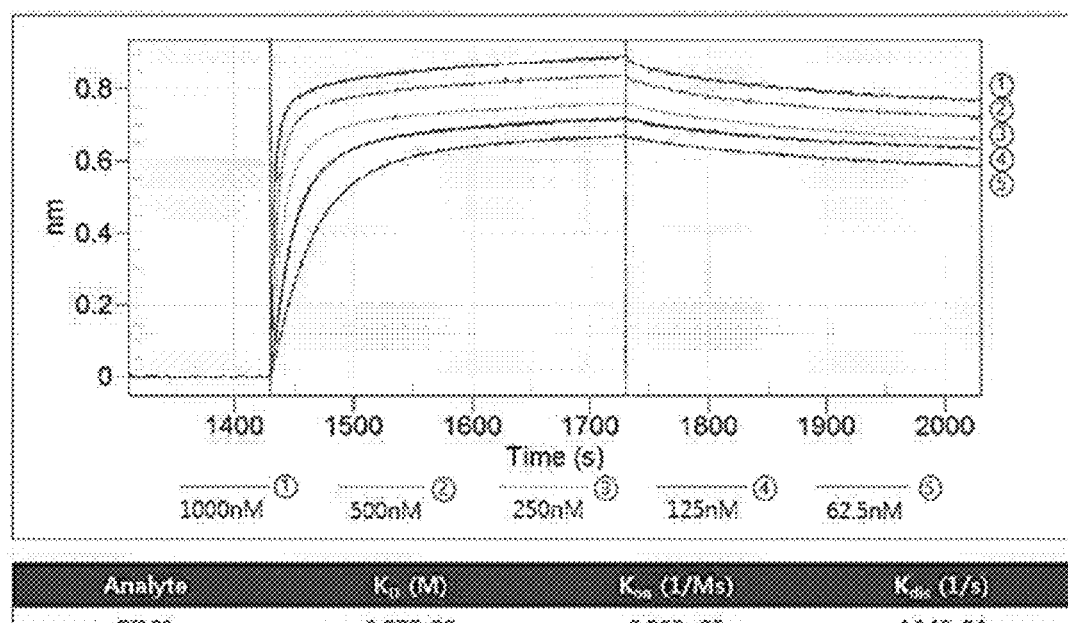
[Fig. 17]
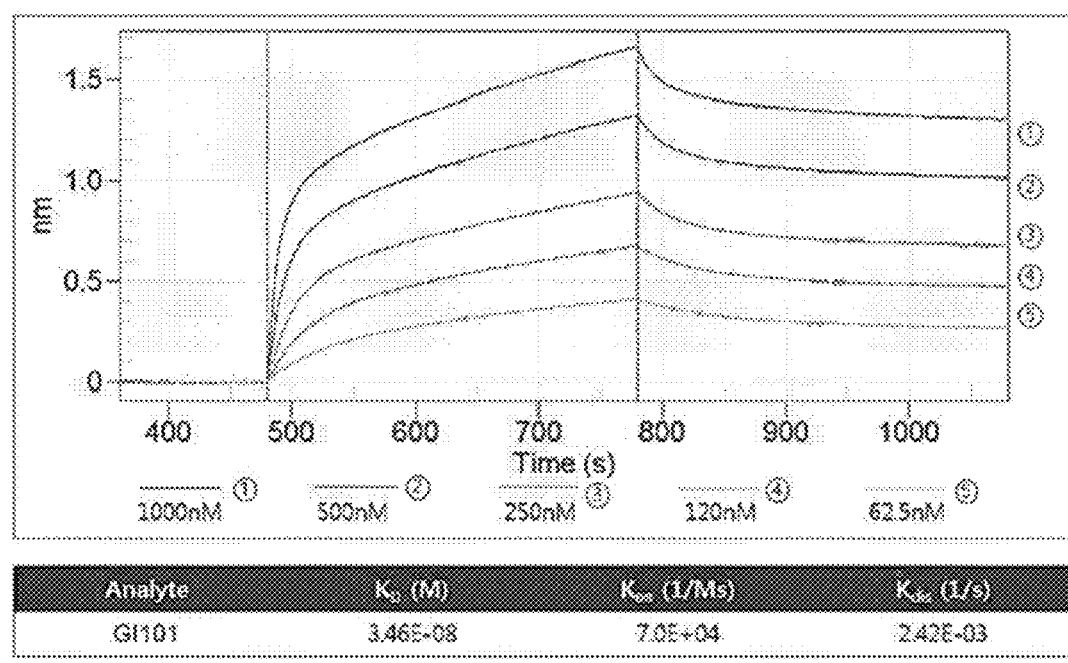

[Fig. 18]
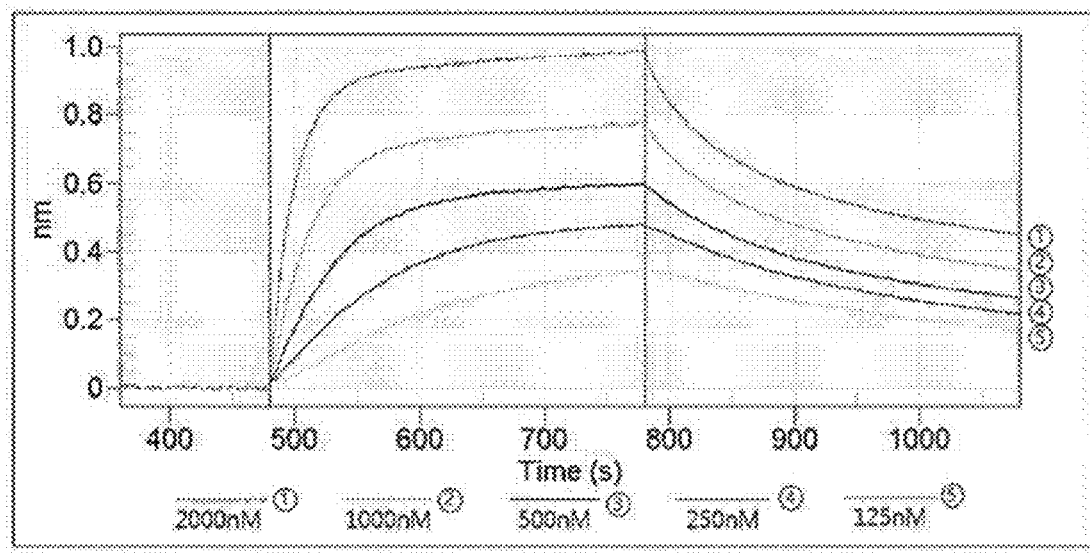
[Fig. 19]
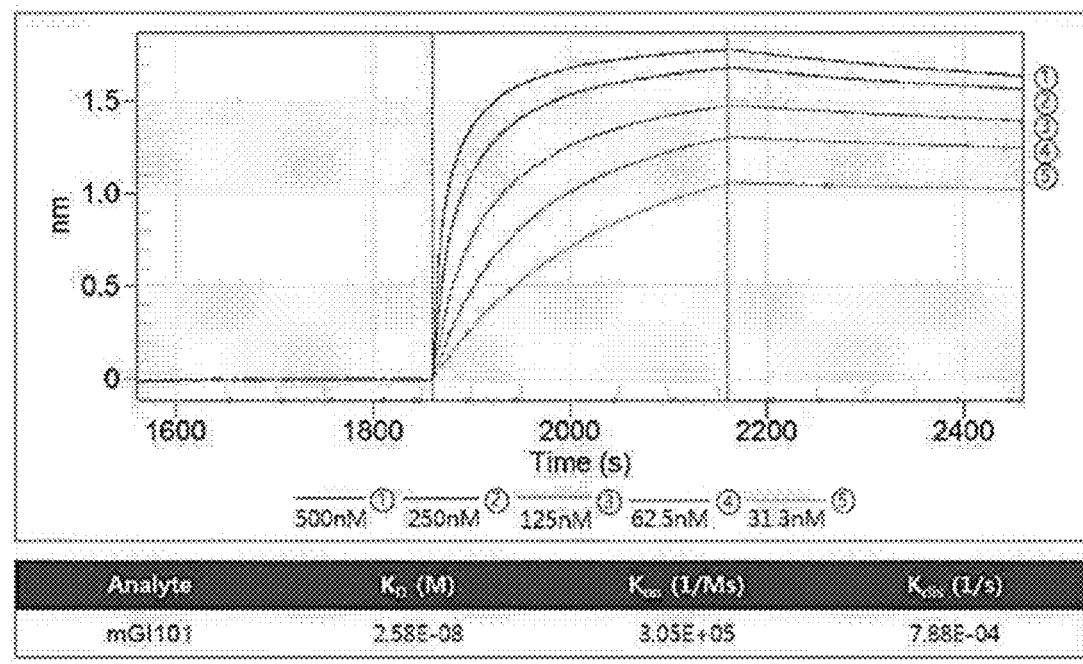

[Fig. 20]
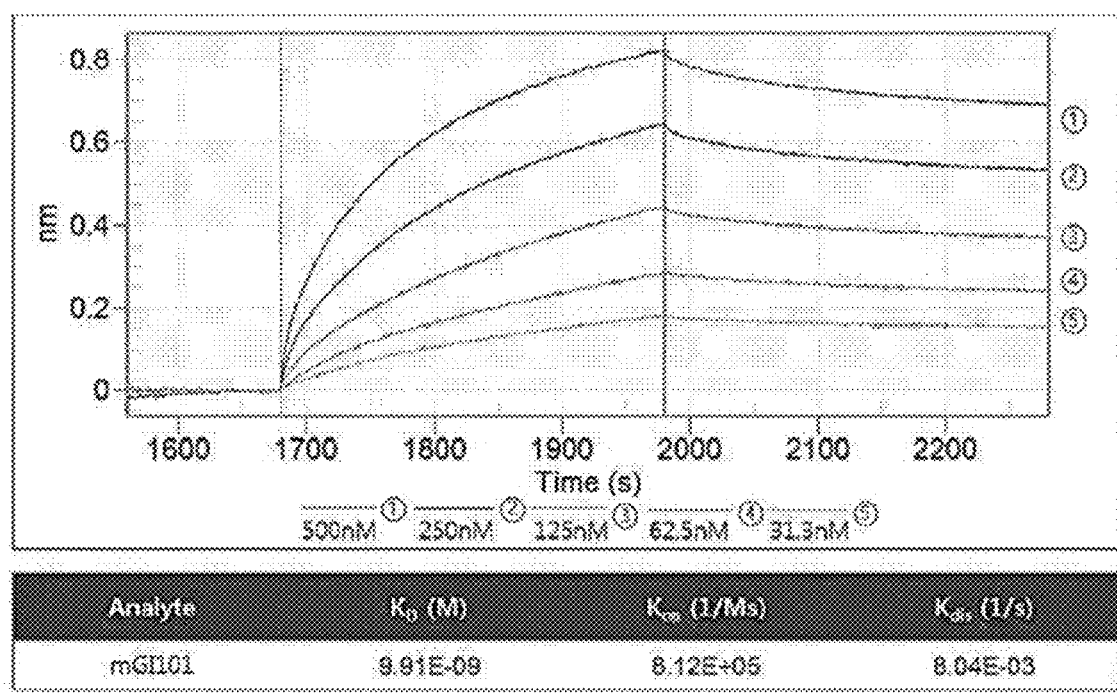

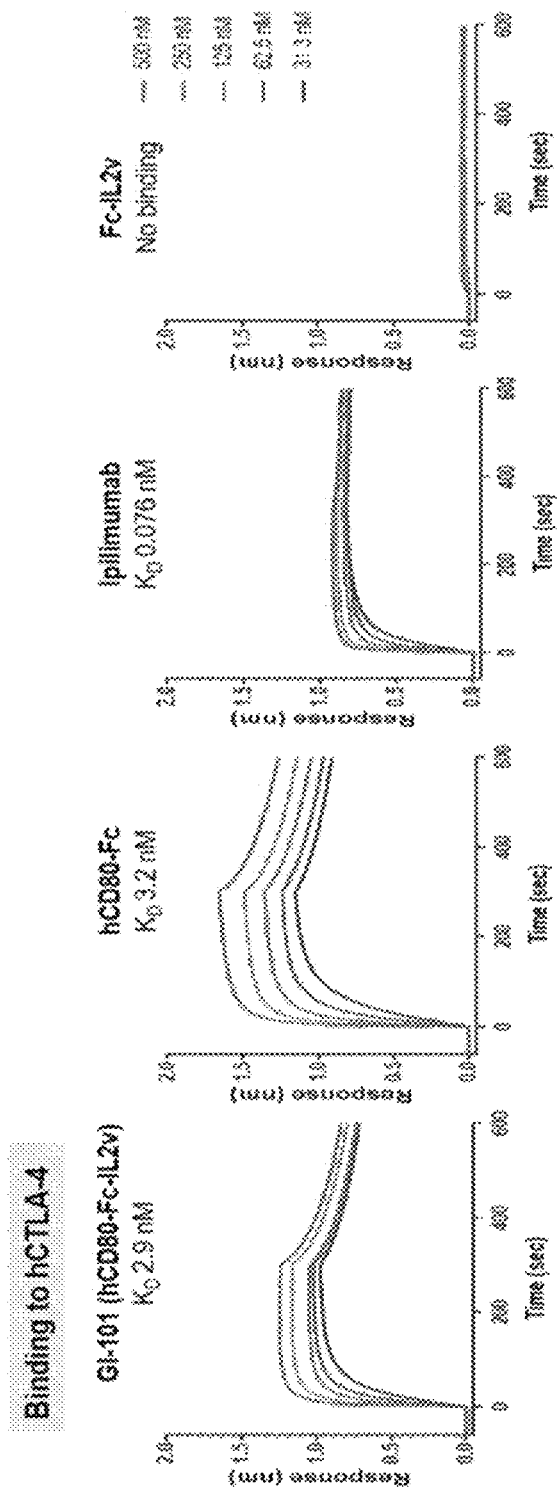

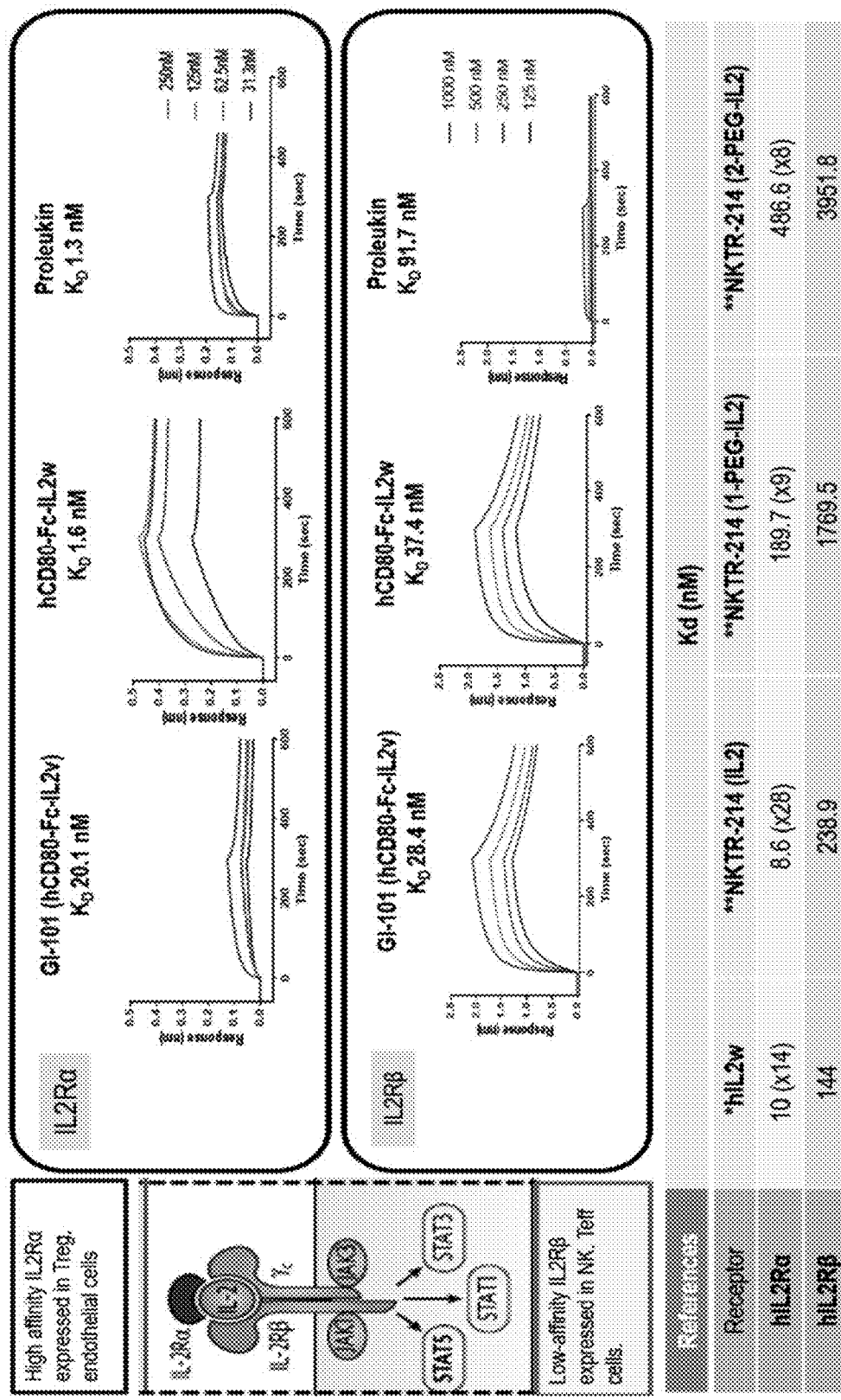
[Fig. 22]

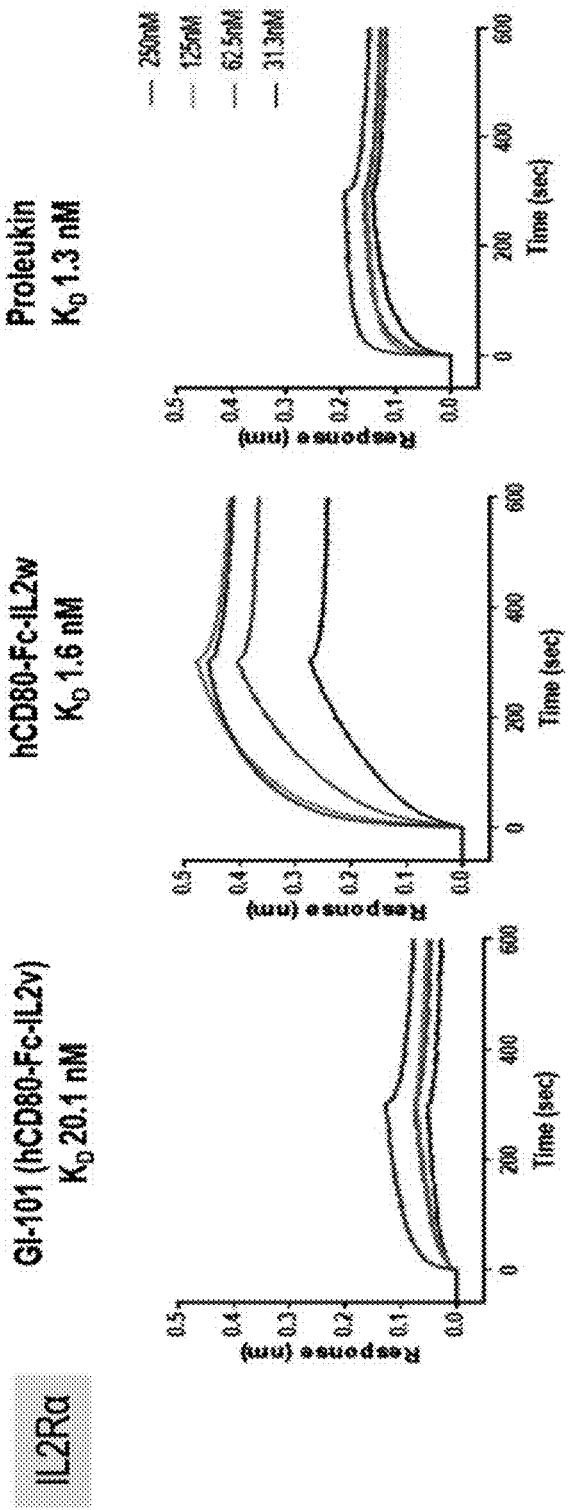

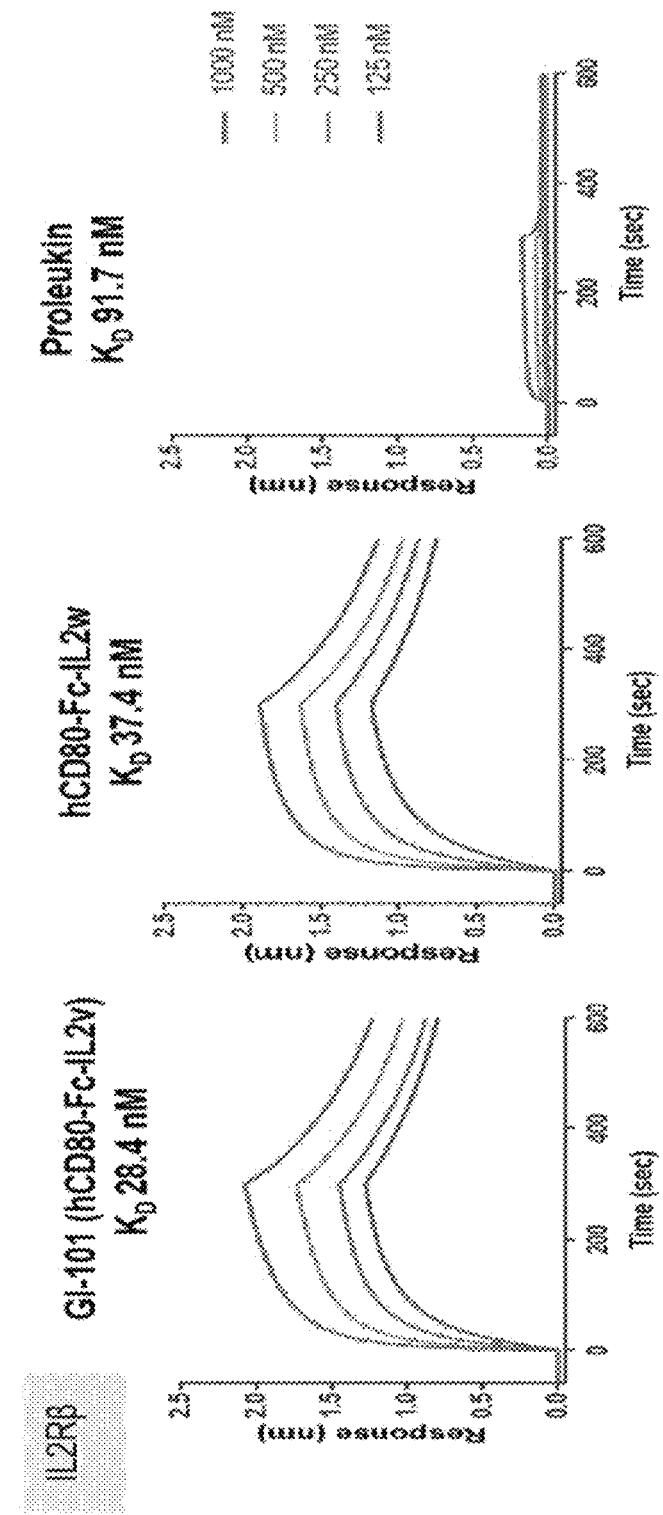
[Fig. 24]

[Fig. 25]
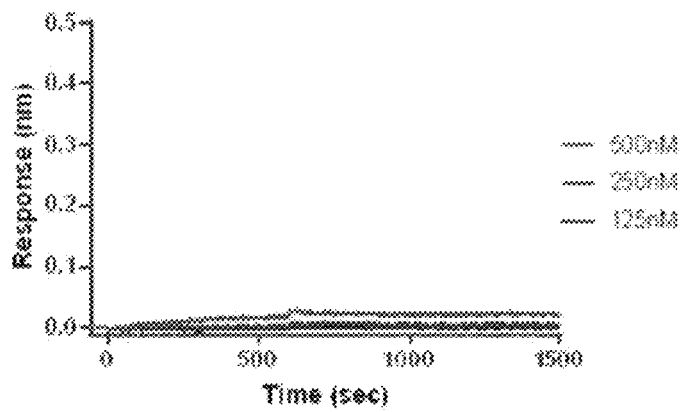
[Fig. 26]
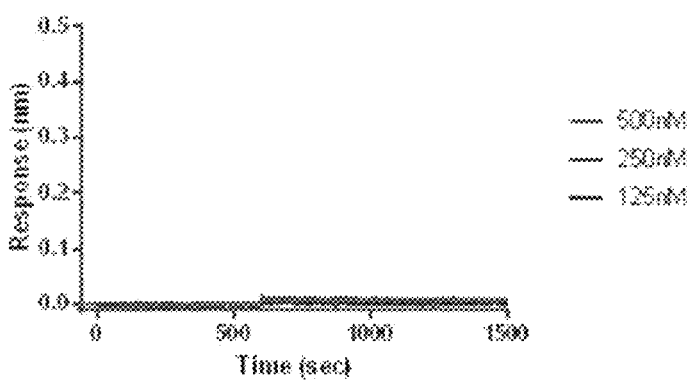
[Fig. 27]
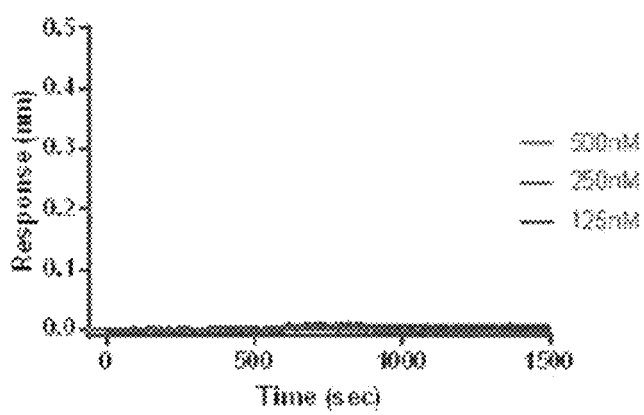

[Fig. 28]
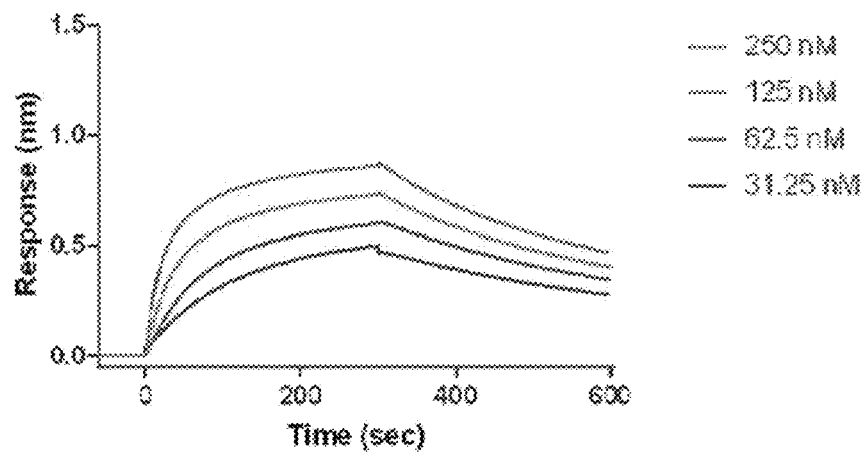
| Kon | Koff | Kd |
|---|---|---|
| 1.30X105 | 2.01X10-3 | 1.55X10-8 |
[Fig. 29]
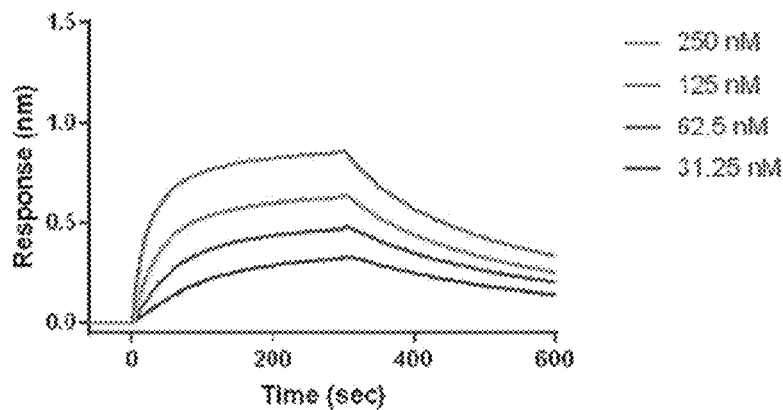
| Kon | Koff | Kd |
|---|---|---|
| 1.32X105 | 3.11X10-3 | 2.36X10-8 |

[Fig. 30]
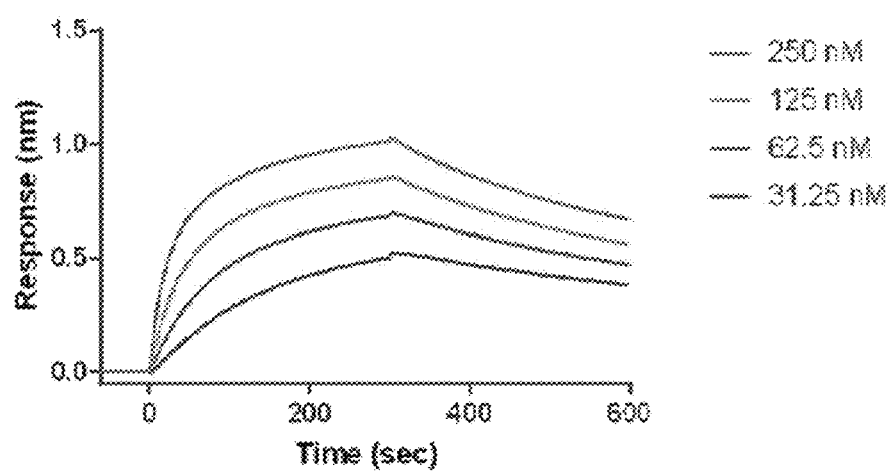
| Kon | Koff | Kd |
|---|---|---|
| 1.10X105 | 1.27X10-3 | 1.15X10-8 |

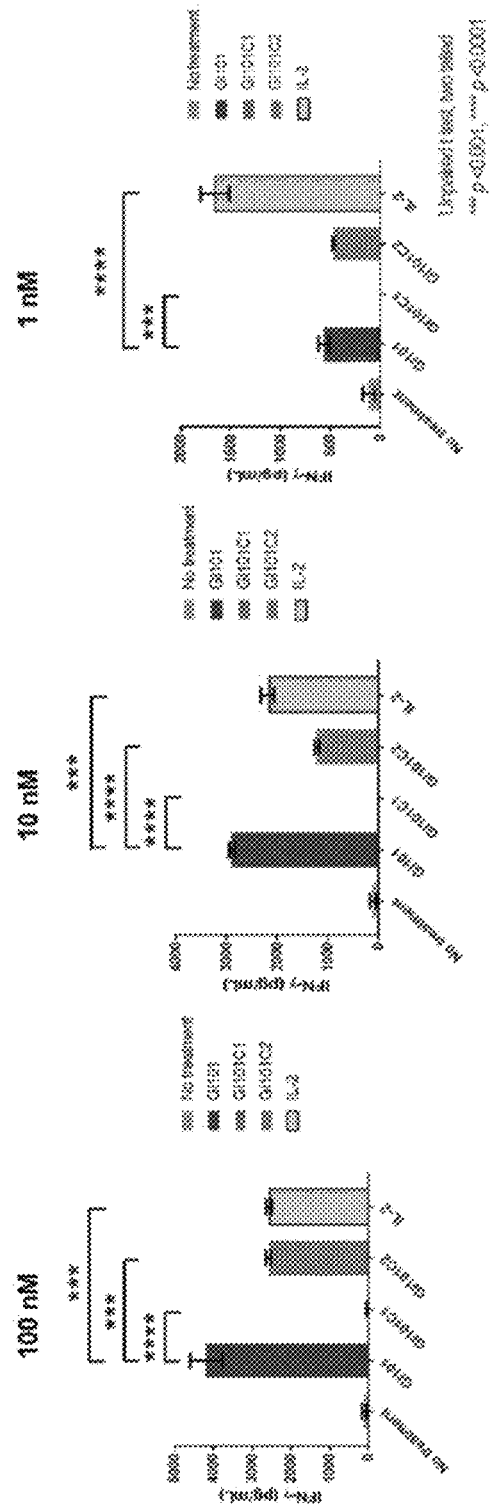

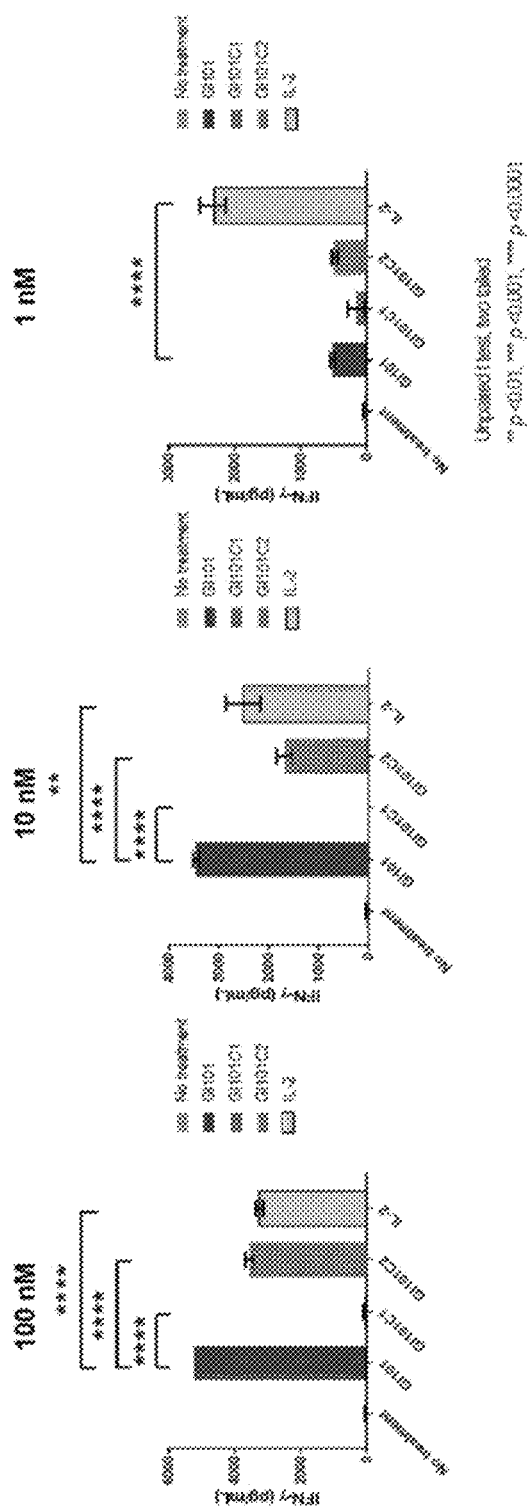

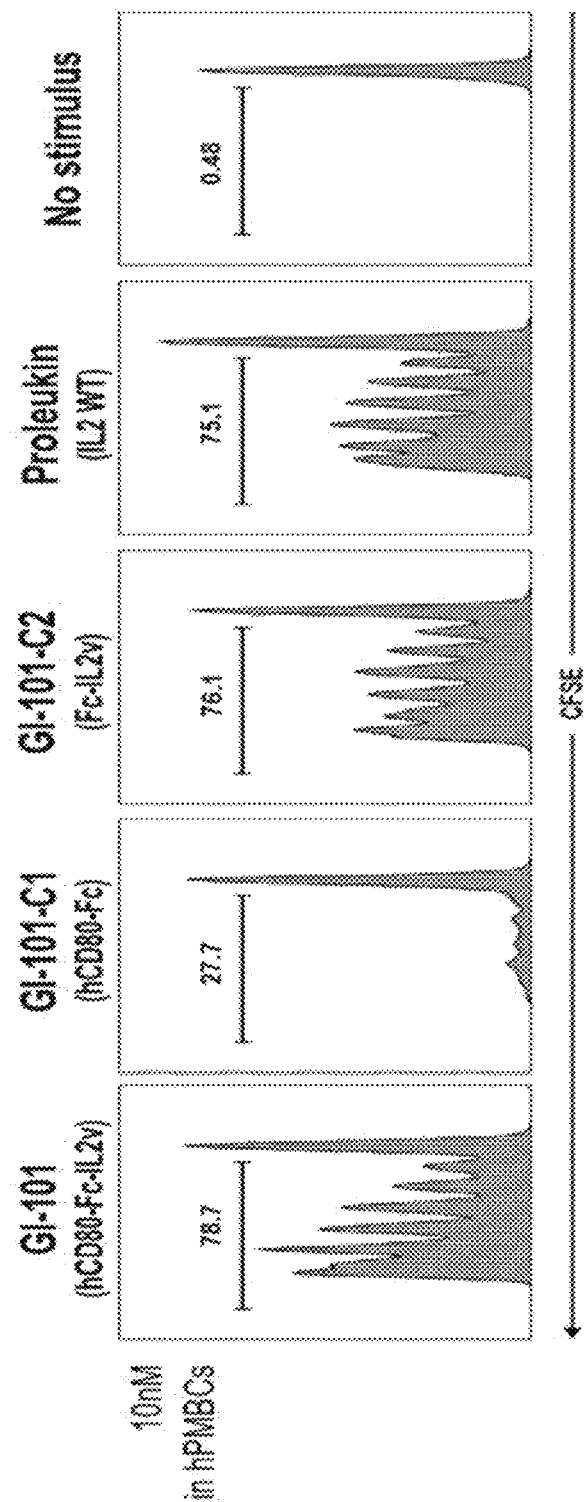

[Fig. 34]
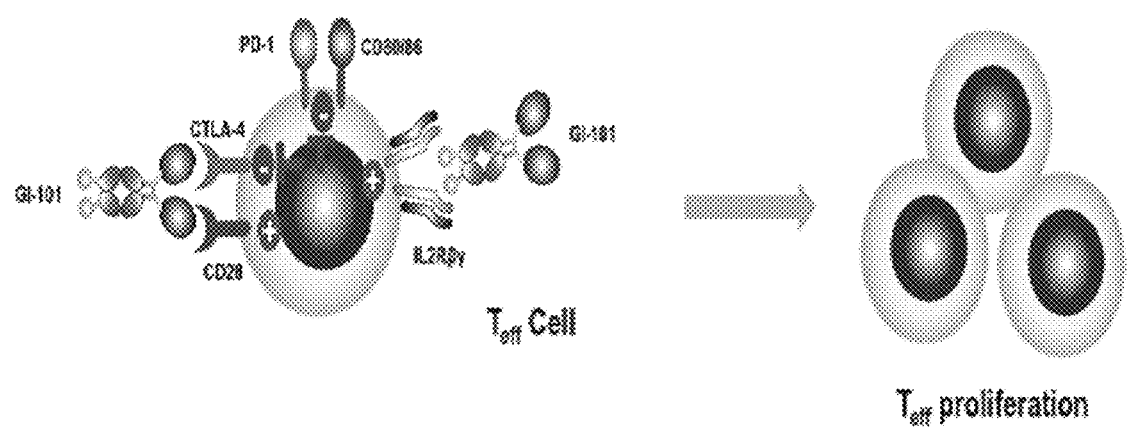
T_eff proliferation

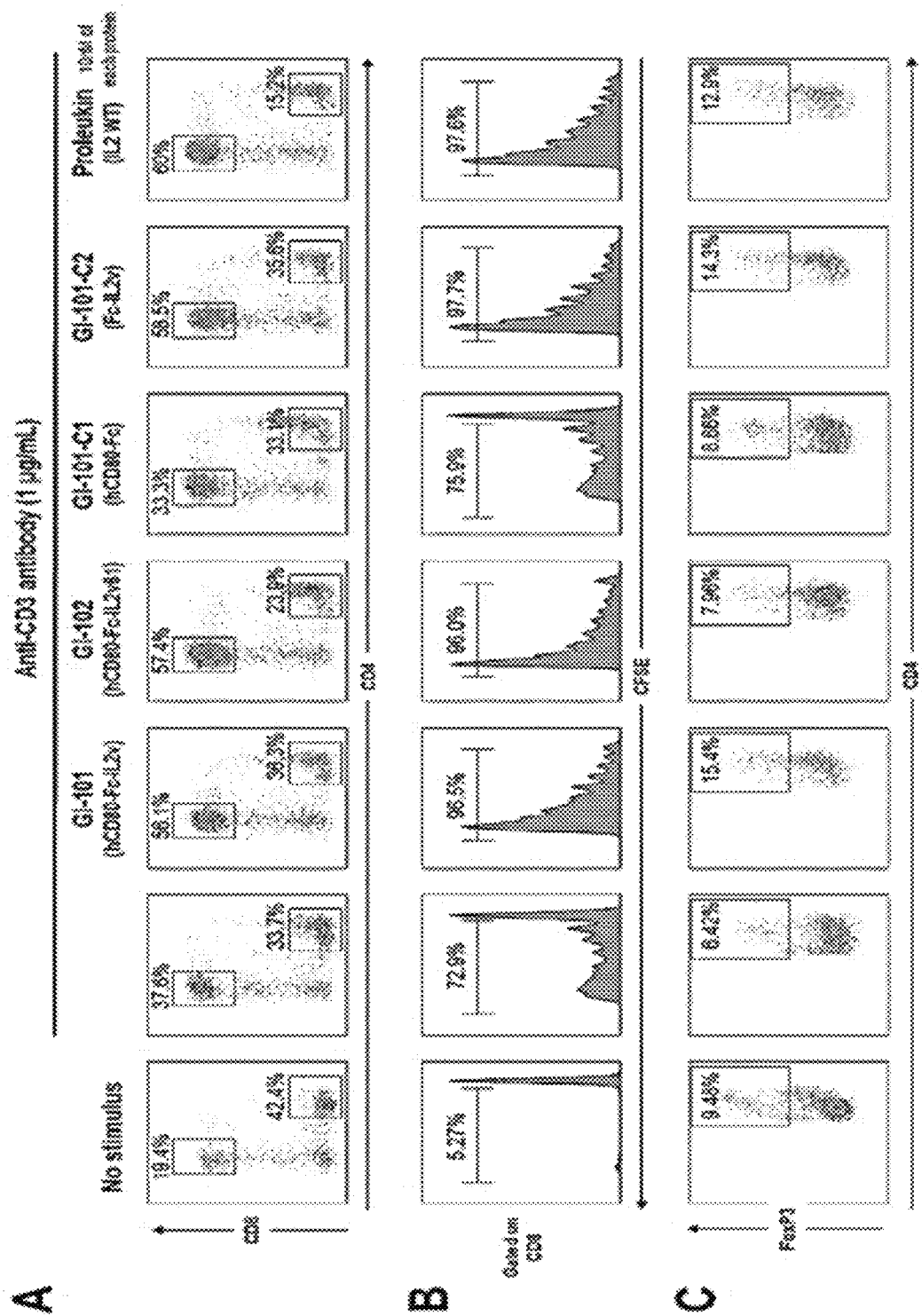

[Fig. 36]
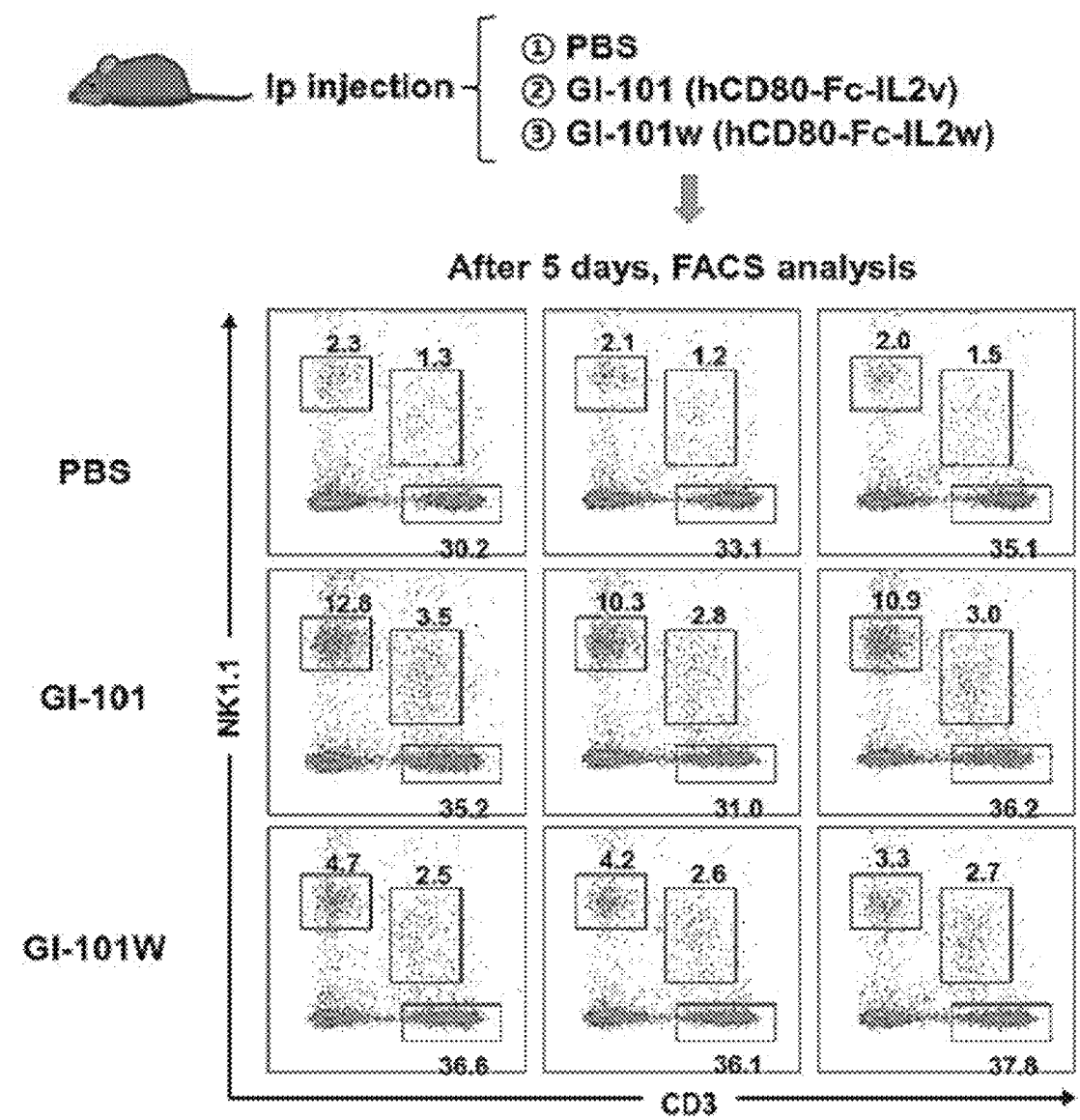

[Fig. 37]
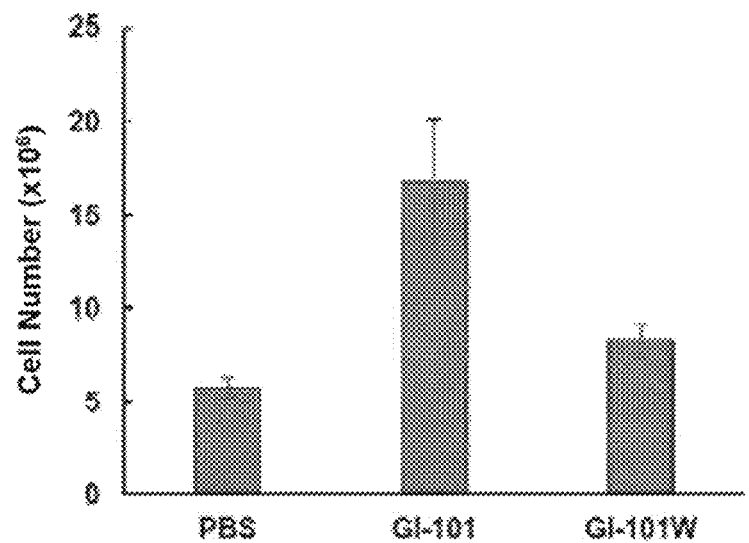
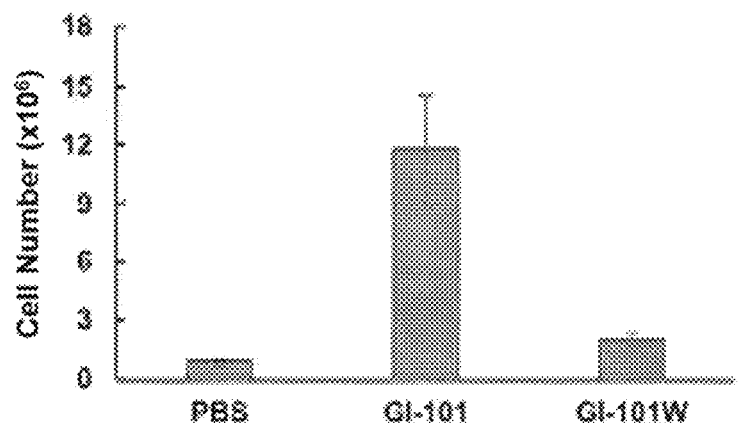

[Fig. 38]
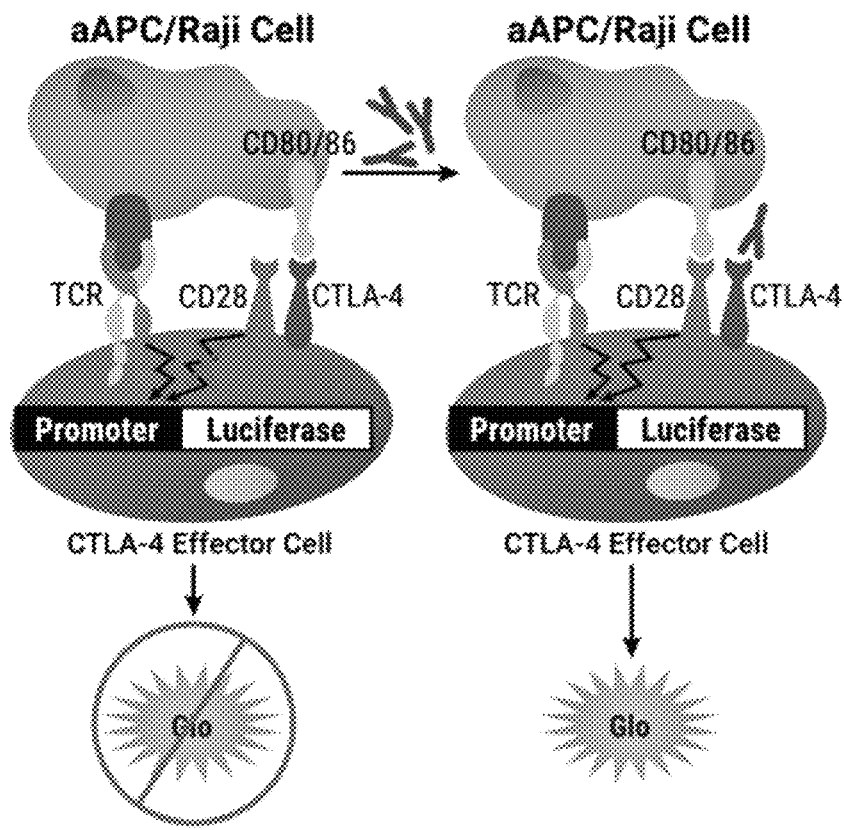
[Fig. 39]
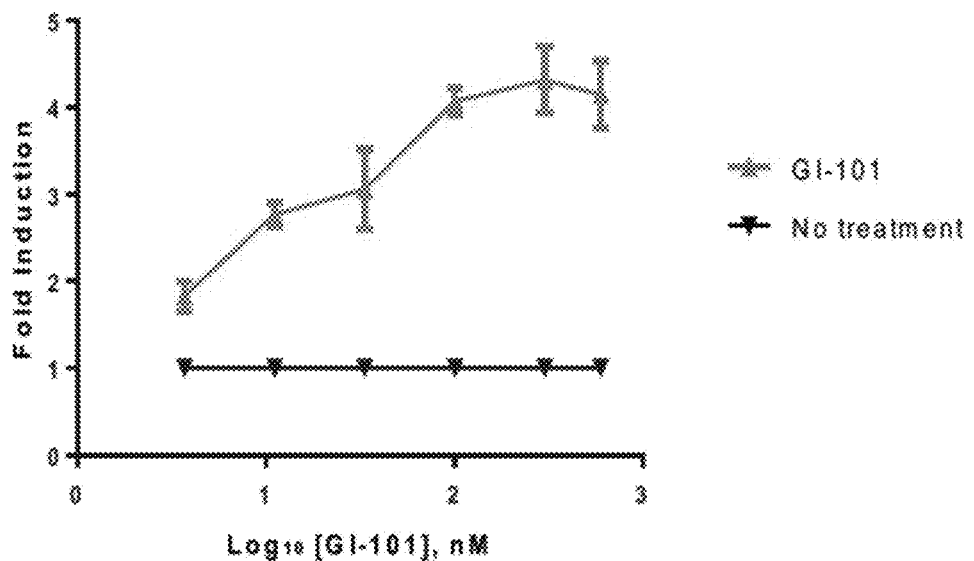

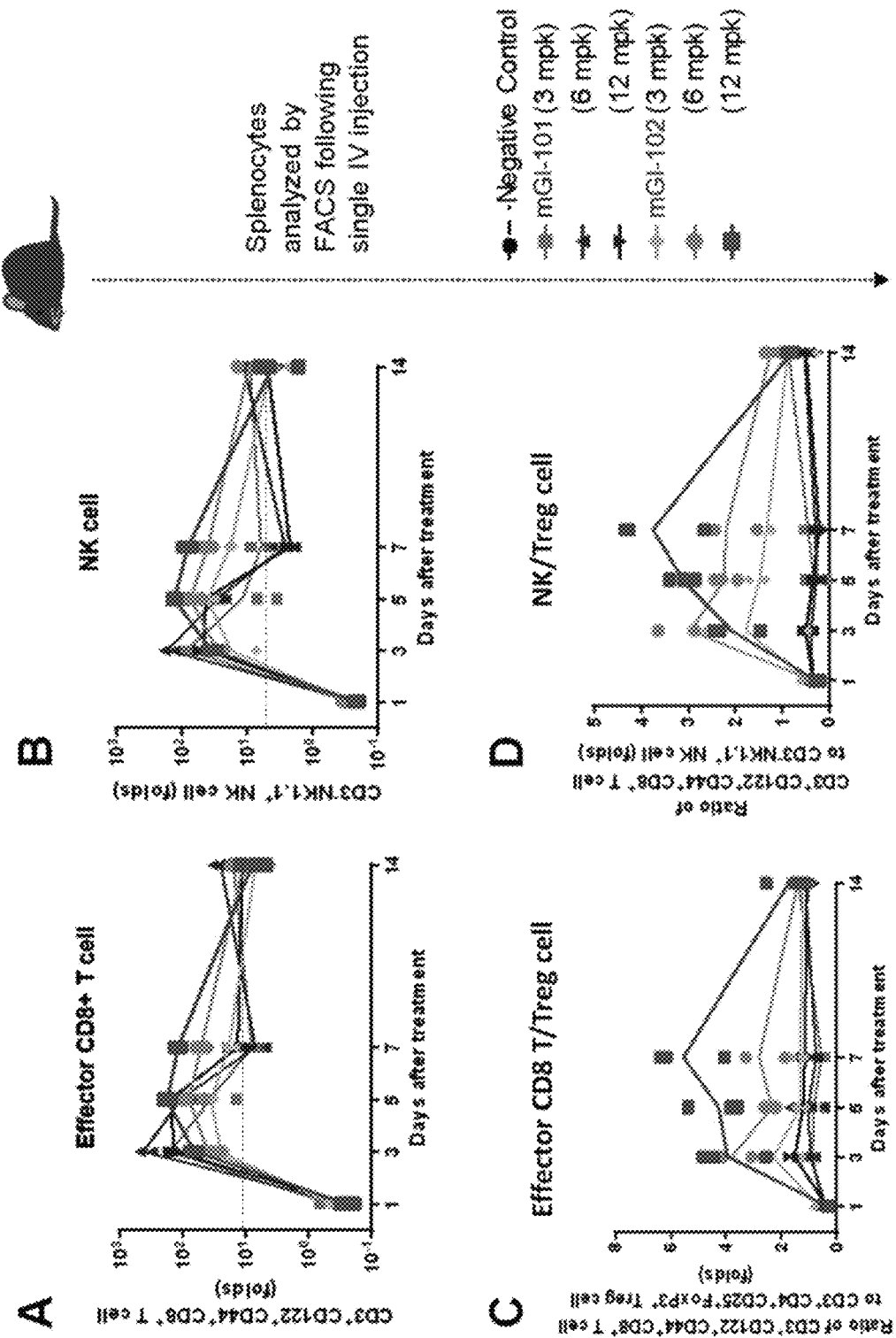

[Fig. 41]
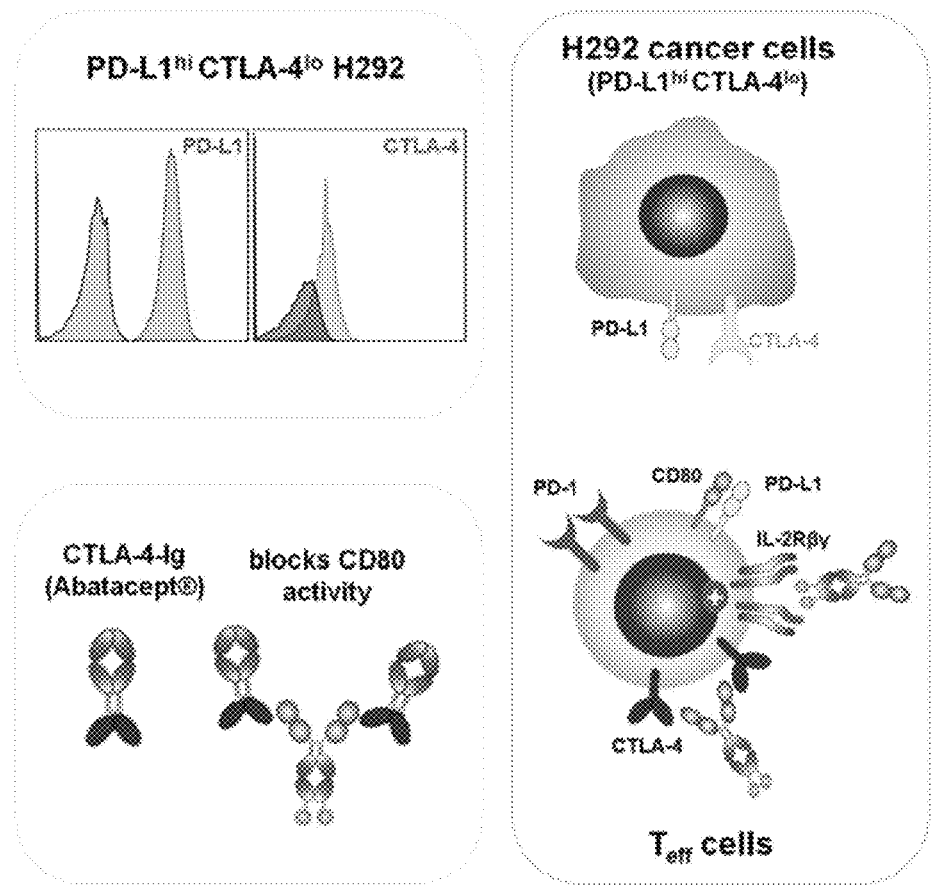
[Fig. 42]
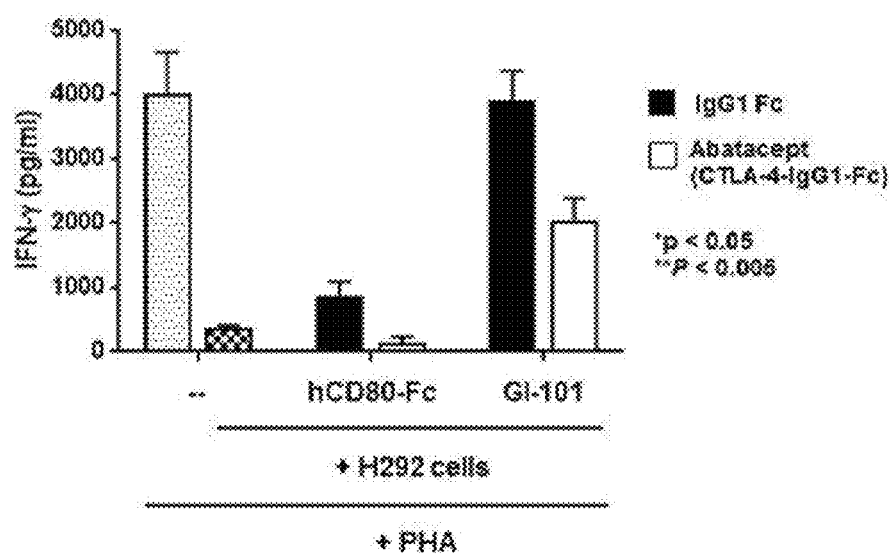

[Fig. 43]
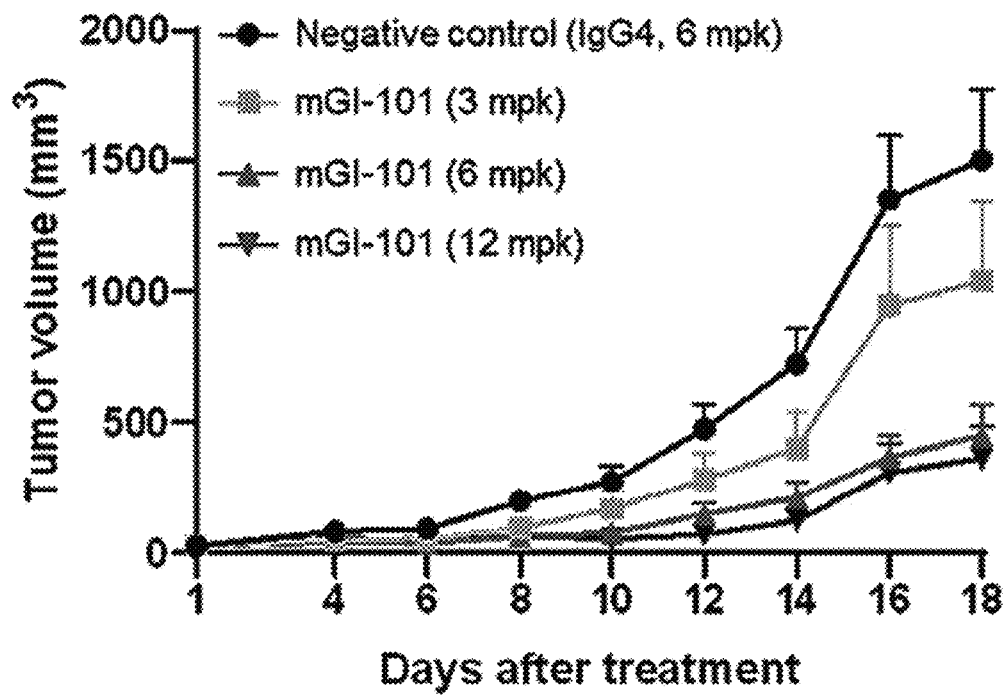
[Fig. 44]
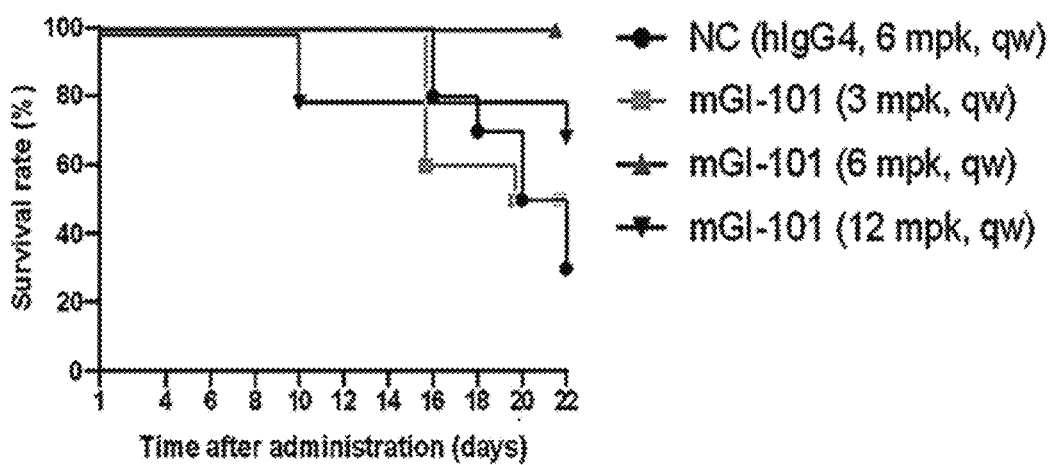

[Fig. 45]
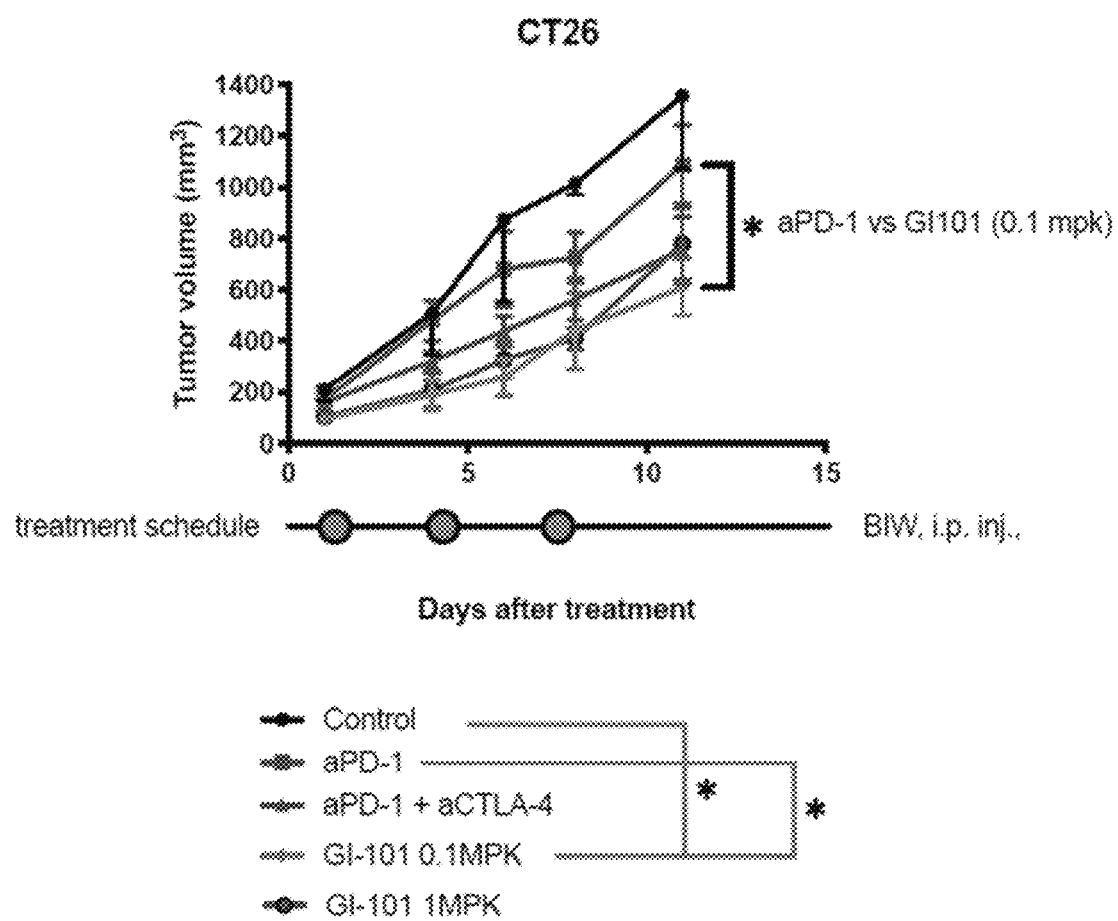

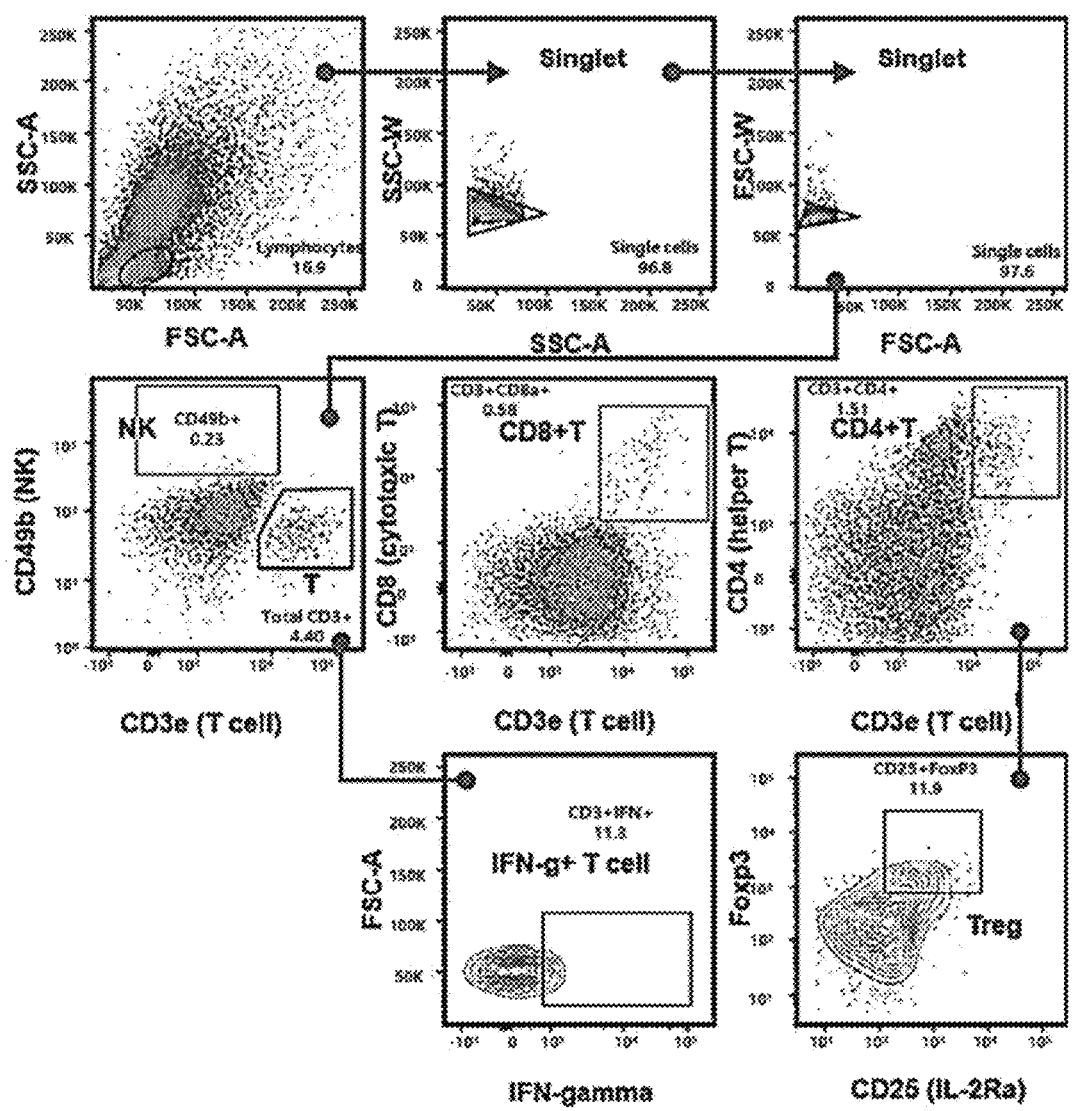
[Fig. 46]

[Fig. 47]
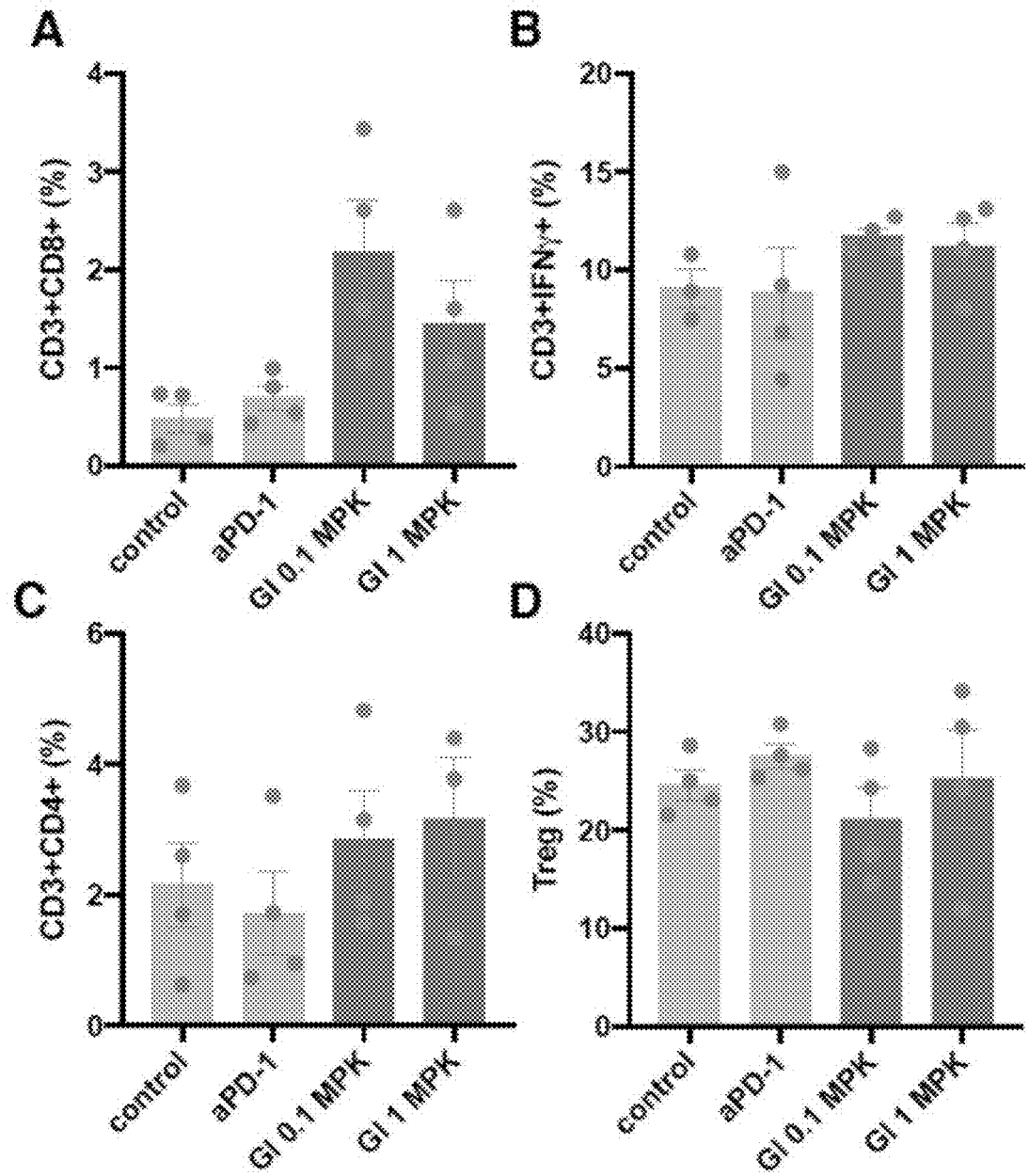

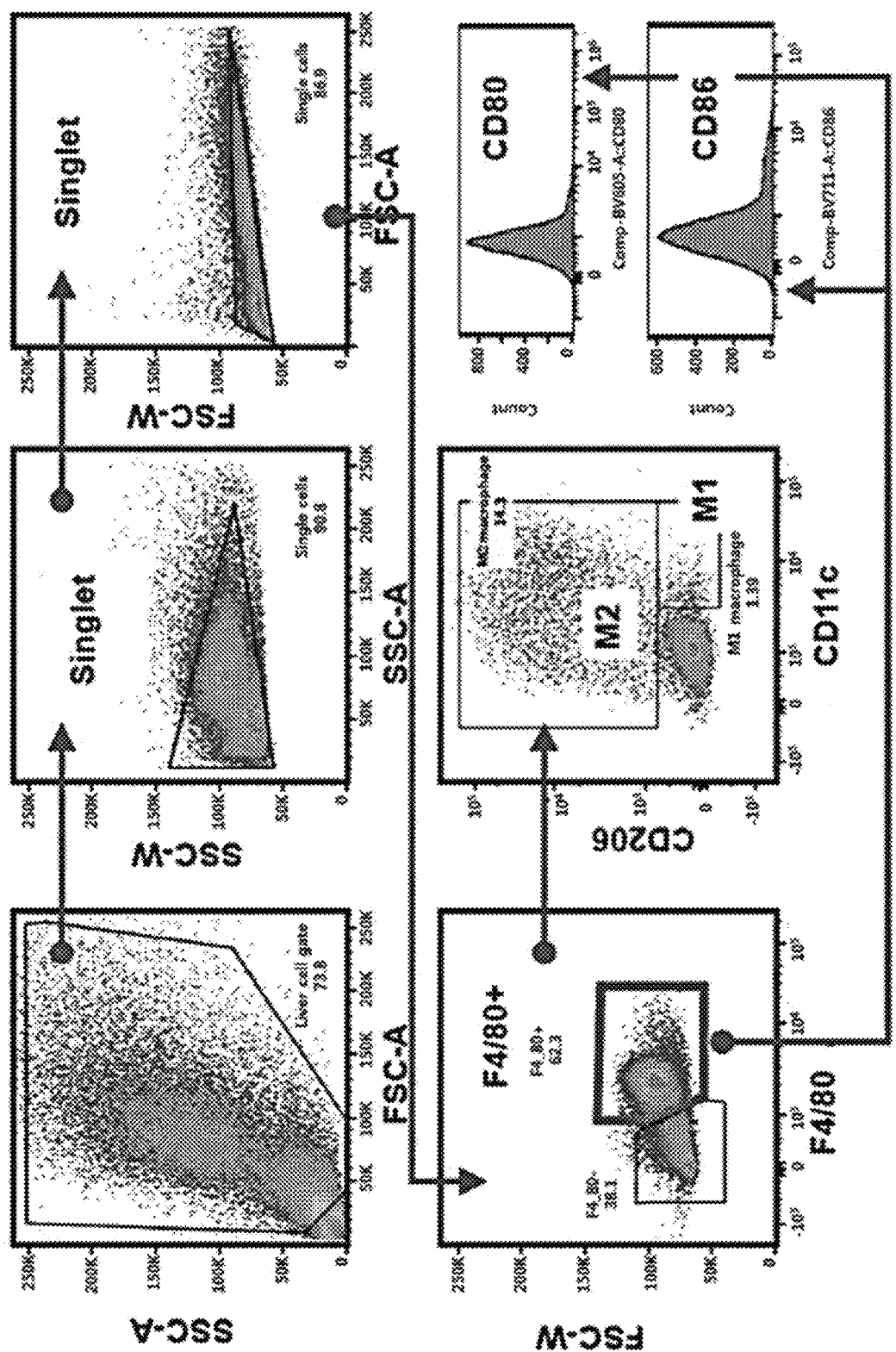
[Fig. 48]

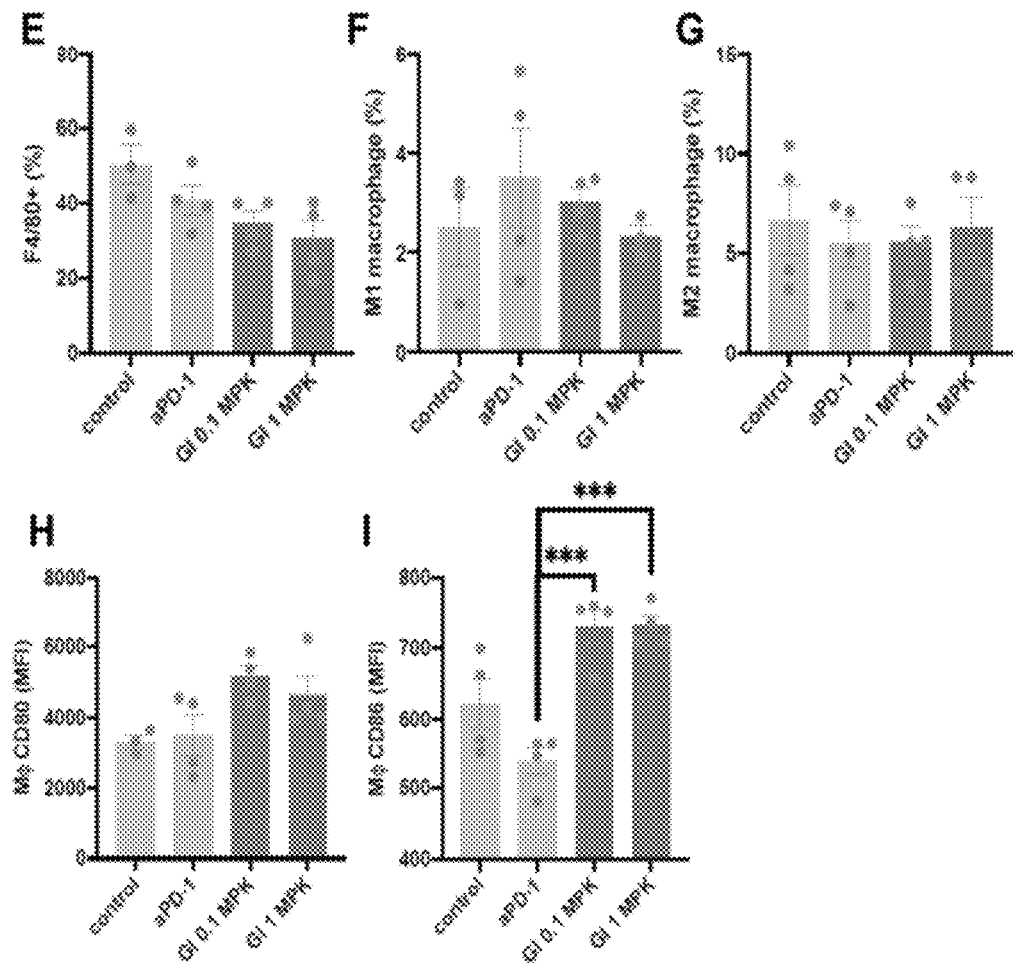
[Fig. 49]

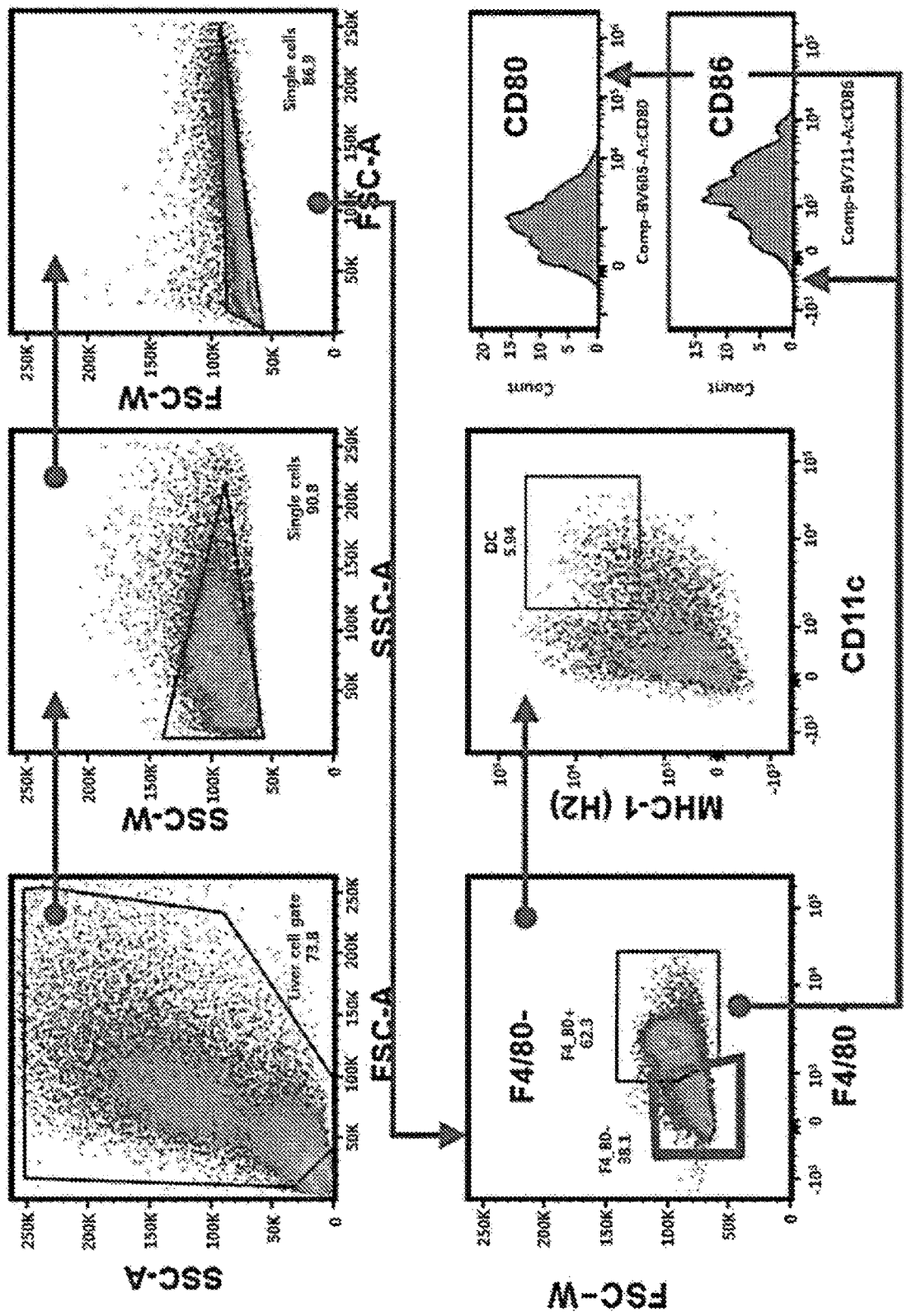
[Fig. 50]

[Fig. 51]
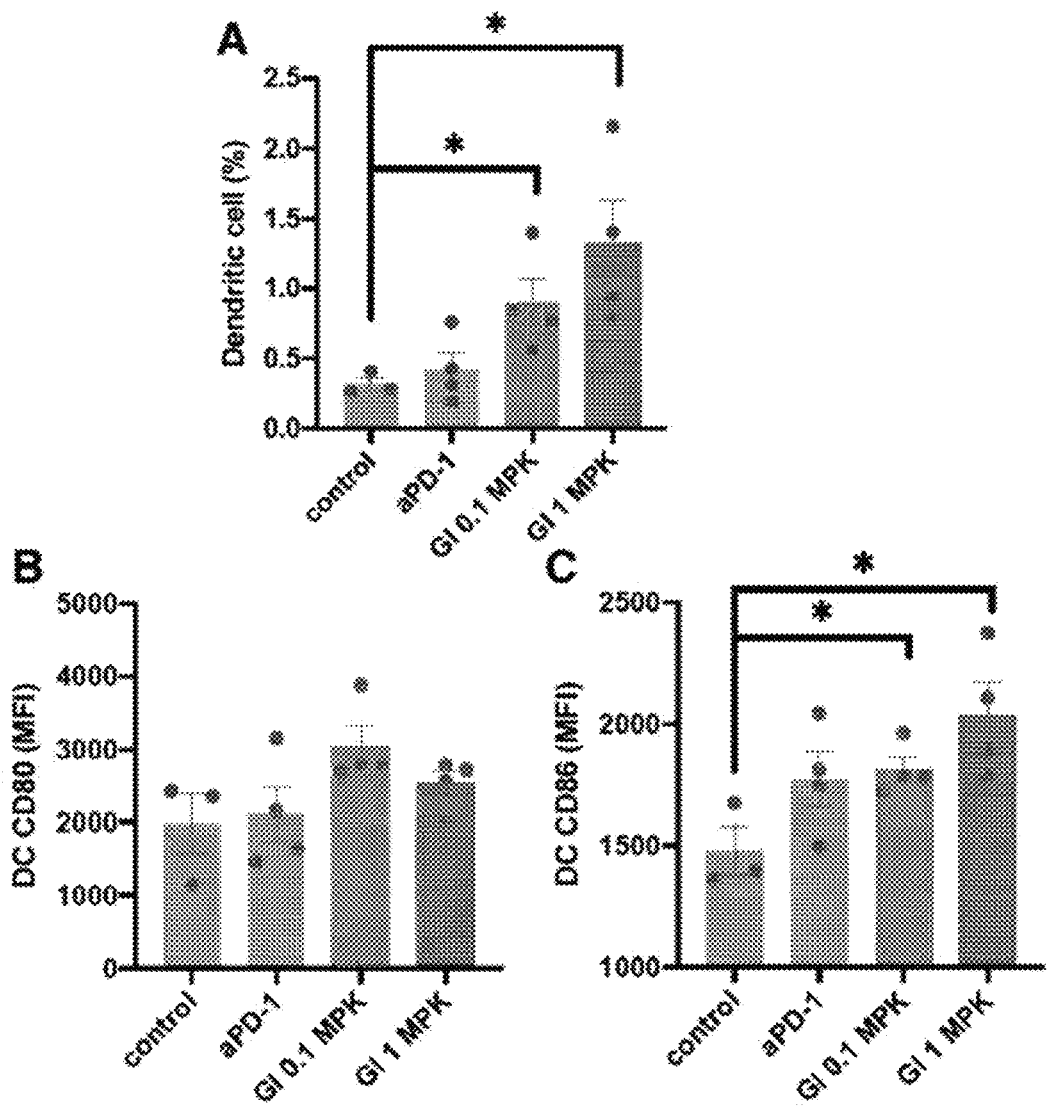

[Fig. 52]
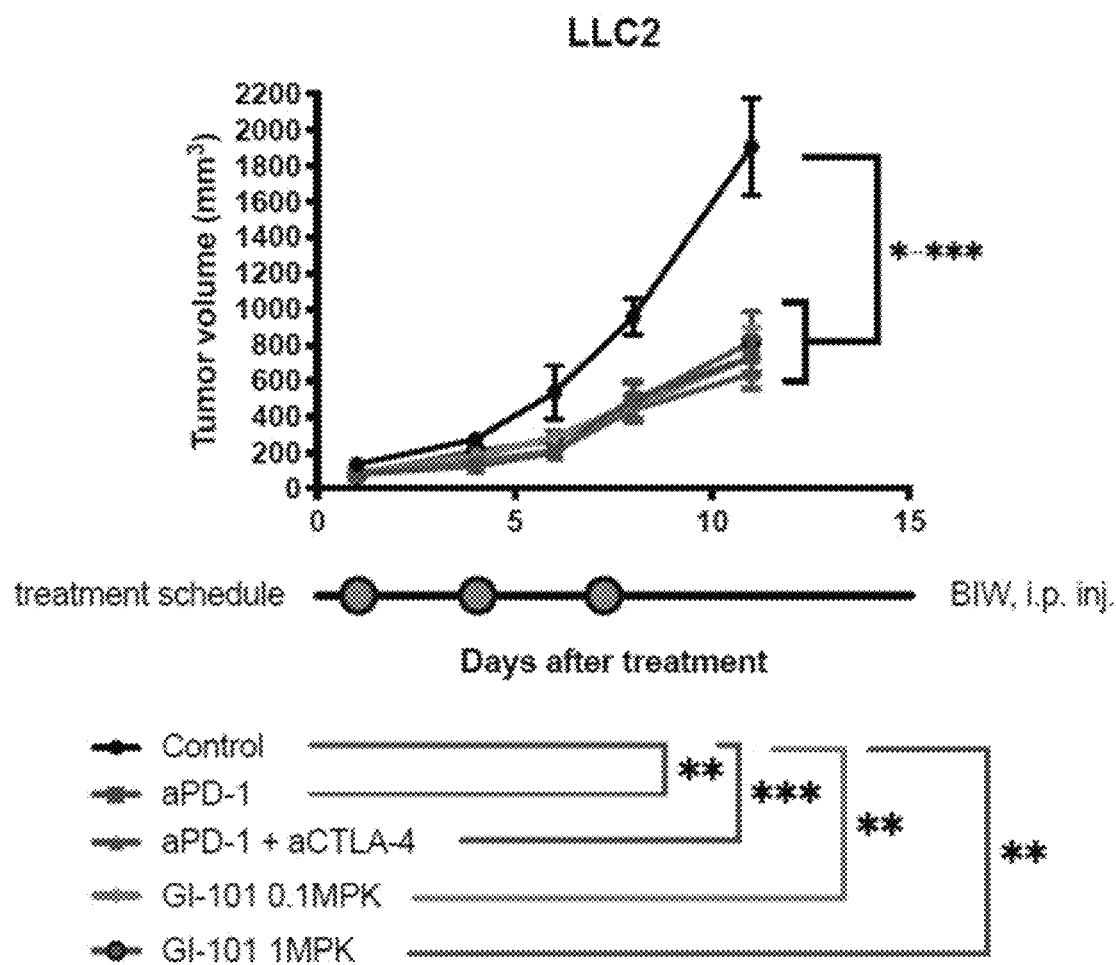

[Fig. 53]
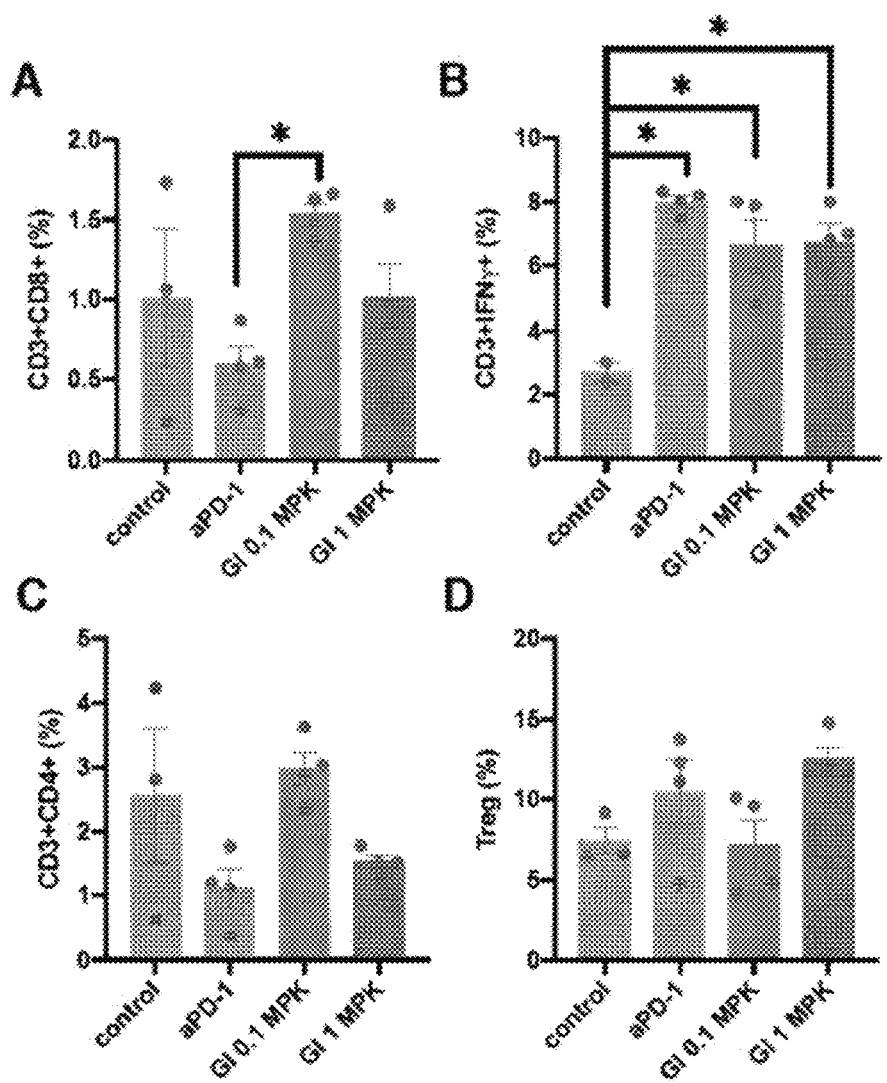

[Fig. 54]
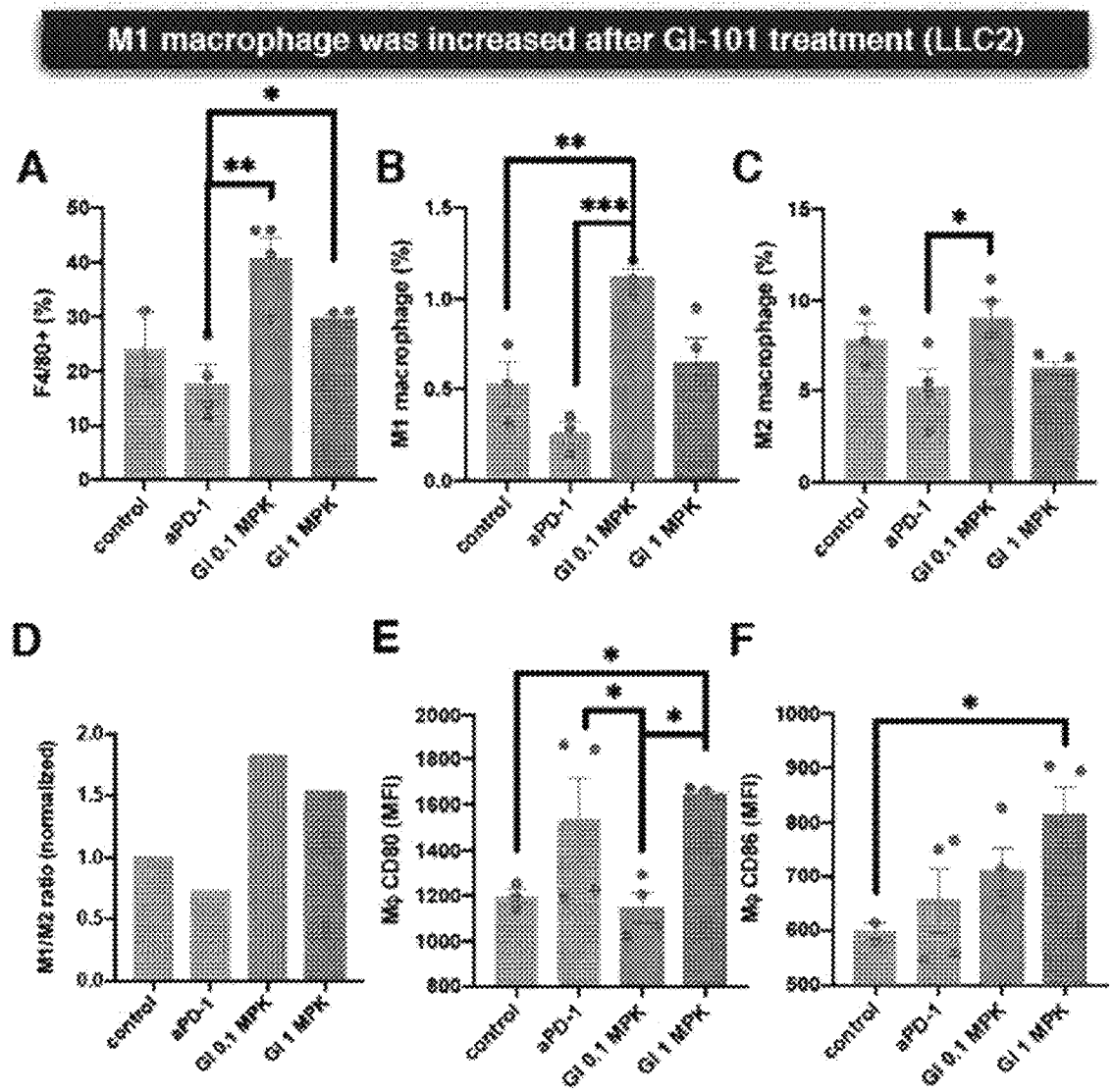

[Fig. 55]
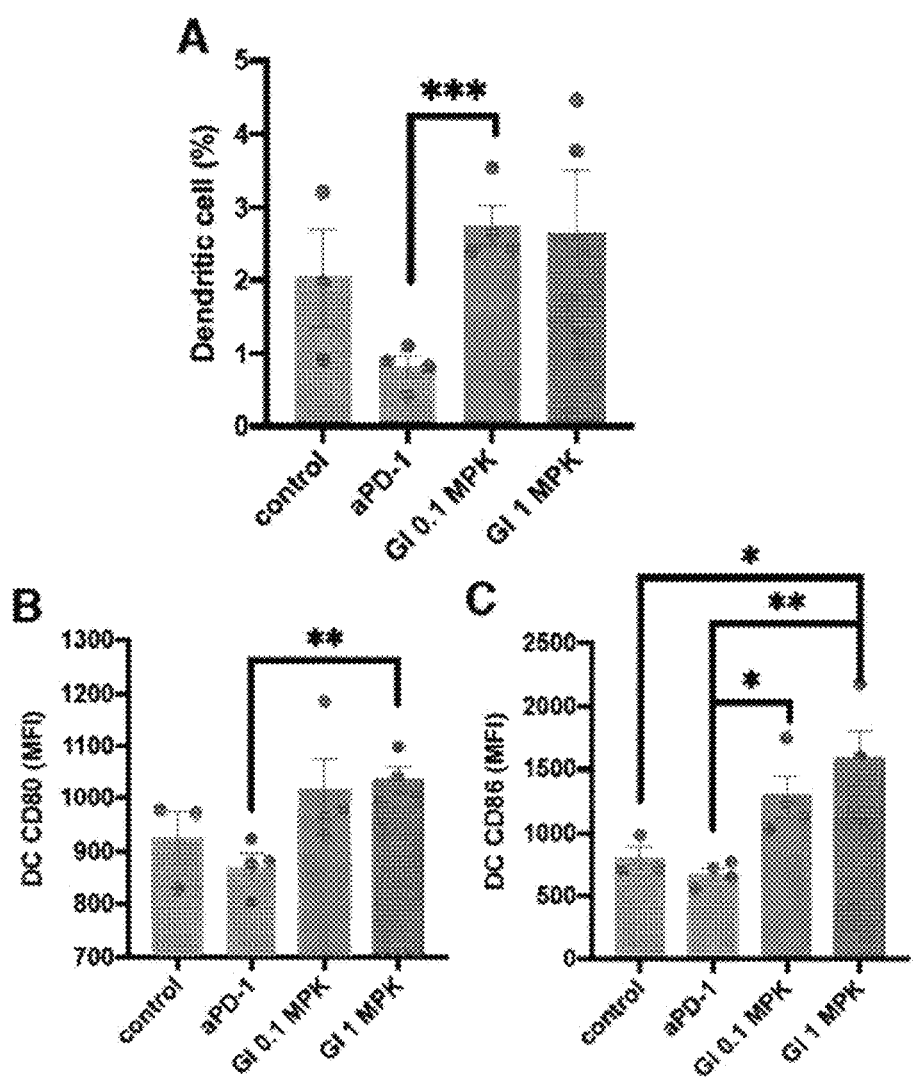

[Fig. 56]
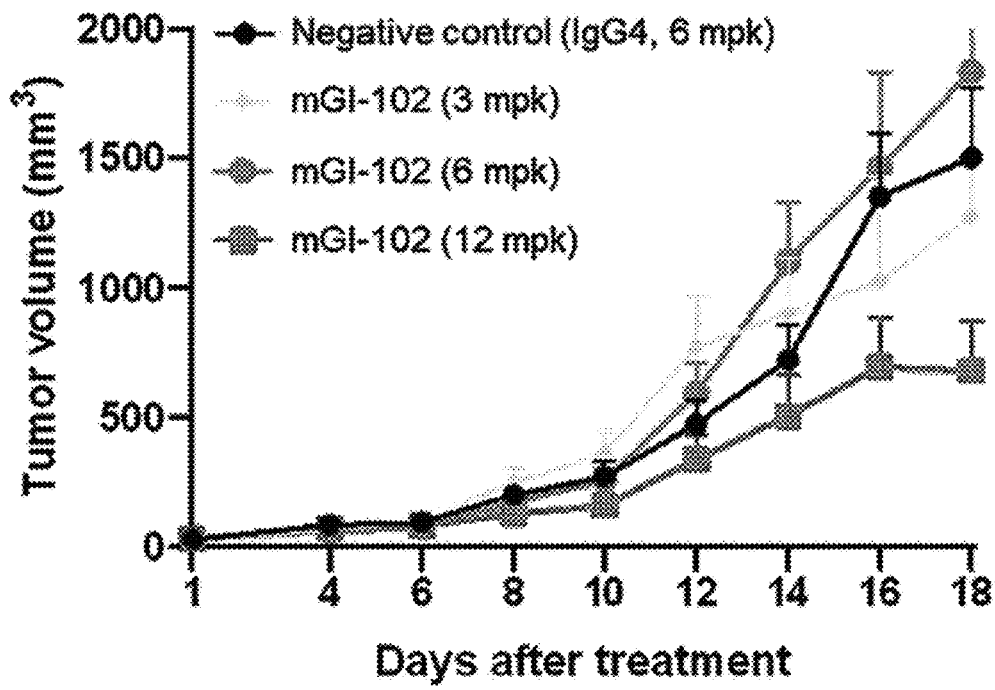
[Fig. 57]
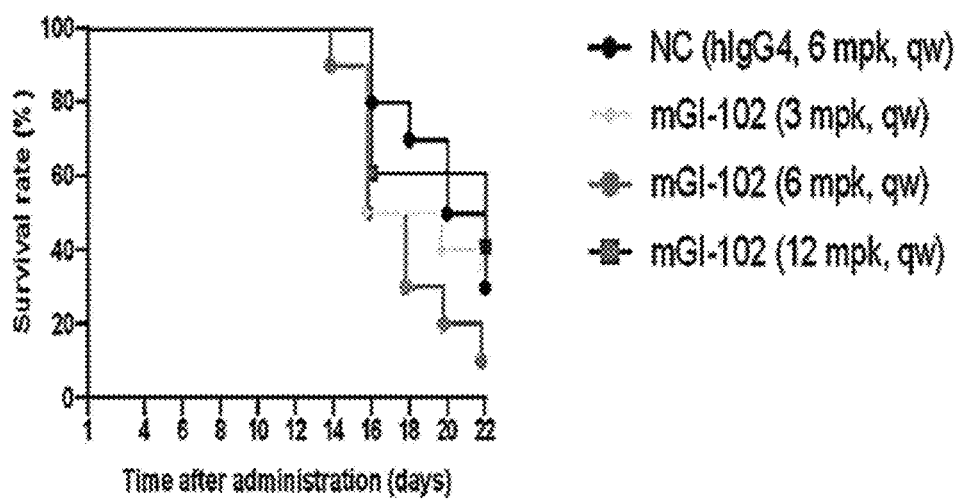

[Fig. 58]
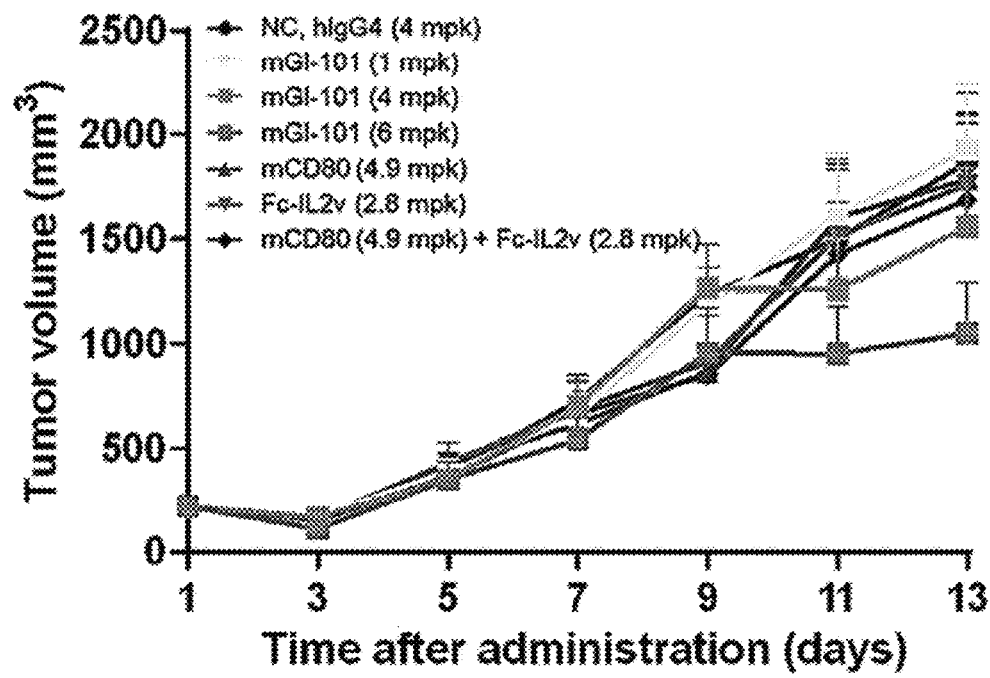
[Fig. 59]
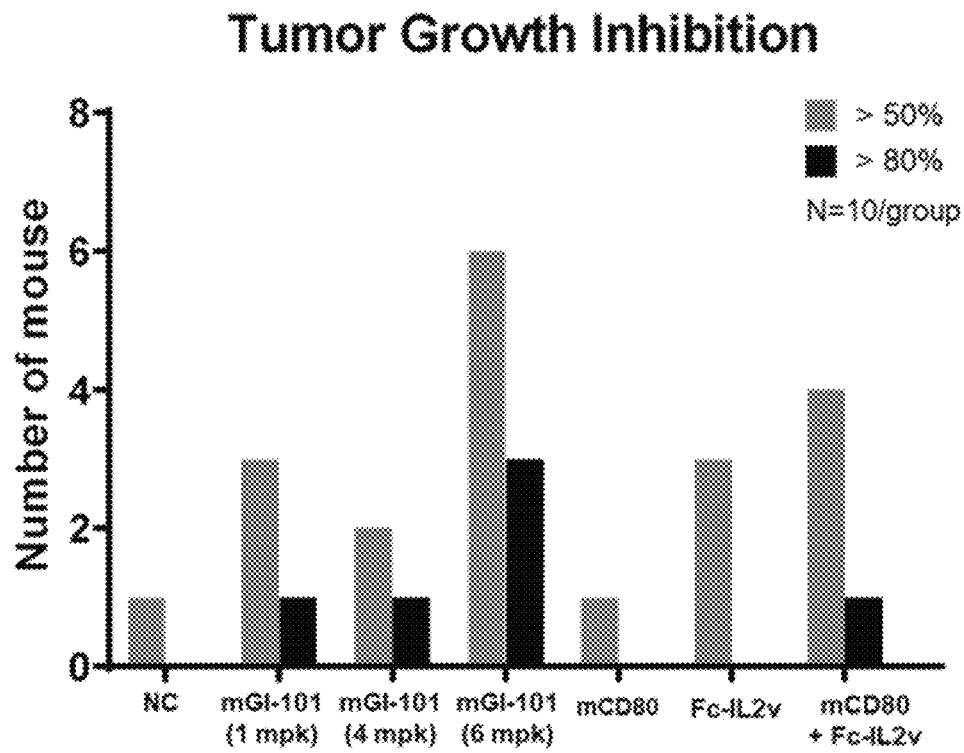

[Fig. 60]
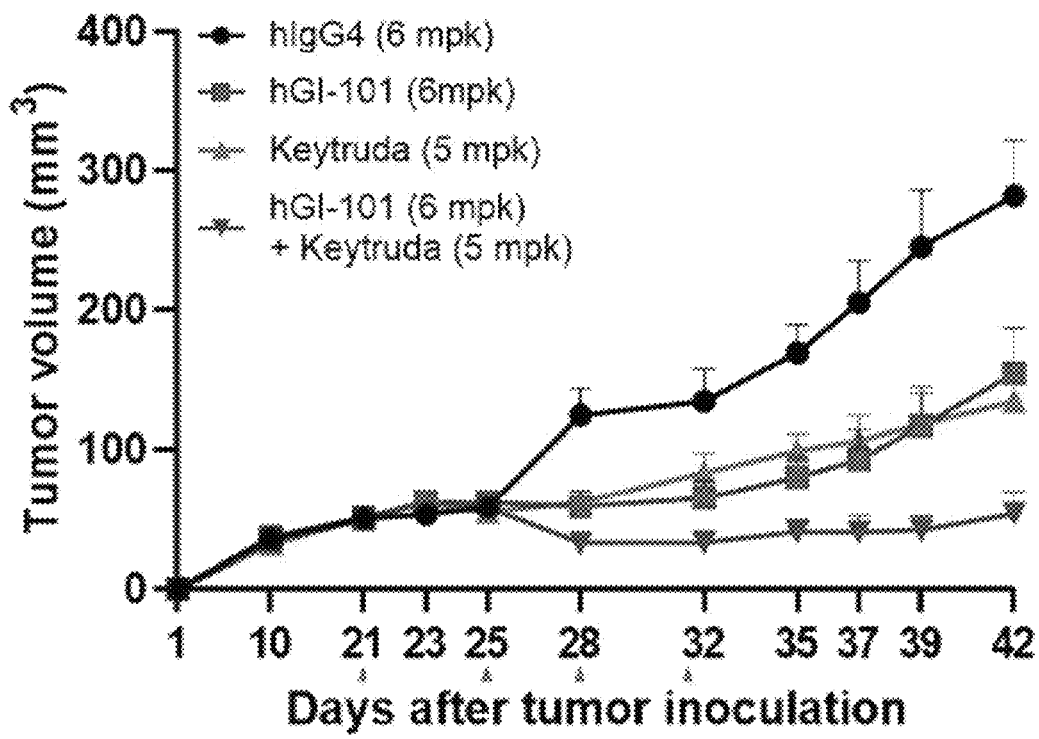
[Fig. 61]
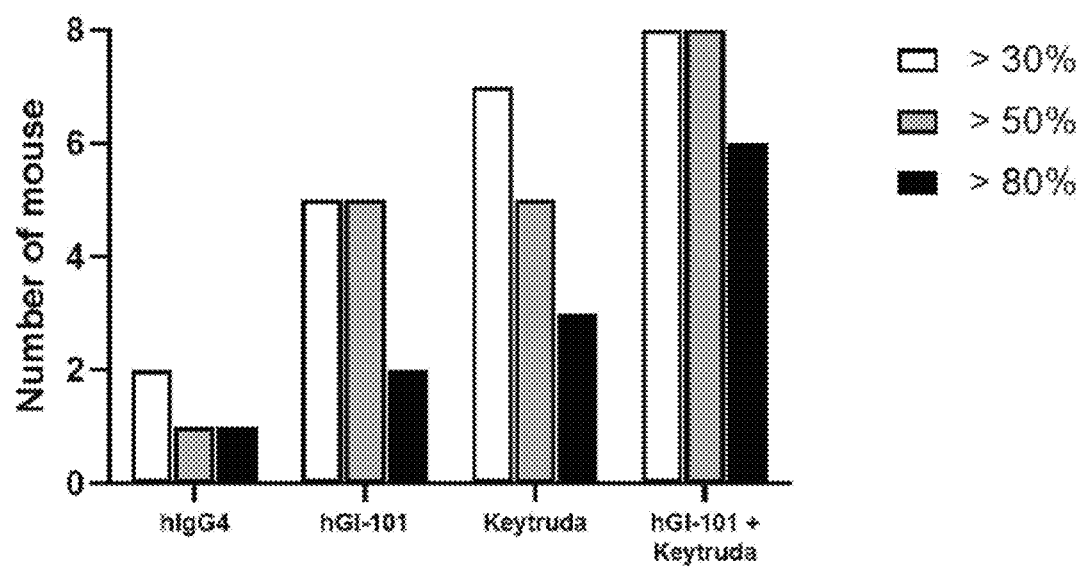

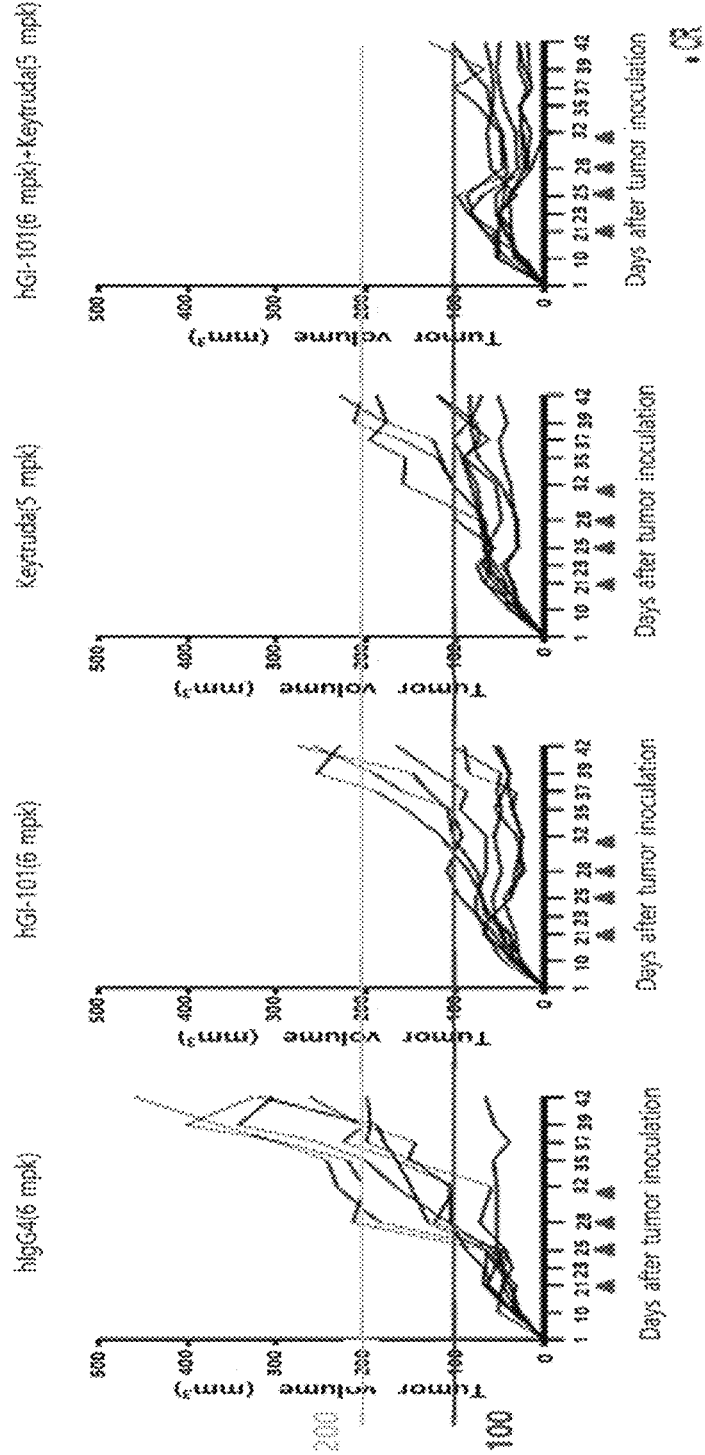
[Fig. 62]

[Fig. 63]
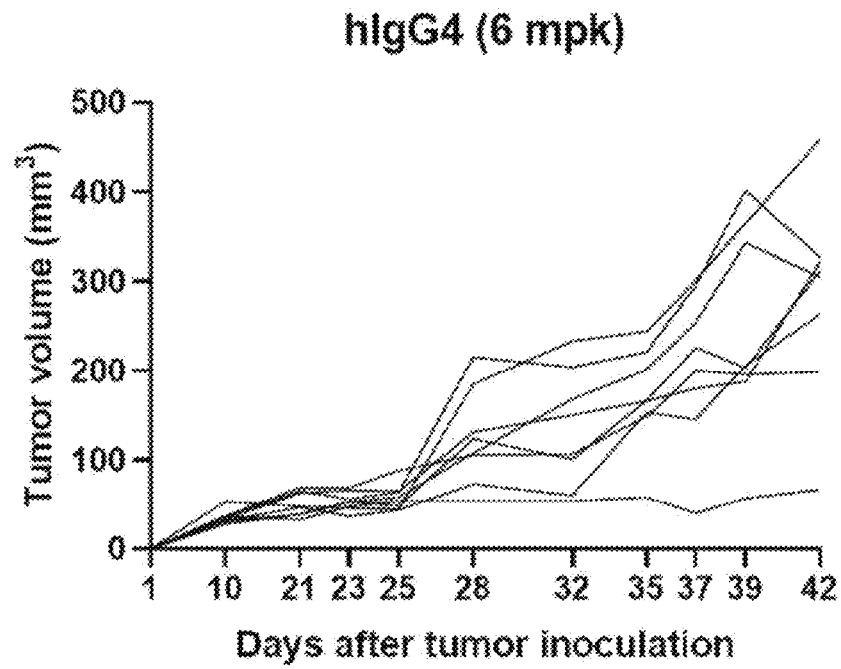
[Fig. 64]
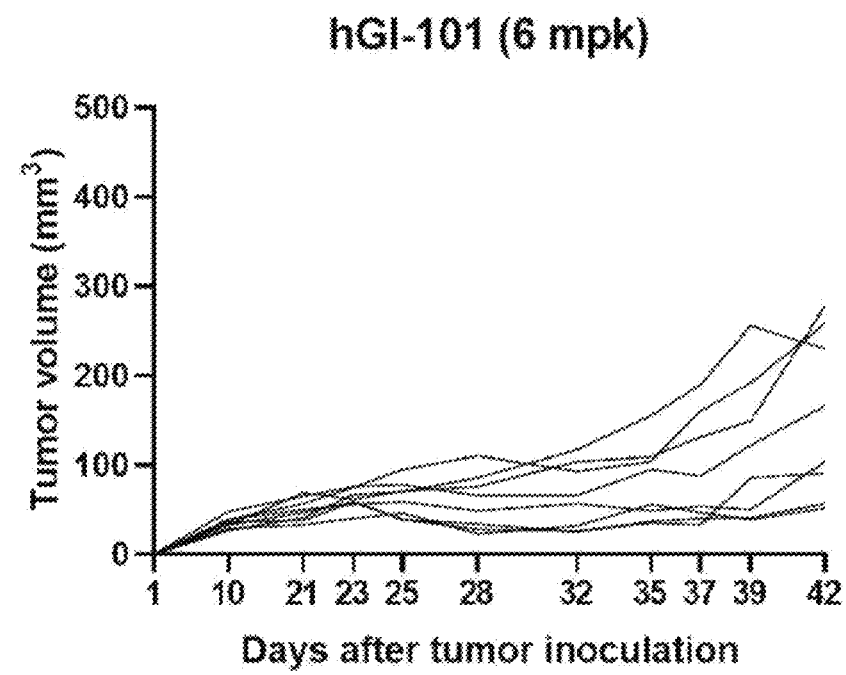

[Fig. 65]
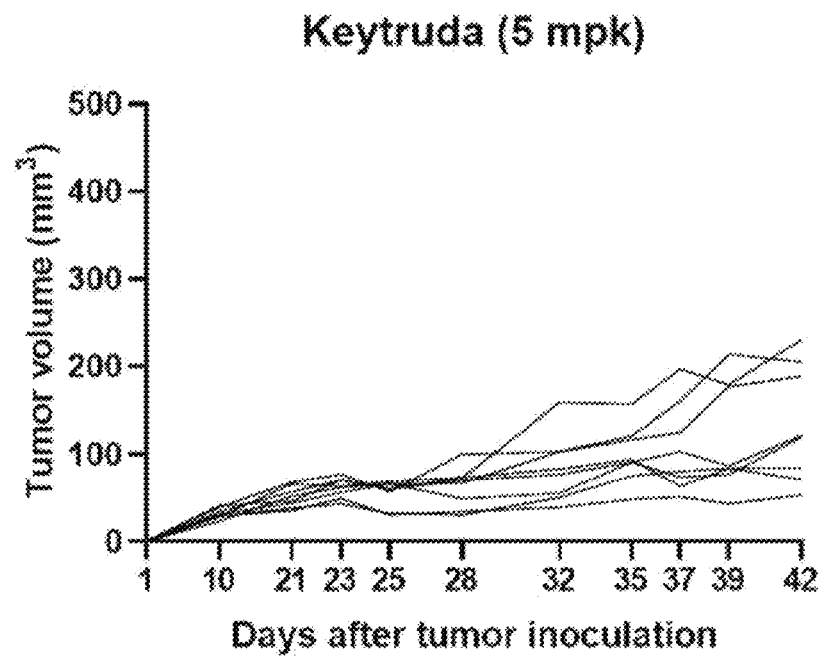
[Fig. 66]
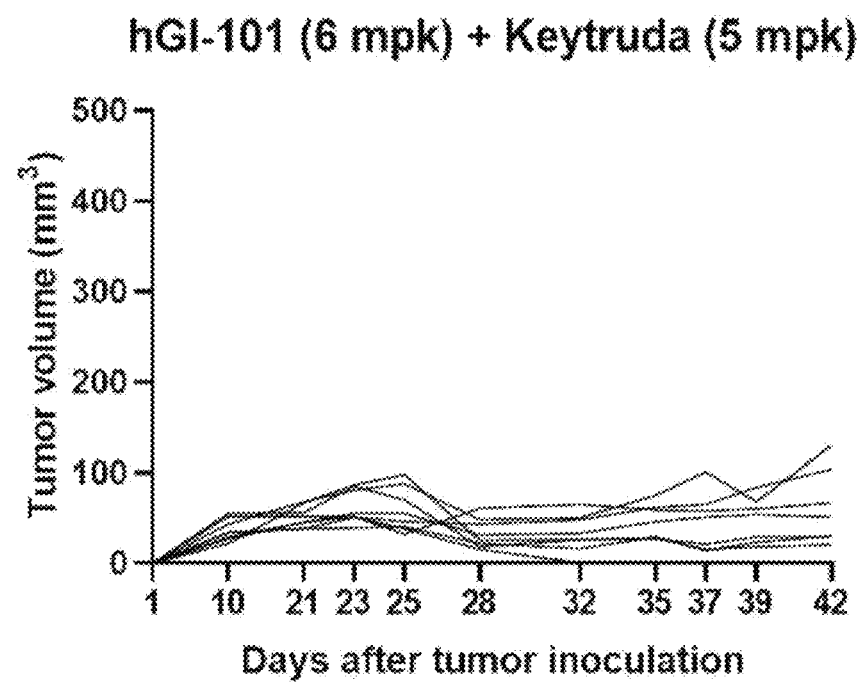

[Fig. 67]
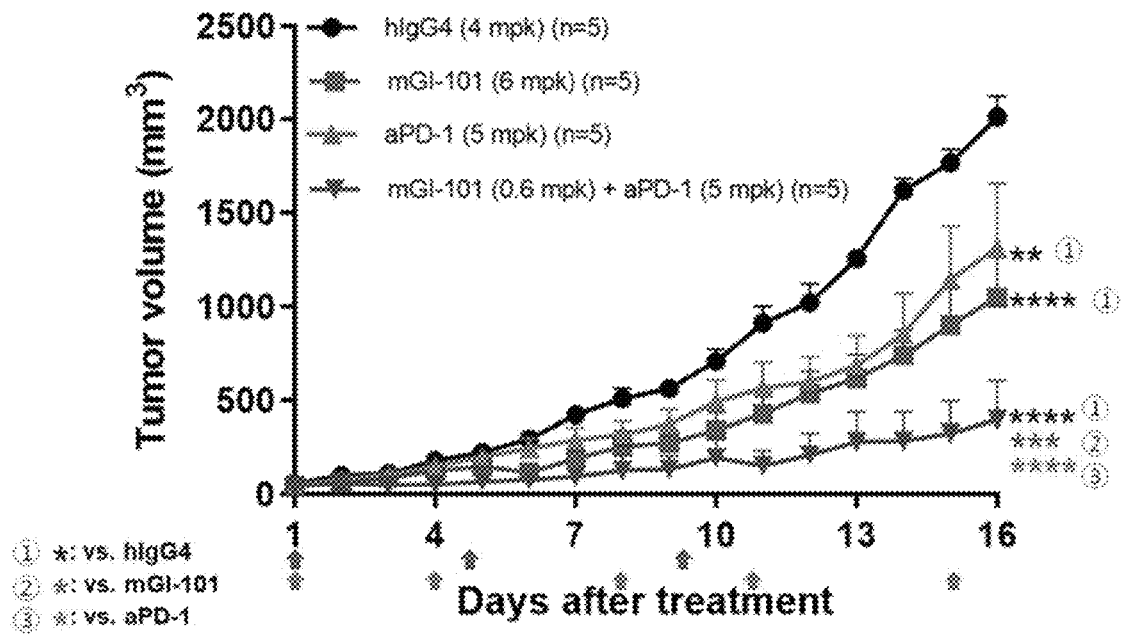
[Fig. 68]
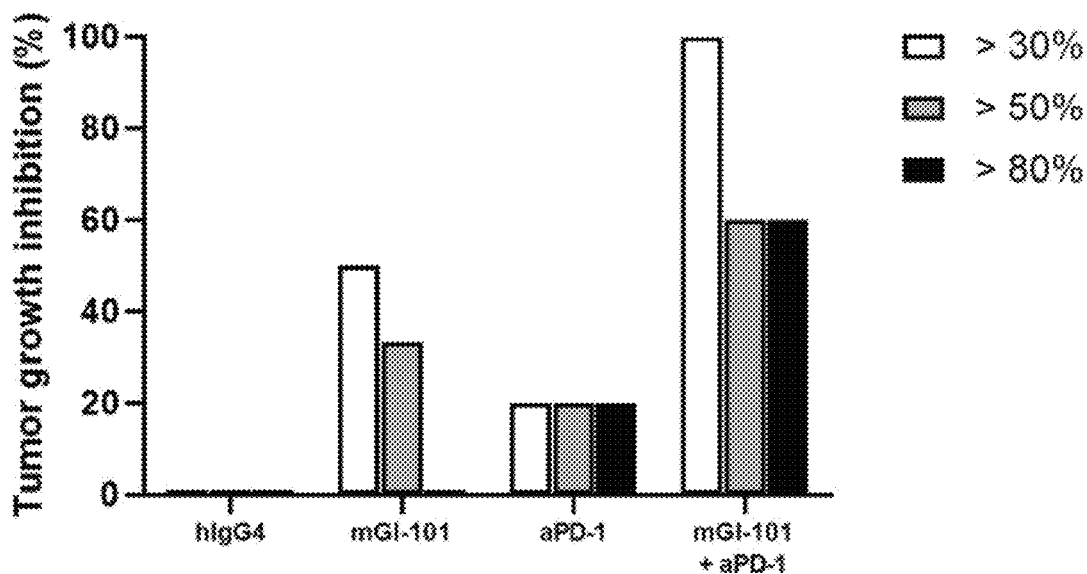

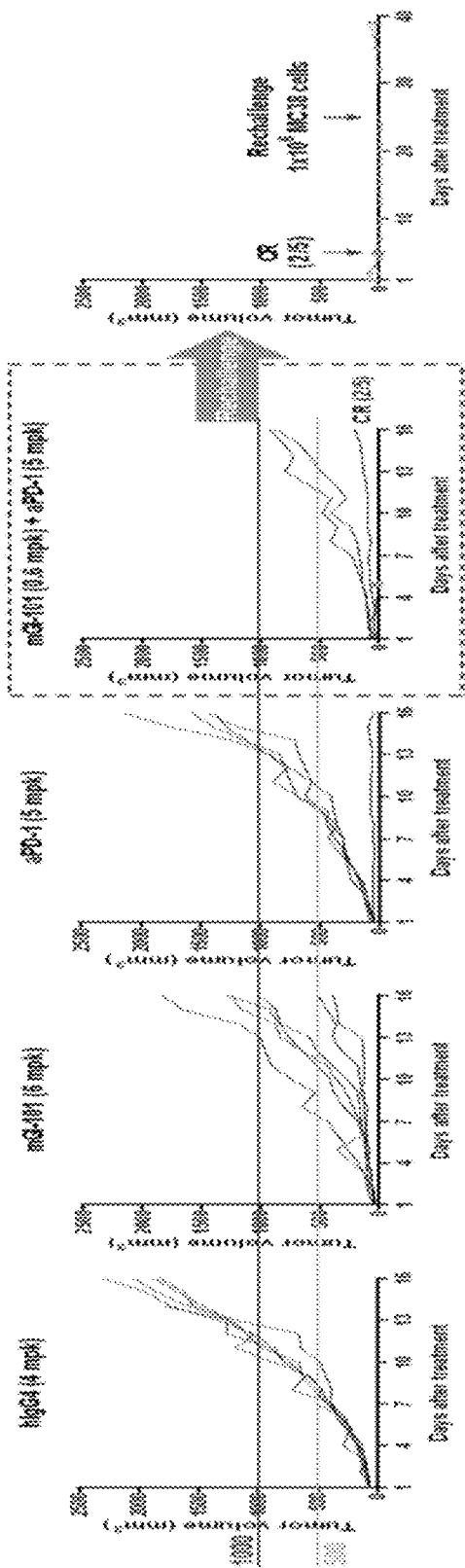

[Fig. 70]
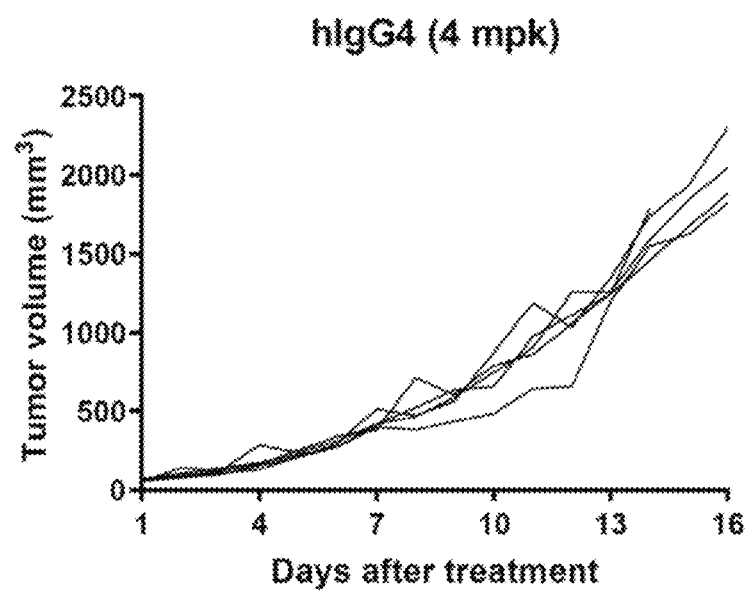
hIgG4 (4 mpk)
[Fig. 71]
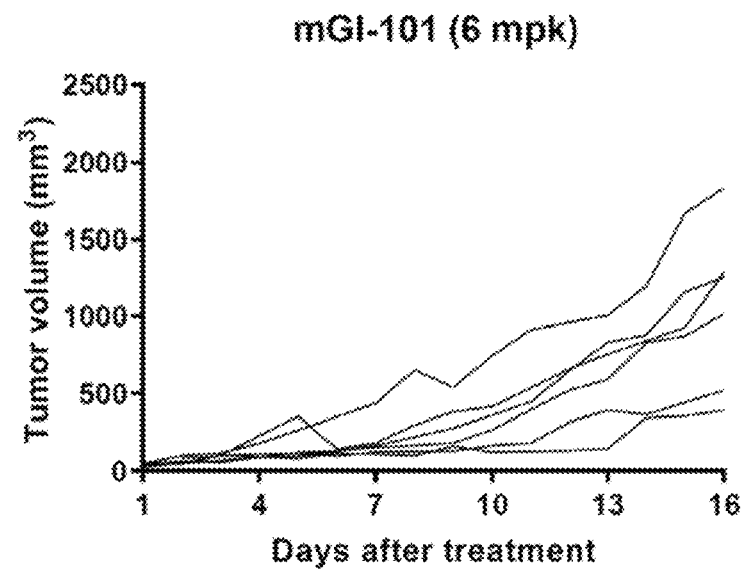
mGI-101 (6 mpk)

[Fig. 72]
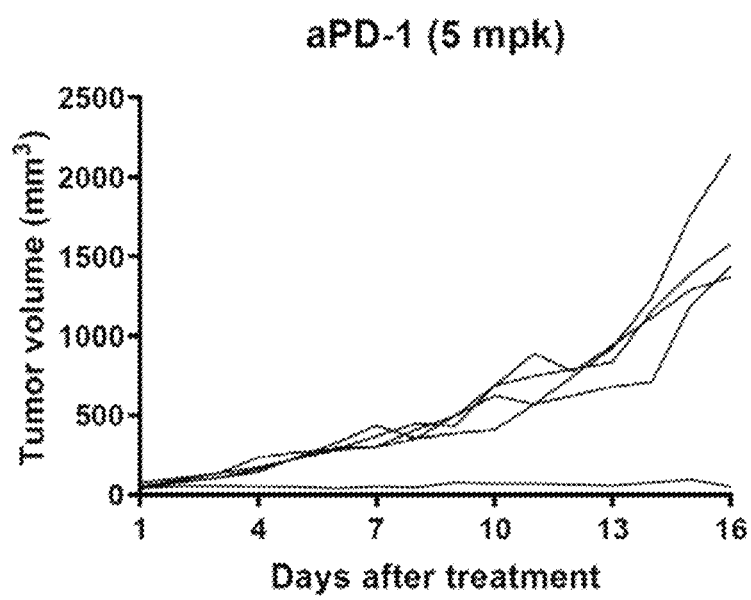
[Fig. 73]
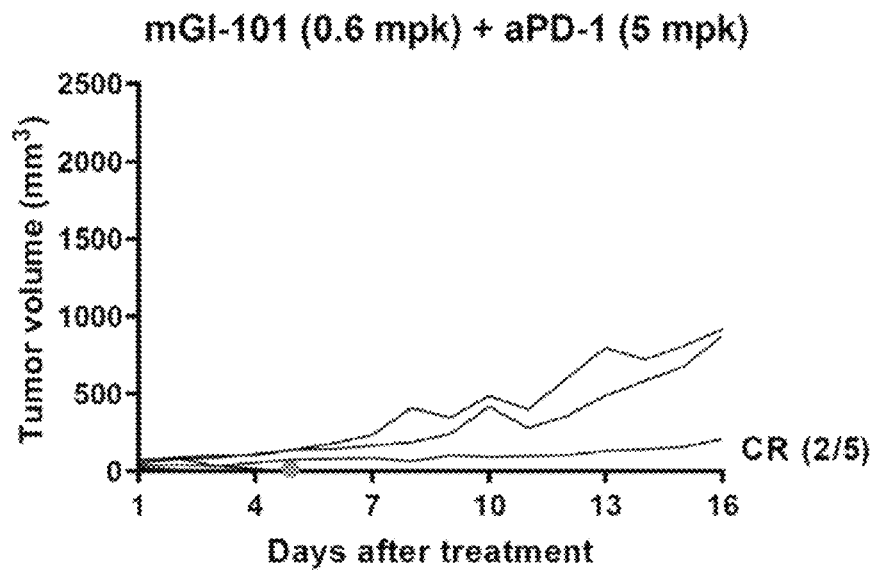

[Fig. 74]
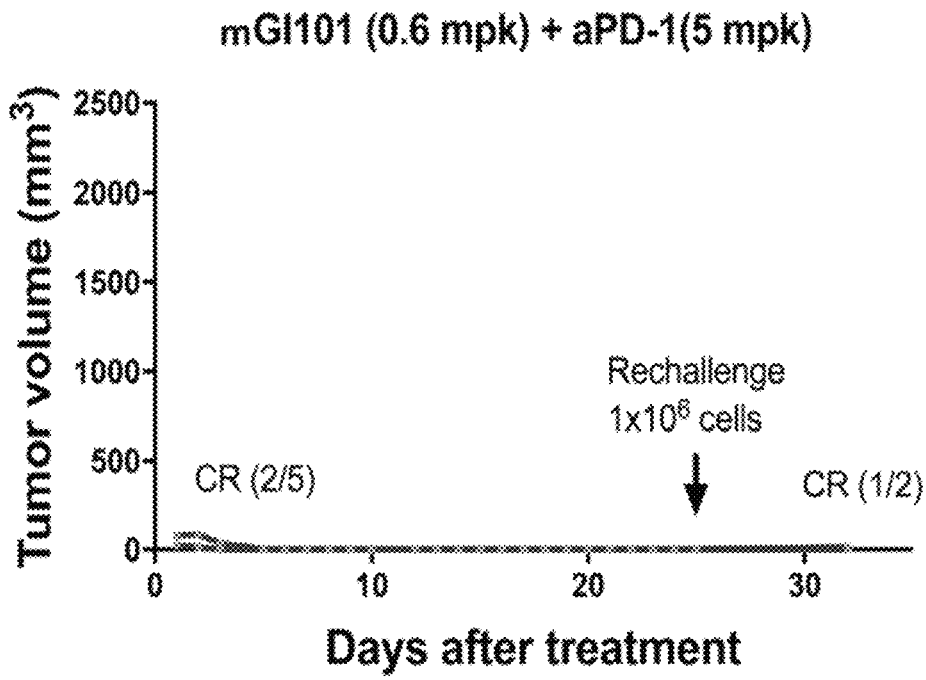
[Fig. 75]
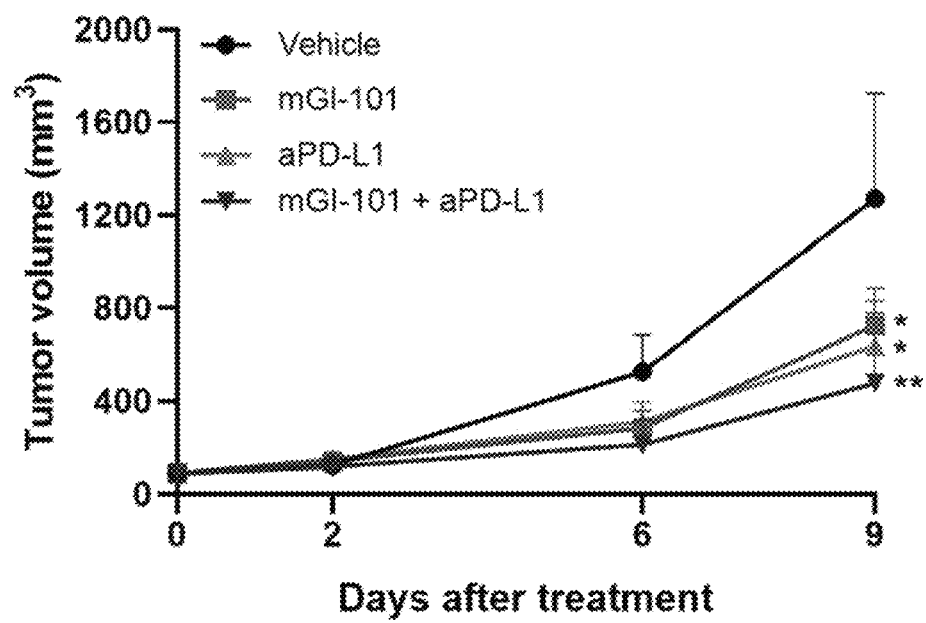

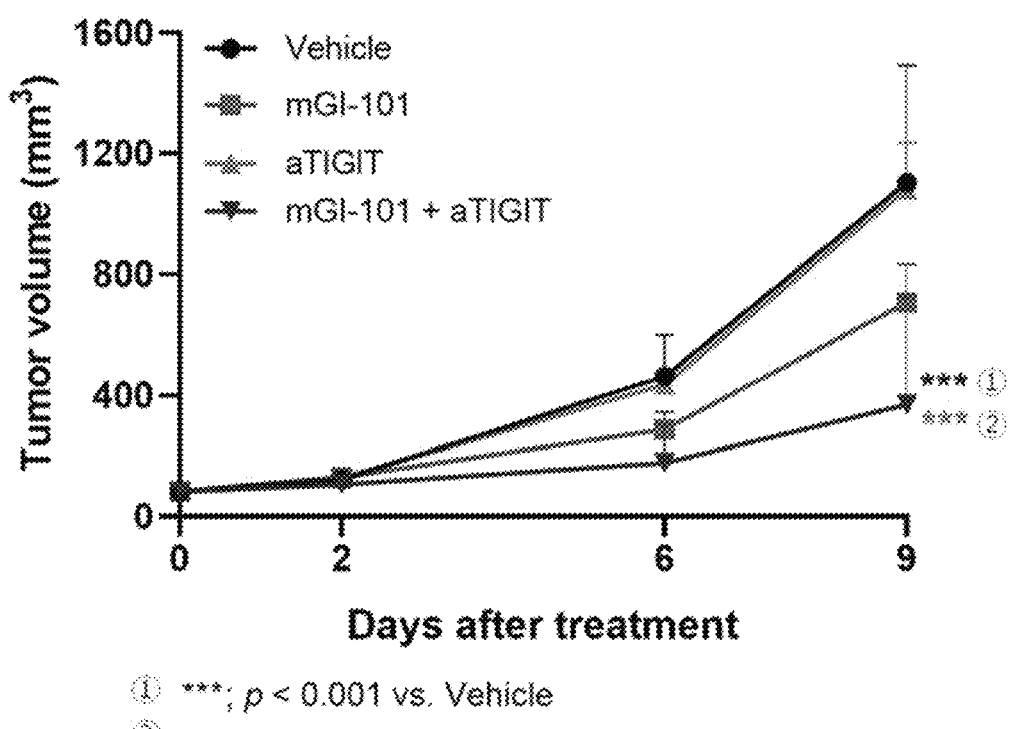
[Fig. 76]
① ***; p < 0.001 vs. Vehicle
② ***; p < 0.001 vs. aTIGIT

PHARMACEUTICAL COMPOSITION FOR TREATMENT OF CANCER, COMPRISING AN IMMUNE CHECKPOINT INHIBITOR ANTIBODY AND A FUSION PROTEIN COMPRISING AN IL-2 MUTANT AND A CD80 EXTRACELLULAR DOMAIN

CROSS REFERENCE TO RELATED APPLICATIONS

This application is a National Stage of International Application No. PCT/KR2020/017097 filed Nov. 27, 2020, claiming priority based on Korean Patent Application No. 10-2019-0154632 filed Nov. 27, 2019.

SEQUENCE LISTING

The content of the electronically submitted sequence listing, file name: Sequence_Listing_As_Filed.txt; size: 99,154 bytes; and date of creation: May 26, 2022, filed herewith, is incorporated herein by reference in its entirety.

TECHNICAL FIELD

The present invention relates to a pharmaceutical composition for treating cancer comprising, as active ingredients, a fusion protein dimer comprising an IL-2 protein or a variant thereof and a CD80 protein or a fragment thereof, and an immune checkpoint inhibitor.

BACKGROUND ART

Interleukin 2 (IL-2), also called T-cell growth factor (TCGF), is a globular glycoprotein that plays a central role in lymphocyte production, survival, and homeostasis. IL-2 has a protein size of 15.5 kDa to 16 kDa and consists of 133 amino acids. IL-2 mediates various immune actions by binding to an IL-2 receptor composed of three distinct subunits.

In addition, IL-2 is synthesized mainly by activated T cells, in particular by CD4+ helper T cells. IL-2 stimulates proliferation and differentiation of T cells, and induces production of cytotoxic T lymphocytes (CTLs) and differentiation of peripheral blood lymphocytes into cytotoxic cells and lymphokine-activated killer cells (LAK cells).

Meanwhile, CD80, also known as B7-1, is a member of the B7 family of membrane-bound proteins that are involved in immune regulation by binding to its ligand by way of delivering costimulatory responses and coinhibitory responses. CD80 is a transmembrane protein expressed on the surface of T cells, B cells, dendritic cells, and monocytes. CD80 is known to bind CD28, CTLA4 (CD152), and PD-L1. CD80, CD86, CTLA4, and CD28 are involved in a costimulatory-coinhibitory system. For example, they regulate activity of T cells and are involved in proliferation, differentiation, and survival thereof.

In addition, recently, immune checkpoint inhibitors such as Keytruda® are in the spotlight. Immune checkpoint inhibitors are anticancer agents that help to attack cancer cells by activating body's immune system. Cancer treatment to date has focused on killing rapidly dividing cells, which is the characteristic of cancer cells, so that there are side effects of acting on not only cancer cells but also rapidly dividing cells among normal cells. However, it is known that immune anticancer agents use the immune system of a cancer patient to affect cancer cells, so there are few typical side effects of existing anticancer agents. An anti-PD-1 antibody such as Keytruda binds to the specific receptor (PD-1) of T cells and blocks the pathway of cancer cells to avoid surveillance system of active T cells, thereby exhibiting an anticancer effect through immune reactivation which allows T cells in human body to attack cancer cells (Korean Laid-open Patent Publication No. 2018-0030580A).

DETAILED DESCRIPTION OF THE INVENTION

Technical Problem

Accordingly, as a result of studying to develop a safe and effective anticancer agent, the present inventors found out that a novel fusion protein dimer comprising an IL-2 protein or a variant thereof and a CD80 protein or a fragment thereof in one molecule and an immune checkpoint inhibitor exhibit an excellent anticancer effect, and thereby have completed the present invention.

Solution to Problem

To achieve the above object, an aspect of the present invention provides a pharmaceutical composition for treating cancer containing, as active ingredients, a fusion protein dimer comprising an IL-2 protein or a variant thereof and a CD80 protein or a fragment thereof, and an immune checkpoint inhibitor.

Effect of the Invention

The fusion protein dimer comprising an IL-2 protein or a variant thereof and a CD80 protein or a fragment thereof can activate immune cells by IL-2. In addition, it was confirmed that the fusion protein dimer exhibits synergistic effects when administered in combination with an immune checkpoint inhibitor. Therefore, the pharmaceutical composition for treating cancer containing, as active ingredients, a fusion protein dimer comprising an IL-2 protein or a variant thereof and a CD80 protein or a fragment thereof, and an immune checkpoint inhibitor may be usefully used for cancer prevention and treatment.

BRIEF DESCRIPTION OF DRAWINGS

FIG. 1 illustrates a schematic embodiment of a fusion protein dimer.

FIG. 2 illustrates a schematic view of a mechanism by which the fusion protein dimer acts in the lymph node.

FIG. 3 illustrates a schematic view of a mechanism by which the fusion protein dimer acts in the tumor microenvironment.

FIG. 4 illustrates a schematic view of the structure of the fusion protein. Here, each of GI101 and mGI101 is an embodiment of the fusion protein, and GI101C1, GI101C2, and mGI101C1 are comparative examples for comparison with activity of the fusion protein.

FIG. 5 illustrates various embodiments of the fusion protein. Human- and mouse-derived proteins may be combined to prepare a fusion protein. CD80 protein and IL-2 protein may be bound to each other via various linkers other than Fc.

FIG. 6 illustrates a result obtained by identifying the obtained fusion protein dimer (GI101) with SDS-PAGE.

FIG. 7 illustrates amounts of the fusion protein (GI101) depending on absorbance.

FIG. 8 illustrates a result obtained by analyzing the obtained fusion protein dimer (GI101) by size exclusion chromatography (SEC).

FIG. 9 illustrates a result obtained by identifying the obtained mGI101 fusion protein dimer with SDS-PAGE.

FIG. 10 illustrates results obtained by identifying the obtained GI101C1 fusion protein dimer with SDS-PAGE.

FIG. 11 illustrates results obtained by identifying the obtained GI101C2 fusion protein dimer with SDS-PAGE.

FIG. 12 illustrates a result obtained by identifying the obtained mGI101C1 fusion protein dimer with SDS-PAGE.

FIG. 13 illustrates results obtained by identifying the obtained GI102-M45 fusion protein dimer with SDS-PAGE.

FIG. 14 illustrates results obtained by identifying the obtained GI102-M61 fusion protein dimer with SDS-PAGE.

FIG. 15 illustrates results obtained by identifying the obtained GI102-M72 fusion protein dimer with SDS-PAGE.

FIG. 16 illustrates binding affinity between hCTLA4 and GI101.

FIG. 17 illustrates binding affinity between hPD-L1 and GI101.

FIG. 18 illustrates binding affinity between hPD-L1 and hPD-1.

FIG. 19 illustrates binding affinity between mCTLA4 and mGI101.

FIG. 20 illustrates binding affinity between mPD-L1 and mGI101.

FIG. 21 illustrates results obtained by identifying binding ability between GI-101 (hCD80-Fc-hIL-2v) and CTLA-4. It was identified that GI-101 (hCD80-Fc-hIL-2v) has high binding ability for CTLA-4.

FIG. 22 illustrates results obtained by identifying binding affinity between GI101 and IL-2Rα or IL-2Rβ.

FIG. 23 illustrates results obtained by identifying binding affinity between GI101 and IL-2Rα.

FIG. 24 illustrates results obtained by identifying binding affinity between GI101 and IL-2Rβ.

FIG. 25 illustrates results obtained by identifying binding affinity between IL-2Rα and GI102-M45.

FIG. 26 illustrates results obtained by identifying binding affinity between IL-2Rα and GI102-M61.

FIG. 27 illustrates results obtained by identifying binding affinity between IL-2Rα and GI102-M72.

FIG. 28 illustrates results obtained by identifying binding affinity between IL-2Rβ and GI102-M45.

FIG. 29 illustrates results obtained by identifying binding affinity between IL-2Rβ and GI102-M61.

FIG. 30 illustrates results obtained by identifying binding affinity between IL-2Rβ and GI102-M72.

FIGS. 31 and 32 illustrate results obtained by measuring amounts of IFN-γ secreted from cells when the cells are subjected to treatment with GI101, GI101C1, GI101C2, or IL-2 at respective concentrations and incubation is performed.

FIG. 33 illustrates results obtained by identifying effects of GI101, GI101C1, GI101C2, and IL-2 (Proleukin) on proliferation of CD8+ T cells.

FIG. 34 illustrates a schematic view of a mechanism by which GI101 acts on effector T cells.

FIG. 35 illustrates results obtained by identifying effects of GI101 and GI102 on proliferation of CD8+ T cells and CD4+ T cells. Here, (A) illustrates proportions of CD8+ T cells and CD4+ T cells, (B) illustrates proliferation capacity of CD8+ T cells, and (C) illustrates a proportion of CD4+/FoxP3+ Treg cells.

FIGS. 36 and 37 illustrate results obtained by identifying effects of GI101 and GI101w on proliferation of CD8+ T cells and NK cells.

FIGS. 38 and 39 illustrate results obtained by identifying an effect of GI101 on effector T cells.

FIG. 40 illustrates results obtained by identifying effects of mGI101 and mGI102-M61 on mouse immune cells.

FIGS. 41 and 42 illustrate results obtained by identifying an effect of GI101 on the inhibition of T cell activity by cancer cells expressing PD-L1 and CTLA-4.

FIG. 43 illustrates results obtained by identifying a tumor inhibitory effect of mGI101, depending on its dose, in mouse-derived colorectal cancer cell-transplanted mice.

FIG. 44 illustrates results obtained by identifying survival rate of mouse-derived colorectal cancer cell-transplanted mice having received mGI101.

FIG. 45 illustrates results obtained by identifying a tumor inhibitory effect of GI101 in mouse-derived colorectal cancer cell-transplanted mice.

FIG. 46 illustrates results obtained by subjecting mouse-derived colorectal cancer cell-transplanted mice to treatment with hIgG4, an anti-PD-1 antibody, or GI101, and then analyzing, with FACS, CD8+ T cells, IFN-γ T cells, CD4+ T cells, and Treg cells in cancer tissues.

FIG. 47 graphically illustrates results obtained by subjecting mouse-derived colorectal cancer cell-transplanted mice to treatment with hIgG4, an anti-PD-1 antibody, or GI101, and then analyzing, with FACS, CD8+ T cells, IFN-γ T cells, CD4+ T cells, and Treg cells in cancer tissues.

FIG. 48 illustrates results obtained by subjecting mouse-derived colorectal cancer cell-transplanted mice to treatment with hIgG4, an anti-PD-1 antibody, or GI101, and then analyzing, with FACS, macrophages in cancer tissues.

FIG. 49 graphically illustrates results obtained by subjecting mouse-derived colorectal cancer cell-transplanted mice to treatment with hIgG4, an anti-PD-1 antibody, or GI101, and then analyzing, with FACS, macrophages in cancer tissues.

FIG. 50 illustrates results obtained by subjecting mouse-derived colorectal cancer cell-transplanted mice to treatment with hIgG4, an anti-PD-1 antibody, or GI101, and then analyzing, with FACS, dendritic cells in cancer tissues.

FIG. 51 graphically illustrates results obtained by subjecting mouse-derived colorectal cancer cell-transplanted mice to treatment with hIgG4, an anti-PD-1 antibody, or GI101, and then analyzing, with FACS, dendritic cells in cancer tissues.

FIG. 52 illustrates results obtained by identifying a tumor inhibitory effect of GI101 in mouse-derived lung cancer cell-transplanted mice.

FIG. 53 graphically illustrates results obtained by subjecting mouse-derived lung cancer cell-transplanted mice to treatment with hIgG4, an anti-PD-1 antibody, or GI101, and then analyzing, with FACS, CD8+ T cells, IFN-γ T cells, CD4+ T cells, and Treg cells in cancer tissues.

FIG. 54 graphically illustrates results obtained by subjecting mouse-derived lung cancer cell-transplanted mice to treatment with hIgG4, an anti-PD-1 antibody, or GI101, and then analyzing, with FACS, macrophages in cancer tissues.

FIG. 55 graphically illustrates results obtained by subjecting mouse-derived lung cancer cell-transplanted mice to treatment with hIgG4, an anti-PD-1 antibody, or GI101, and then analyzing, with FACS, dendritic cells in cancer tissues.

FIG. 56 illustrates results obtained by identifying a tumor inhibitory effect of mGI102-M61 in mouse-derived colorectal cancer cell-transplanted mice.

FIG. 57 illustrates results obtained by analyzing survival rate of mouse-derived colorectal cancer cell-transplanted mice having received mGI102-M61.

FIG. 58 illustrates results obtained by identifying a tumor inhibitory effect of mGI101 in mouse-derived colorectal cancer cell-transplanted mice.

FIG. 59 illustrates a tumor inhibition rate of mGI101 in mouse-derived colorectal cancer cell-transplanted mice.

FIG. 60 shows a graph of tumor growth when GI101 and Keytruda are used in combination in human-derived breast cancer cell transplanted mice. Tumor growth was inhibited in the GI101 or Keytruda alone treatment groups compared to the control group (hIgG4). Tumor growth was inhibited in the GI101 and Keytruda combined treatment group compared to the control group. Tumor growth was inhibited in the GI101 and Keytruda combined treatment group compared to the GI101 or Keytruda alone treatment groups.

FIG. 61 shows tumor growth inhibition rate when GI-101 and Keytruda are used in combination in human-derived breast cancer cell transplanted mice. The IgG4 treatment group had 2 mice having tumor growth inhibition rate of 30% or more, 1 mouse having tumor growth inhibition rate of 50% or more, and 1 mouse having tumor growth inhibition rate of 80%. The GI101 treatment group had 5 mice having tumor growth inhibition rate of 30% or more, 5 mice having tumor growth inhibition rate of 50% or more, and 2 mice having tumor growth inhibition rate of 80%. The Keytruda treatment group had 7 mice having tumor growth inhibition rate of 30% or more, 5 mice having tumor growth inhibition rate of 50% or more, and 3 mice having tumor growth inhibition rate of 80%. The GI101 and Keytruda combined treatment group had 8 mice having tumor growth inhibition rate of 30% or more, 8 mice having tumor growth inhibition rate of 50% or more, and 6 mice having tumor growth inhibition rate of 80%.

FIG. 62 shows the degree of tumor growth of individual experimental animals in each treatment group when GI101 and Keytruda are used in combination in human-derived breast cancer cell transplanted mice.

FIG. 63 shows the degree of tumor growth of individual experimental animals in hIgG4 treatment group in human-derived breast cancer cell transplanted mice.

FIG. 64 shows the degree of tumor growth of individual experimental animals in the GI101 treatment group in human-derived breast cancer cell transplanted mice.

FIG. 65 shows the degree of tumor growth of individual experimental animals in the Keytruda treatment group in human-derived breast cancer cell transplanted mice.

FIG. 66 shows the degree of tumor growth of individual experimental animals in the GI101 and Keytruda combined treatment group in human-derived breast cancer cell transplanted mice.

FIG. 67 shows the graph of tumor growth when mGI101 and an anti-PD-1 antibody are administered in combination in rodent-derived colorectal cancer cell transplanted mice.

FIG. 68 shows the tumor growth inhibition rate when mGI101 and an anti-PD-1 antibody are administered in combination in rodent-derived colorectal cancer cells transplanted mice.

FIG. 69 shows the degree of tumor growth of individual experimental animals in each treatment group when mGI101 and an anti-PD-1 antibody are administered in combination in rodent-derived colorectal cancer cells transplanted mice.

FIG. 70 shows the degree of tumor growth of individual experimental animals in the hIgG4 treatment group in rodent-derived colorectal cancer cells transplanted mice.

FIG. 71 shows the degree of tumor growth of individual experimental animals in the mGI101 treatment group in rodent-derived colorectal cancer cells transplanted mice.

FIG. 72 shows the degree of tumor growth of individual experimental animals in the anti-PD-1 antibody treatment group in rodent-derived colorectal cancer cells transplanted mice.

FIG. 73 shows the degree of tumor growth of individual experimental animals in the mGI101 and anti-PD-1 antibody combined treatment group is administered in rodent-derived colorectal cancer cells transplanted mice.

FIG. 74 shows the degree of tumor growth of individual experimental animals when rodent-derived colorectal cancer cells were re-injected to the experimental animals which showed complete remission in the mGI101 and anti-PD-1 antibody combined treatment group in rodent-derived colorectal cancer cells transplanted mice.

FIG. 75 shows a graph of tumor growth when mGI101 and an anti-PD-L1 antibody are administered in combination in rodent-derived colorectal cancer cells transplanted mice.

FIG. 76 shows a graph of tumor growth when mGI101 and an anti-TIGIT antibody are administered in combination in rodent-derived colorectal cancer cells transplanted mice.

BEST MODE FOR CARRYING OUT THE INVENTION

An aspect of the present invention provides a pharmaceutical composition for treating cancer containing, as active ingredients, a fusion protein dimer comprising an IL-2 protein or a variant thereof and a CD80 protein or a fragment thereof, and an immune checkpoint inhibitor.

Immune Checkpoint Inhibitor

As used herein, the term "immune checkpoint" refers to an intracellular signaling system that maintains self-tolerance and protects tissues from excessive immune responses that cause damage. The immune checkpoint proteins is a cell membrane protein that regulates immune checkpoint and can inhibit differentiation, proliferation, and activity of immune cells. Specifically, the immune checkpoint protein is expressed in activated T cells so as to function to reduce T cell proliferation, cytokine secretion, and cytotoxicity, and inhibit excessive activity of T cells. Some immune checkpoints are known to be one of the main mechanisms of tumor cells resulting in immune evasion. Therefore, an "immune checkpoint inhibitor" targets immune checkpoint proteins to inhibit or block the immune checkpoints and increase activation of T cells, thereby enhancing antitumor immunity, and thus exhibiting an anticancer effect. In addition to advantages of having fewer side effects such as vomiting and hair loss than conventional cytotoxic anticancer agents, and a greater therapeutic effect, immune checkpoint inhibitors are known to have a long-lasting therapeutic effect even after drug administration is discontinued because they take advantage of an immune response system with excellent memory capacity.

Specifically, an immune checkpoint inhibitor may target CTLA-4, PD-1, PD-L1, PD-L2, B7-H4, HVEM (Herpesvirus entry mediator), BTLA, TIM3, GAL9, LAG3, VISTA, KIR or TIGIT.

In particular, the immune checkpoint inhibitor may include, but not be limited to, an anti-CTLA-4 antibody, an anti-PD-1 antibody, an anti-PD-L1 antibody, an anti-PD-L2 antibody, an anti-B7-H4 antibody, an anti-HVEM antibody, an anti-BTLA antibody, an anti-TIM3 antibody, an anti- GAL9 antibody, an anti-LAG3 antibody, an anti-VISTA antibody, an anti-KIR antibody and an anti-TIGIT antibody.

As used herein, the term "cytotoxic T-lymphocyte-associated antigen 4 (CTLA-4)" is referred to as CD152, and is expressed on the membrane surface of activated T cells. CTLA-4 binds to CD80 (B7-1) and CD86 (B7-2) of antigen presenting cells and inhibits T cell activity. CTLA-4 inhibitors may be ipilimumab (YERVOY®) and tremelimumab.

As used herein, the term "programmed cell death protein 1 (PD-1)" is referred to as CD279, and is expressed on the surface of activated T cells. PD-1 reacts with a protein on the surface of cancer cells, PD-L1 (B7-H1) and PD-L2 (B7-DC), and inhibits T-cell activity, growth factor, and cytokine production which are mediated by TCR (T cell receptor) and CD28 to induce negative signaling. The PD-1 inhibitor may be, for example, pembrolizumab (Keytruda®), MK-3475, nivolumab (Opdivo®), cemiplimab (Libtayo®), JTX-4014, spartalizumab, camrelizumab, sintilimab, tislelizumab, toripalimab, dostarlimab, INCMGA00012, AMP-224, and AMP-514.

As used herein, the term "programmed death-ligand 1 (PD-L1)" is referred to as CD274 or B7-H1, and is a protein presented on the surface of cancer cells or on hematopoietic cells. PD-L1 presented on the cancer surface can bind to PD-1 presented on the surface of T cells. The PD-L1 inhibitor may be, for example, atezolizumab, avelumab (Bavencio®), durvalumab (Imfinzi®), KN035, CK-301, AUNP12, CA-170, and BMS-986189.

As used herein, the term "B7-H4" is referred to as V-set domain-containing T-cell activation inhibitor 1 (VTCN1), and is expressed on the membrane surface of antigen-presenting cells. B7-H4 binds to CD28 protein of T cells and inhibits activity, growth, and cytokine production of T cells to negatively regulate T-cell mediated immune responses.

As used herein, the term "herpesvirus entry mediator (HVEM)" is referred to as CD270, and is also known as tumor necrosis factor receptor superfamily member 14 (TNFRSF14). HVEM is expressed on the membrane surface of various immune cells including T cells, and binds to various partner proteins to regulate inflammation and immune responses. When HVEM binds to B and T lymphocyte attenuator (BTLA, CD272) or CD160 of T cells, immune activity of T cells is inhibited. On the other hand, when HVEM binds to TNFSF14 (LIGHT), HVEM induces dendritic cell maturation, T cell proliferation and cytokine production to activate inflammation and immune responses.

As used herein, the term "T cell membrane protein 3 (TIM3)" is also referred to as hepatitis A virus cellular receptor 2 (HAVCR2), and is expressed in various immune cells. When TIM3 is activated by binding to a water-soluble protein GAL9 (galectin 9), intracellular calcium influx is increased to induce apoptosis of T cells, which in turn causes immune tolerance. In addition, with GAL9, TIM3 binds to a cell adhesion molecule 1 (CEACAM1) which is a cell surface protein to inhibit immune activity of T cells, and binds to high mobility group protein 1 (HMGB1) or phospatidyl serine (PTdSer) which is a water-soluble protein to inhibit immune activity. TIM3 inhibitors may be LY3321367, MBG453, and TSR-022.

As used herein, the term "lymphocyte activation gene 3 (LAG3)" is referred to as CD223, and binds to a major histocompatibility complex (MHC) class II to inhibit proliferation and activity of T cells. LAG3 inhibitors may be IMP321, relatlimab, and GSK2831781.

As used herein, the term "V-domain Ig suppressor of T cell activation (VISTA)" belongs to B7 family (B7-H5), and is expressed in various immune cells to inhibit proliferation, activity, and cytokine production of T cells. VISTA inhibitors may be JNJ-63723283.

As used herein, the term "killer cell immunoglobulin-like receptor (KIR)" is a membrane-bound protein expressed in NK cells and T cells, and is a family protein having genetic diversity and homology. Among them, KIR2DL1, KIR2DL2/L3, KIR3DL1, and KIR3DL2 may bind to MHC class I to inhibit cell immune activity of NK cells.

As used herein, the term "T cell immunoglobulin and ITIM domain (TIGIT)" is a membrane-bound protein expressed on the surface of NK cells and T cells and may bind to CD155, CD112 and CD113 to inhibit immune activity.

A Fusion Protein Comprising an IL-2 Protein and a CD80 Protein, and a Dimer Thereof As used herein, the term "IL-2" or "interleukin-2", unless otherwise stated, refers to any wild-type IL-2 obtained from any vertebrate source, including mammals, for example, primates (such as humans) and rodents (such as mice and rats). IL-2 may be obtained from animal cells, and also includes one obtained from recombinant cells capable of producing IL-2. In addition, IL-2 may be wild-type IL-2 or a variant thereof.

In the present specification, IL-2 or a variant thereof may be collectively expressed by the term "IL-2 protein" or "IL-2 polypeptide." IL-2, an IL-2 protein, an IL-2 polypeptide, and an IL-2 variant specifically bind to, for example, an IL-2 receptor. This specific binding may be identified by methods known to those skilled in the art.

An embodiment of IL-2 may have the amino acid sequence of SEQ ID NO: 35 or SEQ ID NO: 36. Here, IL-2 may also be in a mature form. Specifically, the mature IL-2 may not contain a signal sequence, and may have the amino acid sequence of SEQ ID NO: 10. Here, IL-2 may be used under a concept encompassing a fragment of wild-type IL-2 in which a portion of N-terminus or C-terminus of the wild-type IL-2 is truncated.

In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from N-terminus of a protein having the amino acid sequence of SEQ ID NO: 35 or SEQ ID NO: 36. In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from C-terminus of a protein having the amino acid sequence of SEQ ID NO: 35 or SEQ ID NO: 36.

As used herein, the term "IL-2 variant" refers to a form in which a portion of amino acids in the full-length IL-2 or the above-described fragment of IL-2 is substituted. That is, an IL-2 variant may have an amino acid sequence different from wild-type IL-2 or a fragment thereof. However, an IL-2 variant may have activity equivalent or similar to the wild-type IL-2. Here, "IL-2 activity" may, for example, refer to specific binding to an IL-2 receptor, which specific binding can be measured by methods known to those skilled in the art.

Specifically, an IL-2 variant may be obtained by substitution of a portion of amino acids in the wild-type IL-2. An embodiment of the IL-2 variant obtained by amino acid substitution may be obtained by substitution of at least one of the $38^{th}$, $42^{nd}$, $45^{th}$, $16^{st}$, and $72^{nd}$ amino acids in the amino acid sequence of SEQ ID NO: 10.

Specifically, the IL-2 variant may be obtained by substitution of at least one of the $38^{th}$, $42^{nd}$, $45^{th}$, $61^{st}$, or $72^{nd}$ amino acid in the amino acid sequence of SEQ ID NO: 10 with another amino acid. In addition, when IL-2 is in a form in which a portion of N-terminus in the amino acid sequence of SEQ ID NO: 35 is truncated, the amino acid at a position complementarily corresponding to that in the amino acid sequence of SEQ ID NO: 10 may be substituted with another amino acid. For example, when IL-2 has the amino acid sequence of SEQ ID NO: 35, its IL-2 variant may be obtained by substitution of at least one of $58^{th}$, $62^{nd}$, $65^{th}$, $81^{st}$, or $92^{nd}$ amino acid in the amino acid sequence of SEQ ID NO: 35 with another amino acid. These amino acid residues correspond to the $38^{th}$, $42^{nd}$, $45^{th}$, $61^{st}$, and $72^{nd}$ amino acid residues in the amino acid sequence of SEQ ID NO: 10, respectively. According to an embodiment, one, two, three, four, five, six, seven, eight, nine, or ten amino acids may be substituted as long as such IL-2 variant maintains IL-2 activity. According to another embodiment, one to five amino acids may be substituted.

In an embodiment, an IL-2 variant may be in a form in which two amino acids are substituted. Specifically, the IL-2 variant may be obtained by substitution of the $38^{th}$ and $42^{nd}$ amino acids in the amino acid sequence of SEQ ID NO: 10. In addition, in an embodiment, the IL-2 variant may be obtained by substitution of the $38^{th}$ and $45^{th}$ amino acids in the amino acid sequence of SEQ ID NO: 10. In addition, in an embodiment, the IL-2 variant may be obtained by substitution of the $38^{th}$ and $61^{st}$ amino acids in the amino acid sequence of SEQ ID NO: 10. In addition, in an embodiment, the IL-2 variant may be obtained by substitution of the $38^{th}$ and $72^{nd}$ amino acids in the amino acid sequence of SEQ ID NO: 10. In addition, in an embodiment, the IL-2 variant may be obtained by substitution of the $42^{nd}$ and $45^{th}$ amino acids in the amino acid sequence of SEQ ID NO: 10. In addition, in an embodiment, the IL-2 variant may be obtained by substitution of the $42^{nd}$ and $61^{st}$ amino acids in the amino acid sequence of SEQ ID NO: 10. In addition, in an embodiment, the IL-2 variant may be obtained by substitution of the $42^{nd}$ and $72^{nd}$ amino acids in the amino acid sequence of SEQ ID NO: 10. In addition, in an embodiment, the IL-2 variant may be obtained by substitution of the $45^{th}$ and $61^{st}$ amino acids in the amino acid sequence of SEQ ID NO: 10. In addition, in an embodiment, the IL-2 variant may be obtained by substitution of the $45^{th}$ and $72^{nd}$ amino acids in the amino acid sequence of SEQ ID NO: 10. In addition, in an embodiment, the IL-2 variant may be obtained by substitution of the $61^{st}$ and $72^{nd}$ amino acids in the amino acid sequence of SEQ ID NO: 10.

Furthermore, an IL-2 variant may be in a form in which three amino acids are substituted. Specifically, the IL-2 variant may be obtained by substitution of the $38^{th}$, $42^{nd}$, and $45^{th}$ amino acids in the amino acid sequence of SEQ ID NO: 10. In addition, in an embodiment, the IL-2 variant may be obtained by substitution of the $38^{th}$, $42^{nd}$, and $61^{st}$ amino acids in the amino acid sequence of SEQ ID NO: 10. In addition, in an embodiment, the IL-2 variant may be obtained by substitution of the $38^{th}$, $42^{nd}$, and $72^{nd}$ amino acids in the amino acid sequence of SEQ ID NO: 10. In addition, in an embodiment, the IL-2 variant may be obtained by substitution of the $38^{th}$, $45^{th}$, and $61^{st}$ amino acids in the amino acid sequence of SEQ ID NO: 10. In addition, in an embodiment, the IL-2 variant may be obtained by substitution of the $38^{th}$, $45^{th}$, and $72^{nd}$ amino acids in the amino acid sequence of SEQ ID NO: 10. In addition, in an embodiment, the IL-2 variant may be obtained by substitution of the $38^{st}$, $61^{st}$, and $72^{nd}$ amino acids in the amino acid sequence of SEQ ID NO: 10. In addition, in an embodiment, the IL-2 variant may be obtained by substitution of the $42^{nd}$, $45^{th}$, and $61^{st}$ amino acids in the amino acid sequence of SEQ ID NO: 10. In addition, in an embodiment, the IL-2 variant may be obtained by substitution of the $42^{nd}$, $45^{th}$, and $72^{nd}$ amino acids in the amino acid sequence of SEQ ID NO: 10. In addition, in an embodiment, the IL-2 variant may be obtained by substitution of the $45^{th}$, $61^{st}$, and $72^{nd}$ amino acids in the amino acid sequence of SEQ ID NO: 10.

In addition, an IL-2 variant may be in a form in which four amino acids are substituted. Specifically, the IL-2 variant may be obtained by substitution of the $38^{th}$, $42^{nd}$, $45^{th}$, and $61^{st}$ amino acids in the amino acid sequence of SEQ ID NO: 10. In addition, in an embodiment, the IL-2 variant may be obtained by substitution of the $38^{th}$, $42^{nd}$, $45^{th}$, and $72^{nd}$ amino acids in the amino acid sequence of SEQ ID NO: 10. In addition, in an embodiment, the IL-2 variant may be obtained by substitution of the $38^{th}$, $45^{th}$, $61^{st}$ and $72^{nd}$ amino acids in the amino acid sequence of SEQ ID NO: 10. In addition, in an embodiment, the IL-2 variant may be obtained by substitution of the $38^{th}$, $42^{nd}$, $61^{st}$, and $72^{nd}$ amino acids in the amino acid sequence of SEQ ID NO: 10. In addition, in an embodiment, the IL-2 variant may be obtained by substitution of $42^{nd}$, $45^{th}$, $61^{st}$ and $72^{nd}$ amino acids in the amino acid sequence of SEQ ID NO: 10.

Furthermore, an IL-2 variant may be in a form in which five amino acids are substituted. Specifically, the IL-2 variant may be obtained by substitution of each of the $38^{th}$, $42^{nd}$, $45^{th}$, $61^{st}$, and $72^{nd}$ amino acids in the amino acid sequence of SEQ ID NO: 10 with another amino acid.

Here, the "another amino acid" introduced by the substitution may be any one selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. However, regarding amino acid substitution for the IL-2 variant, in the amino acid sequence of SEQ ID NO: 10, the $38^{th}$ amino acid cannot be substituted with arginine, the $42^{nd}$ amino acid cannot be substituted with phenylalanine, the $45^{th}$ amino acid cannot be substituted with tyrosine, the $61^{st}$ amino acid cannot be substituted with glutamic acid, and the $72^{nd}$ amino acid cannot be substituted with leucine.

Regarding amino acid substitution for an IL-2 variant, in the amino acid sequence of SEQ ID NO: 10, the $38^{th}$ amino acid, arginine, may be substituted with an amino acid other than arginine. Preferably, regarding amino acid substitution for an IL-2 variant, in the amino acid sequence of SEQ ID NO: 10, the $38^{th}$ amino acid, arginine, may be substituted with alanine (R38A).

Regarding amino acid substitution for an IL-2 variant, in the amino acid sequence of SEQ ID NO: 10, the $42^{nd}$ amino acid, phenylalanine, may be substituted with an amino acid other than phenylalanine. Preferably, regarding amino acid substitution for an IL-2 variant, in the amino acid sequence of SEQ ID NO: 10, the $42^{nd}$ amino acid, phenylalanine, may be substituted with alanine (F42A).

Regarding amino acid substitution for an IL-2 variant, in the amino acid sequence of SEQ ID NO: 10, the $45^{th}$ amino acid, tyrosine, may be substituted with an amino acid other than tyrosine. Preferably, regarding amino acid substitution for an IL-2 variant, in the amino acid sequence of SEQ ID NO: 10, the $45^{th}$ amino acid, tyrosine, may be substituted with alanine (Y45A).

Regarding amino acid substitution for an IL-2 variant, in the amino acid sequence of SEQ ID NO: 10, the $61^{st}$ amino acid, glutamic acid, may be substituted with an amino acid other than glutamic acid. Preferably, regarding amino acid substitution for an IL-2 variant, in the amino acid sequence of SEQ ID NO: 10, the 61$^{st}$ amino acid, glutamic acid, may be substituted with arginine (E61R).

Regarding amino acid substitution for an IL-2 variant, in the amino acid sequence of SEQ ID NO: 10, the 72$^{nd}$ amino acid, leucine, may be substituted with an amino acid other than leucine. Preferably, regarding amino acid substitution for an IL-2 variant, in the amino acid sequence of SEQ ID NO: 10, the 72$^{nd}$ amino acid, leucine, may be substituted with glycine (L72G).

Specifically, an IL-2 variant may be obtained by at least one substitution selected from the group consisting of R38A, F42A, Y45A, E61R, and L72G, in the amino acid sequence of SEQ ID NO: 10.

Specifically, an IL-2 variant may be obtained by amino acid substitutions at two, three, four, or five positions among the positions selected from the group consisting of R38A, F42A, Y45A, E61R, and L72G.

In addition, an IL-2 variant may be in a form in which two amino acids are substituted. Specifically, an IL-2 variant may be obtained by the substitutions, R38A and F42A. In addition, in an embodiment, an IL-2 variant may be obtained by the substitutions, R38A and Y45A. In addition, in an embodiment, an IL-2 variant may be obtained by the substitutions, R38A and E61R. In addition, in an embodiment, an IL-2 variant may be obtained by the substitutions, R38A and L72G. In addition, in an embodiment, an IL-2 variant may be obtained by the substitutions, F42A and Y45A. In addition, in an embodiment, an IL-2 variant may be obtained by the substitutions, F42A and E61R. In addition, in an embodiment, an IL-2 variant may be obtained by the substitutions, F42A and L72G. In addition, in an embodiment, an IL-2 variant may be obtained by the substitutions, E61R and L72G.

Furthermore, an IL-2 variant may be in a form in which three amino acids are substituted. Specifically, an IL-2 variant may be obtained by the substitutions, R38A, F42A, and Y45A. In addition, in an embodiment, an IL-2 variant may be obtained by the substitutions, R38A, F42A, and E61R. In addition, in an embodiment, an IL-2 variant may be obtained by the substitutions, R38A, F42A, and L72G. In addition, in an embodiment, an IL-2 variant may be obtained by the substitutions, R38A, Y45A, and E61R. In addition, in an embodiment, an IL-2 variant may be obtained by the substitutions, R38A, Y45A, and L72G. In addition, in an embodiment, an IL-2 variant may be obtained by the substitutions, F42A, Y45A, and E61R. In addition, in an embodiment, an IL-2 variant may be obtained by the substitutions, F42A, Y45A, and L72G. In addition, in an embodiment, an IL-2 variant may be obtained by the substitutions, F42A, E61R, and L72G. In addition, in an embodiment, an IL-2 variant may be obtained by the substitutions, Y45A, E61R, and L72G.

In addition, an IL-2 variant may be in a form in which four amino acids are substituted. Specifically, an IL-2 variant may be obtained by the substitutions, R38A, F42A, Y45A, and E61R. In addition, in an embodiment, an IL-2 variant may be obtained by the substitutions, R38A, F42A, Y45A, and L72G. In addition, in an embodiment, an IL-2 variant may be obtained by the substitutions, R38A, F42A, E61R, and L72G. In addition, in an embodiment, an IL-2 variant may be obtained by the substitutions, R38A, Y45A, E61R, and L72G. In addition, in an embodiment, an IL-2 variant may be obtained by the substitutions, F42A, Y45A, E61R, and L72G.

Furthermore, an IL-2 variant may be obtained by the substitutions, R38A, F42A, Y45A, E61R, and L72G.

Preferably, an embodiment of the IL-2 variant may contain which are any one selected from the following substitution combinations (a) to (d) in the amino acid sequence of SEQ ID NO: 10:

(a) R38A/F42A
(b) R38A/F42A/Y45A
(c) R38A/F42A/E61R
(d) R38A/F42A/L72G

Here, when IL-2 has the amino acid sequence of SEQ ID NO: 35, an amino acid substitution may be present at a position complementarily corresponding to that in the amino acid sequence of SEQ ID NO: 10. In addition, even when IL-2 is a fragment of the amino acid sequence of SEQ ID NO: 35, an amino acid substitution may be present at a position complementarily corresponding to that in the amino acid sequence of SEQ ID NO: 10.

Specifically, an IL-2 variant may have the amino acid sequence of SEQ ID NO: 6, 22, 23, or 24.

In addition, an IL-2 variant may be characterized by having low in vivo toxicity. Here, the low in vivo toxicity may be a side effect caused by binding of IL-2 to the IL-2 receptor alpha chain (IL-2Rα). Various IL-2 variants have been developed to ameliorate the side effect caused by binding of IL-2 to IL-2Rα, and such IL-2 variants may be those disclosed in U.S. Pat. No. 5,229,109 and Korean Patent No. 1667096. In particular, IL-2 variants described in the present application have low binding ability for the IL-2 receptor alpha chain (IL-2Rα) and thus have lower in vivo toxicity than the wild-type IL-2.

As used herein, the term "CD80", also called "B7-1", is a membrane protein present in dendritic cells, activated B cells, and monocytes. CD80 provides co-stimulatory signals essential for activation and survival of T cells. CD80 is known as a ligand for the two different proteins, CD28 and CTLA-4, present on the surface of T cells. CD80 is composed of 288 amino acids, and may specifically have the amino acid sequence of SEQ ID NO: 11. In addition, as used herein, the term "CD80 protein" refers to the full-length CD80 or a CD80 fragment.

As used herein, the term "CD80 fragment" refers to a cleaved form of CD80. In addition, the CD80 fragment may be an extracellular domain of CD80. An embodiment of the CD80 fragment may be obtained by elimination of the 1$^{st}$ to 34$^{th}$ amino acids from N-terminus which are a signal sequence of CD80. Specifically, an embodiment of the CD80 fragment may be a protein composed of the 35$^{th}$ to 288$^{th}$ amino acids in SEQ ID NO: 11. In addition, an embodiment of the CD80 fragment may be a protein composed of the 35$^{th}$ to 242$^{nd}$ amino acids in SEQ ID NO: 11. In addition, an embodiment of the CD80 fragment may be a protein composed of the 35$^{th}$ to 232$^{nd}$ amino acids in SEQ ID NO: 11. In addition, an embodiment of the CD80 fragment may be a protein composed of the 35$^{th}$ to 139$^{th}$ amino acids in SEQ ID NO: 11. In addition, an embodiment of the CD80 fragment may be a protein composed of the 142$^{nd}$ to 242$^{nd}$ amino acids in SEQ ID NO: 11. In an embodiment, a CD80 fragment may have the amino acid sequence of SEQ ID NO: 2.

In addition, the IL-2 protein and the CD80 protein may be attached to each other via a linker or a carrier. Specifically, the IL-2 or a variant thereof and the CD80 (B7-1) or a fragment thereof may be attached to each other via a linker or a carrier. In the present description, the linker and the carrier may be used interchangeably.

The linker links two proteins. An embodiment of the linker may include 1 to 50 amino acids, albumin or a fragment thereof, an Fc domain of an immunoglobulin, or the like. Here, the Fc domain of immunoglobulin refers to a protein that contains heavy chain constant region 2 (CH2) and heavy chain constant region 3 (CH3) of an immunoglobulin, and does not contain heavy and light chain variable regions and light chain constant region 1 (CH1) of an immunoglobulin. The immunoglobulin may be IgG, IgA, IgE, IgD, or IgM, and may preferably be IgG4. Here, Fc domain of wild-type immunoglobulin G4 may have the amino acid sequence of SEQ ID NO: 4.

In addition, the Fc domain of an immunoglobulin may be an Fc domain variant as well as wild-type Fc domain. In addition, as used herein, the term "Fc domain variant" may refer to a form which is different from the wild-type Fc domain in terms of glycosylation pattern, has a high glycosylation as compared with the wild-type Fc domain, or has a low glycosylation as compared with the wild-type Fc domain, or a deglycosylated form. In addition, an aglycosylated Fc domain is included therein. The Fc domain or a variant thereof may be adapted to have an adjusted number of sialic acids, fucosylations, or glycosylations, through culture conditions or genetic manipulation of a host.

In addition, glycosylation of the Fc domain of an immunoglobulin may be modified by conventional methods such as chemical methods, enzymatic methods, and genetic engineering methods using microorganisms. In addition, the Fc domain variant may be in a mixed form of respective Fc regions of immunoglobulins, IgG, IgA, IgE, IgD, and IgM. In addition, the Fc domain variant may be in a form in which some amino acids of the Fc domain are substituted with other amino acids. An embodiment of the Fc domain variant may have the amino acid sequence of SEQ ID NO: 12.

The fusion protein may have a structure in which, using an Fc domain as a linker (or carrier), a CD80 protein and an IL-2 protein, or an IL-2 protein and a CD80 protein are linked to N-terminus and C-terminus of the linker or carrier, respectively. Linkage between N-terminus or C-terminus of the Fc domain and CD-80 or IL-2 may optionally be achieved by a linker peptide.

Specifically, a fusion protein may consist of the following structural formula (I) or (II):

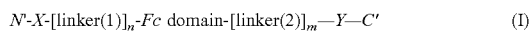

$N'$-$X$-[linker(1)]$_n$-Fc domain-[linker(2)]$_m$—$Y$—$C'$ (I)

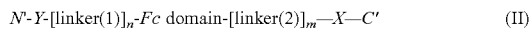

$N'$-$Y$-[linker(1)]$_n$-Fc domain-[linker(2)]$_m$—$X$—$C'$ (II)

Here, in the structural formulas (I) and (II),
N' is the N-terminus of the fusion protein,
C' is the C-terminus of the fusion protein,
X is a CD80 protein,
Y is an IL-2 protein,
the linkers (1) and (2) are peptide linkers, and
n and m are each independently 0 or 1.

Preferably, the fusion protein may consist of the structural formula (I). The IL-2 protein is as described above. In addition, the CD80 protein is as described above. According to an embodiment, the IL-2 protein may be an IL-2 variant with one to five amino acid substitutions as compared with the wild-type IL-2. The CD80 protein may be a fragment obtained by truncation of up to about 34 contiguous amino acid residues from the N-terminus or C-terminus of the wild-type CD80. Alternatively, the CD protein may be an extracellular immunoglobulin-like domain having the activity of binding to the T cell surface receptors CTLA-4 and CD28.

Specifically, the fusion protein may have the amino acid sequence of SEQ ID NO: 9, 26, 28, or 30. According to another embodiment, the fusion protein includes a polypeptide having a sequence identity of 85%, 86%, 87%, 88%, 89%, 90%, 91%, 92%, 93%, 94%, 95%, 96%, 97%, 98%, 99%, or 100% to the amino acid sequence of SEQ ID NO: 9, 26, 28, or 30. Here, the identity is, for example, percent homology, and may be determined through homology comparison software such as BlastN software of the National Center of Biotechnology Information (NCBI).

The peptide linker (1) may be included between the CD80 protein and the Fc domain. The peptide linker (1) may consist of 5 to 80 contiguous amino acids, 20 to 60 contiguous amino acids, 25 to 50 contiguous amino acids, or 30 to 40 contiguous amino acids. In an embodiment, the peptide linker (1) may consist of 30 amino acids. In addition, the peptide linker (1) may contain at least one cysteine. Specifically, the peptide linker (1) may contain one, two, or three cysteines. In addition, the peptide linker (1) may be derived from the hinge of an immunoglobulin. In an embodiment, the peptide linker (1) may be a peptide linker consisting of the amino acid sequence of SEQ ID NO: 3.

The peptide linker (2) may consist of 1 to 50 contiguous amino acids, 3 to 30 contiguous amino acids, or 5 to 15 contiguous amino acids. In an embodiment, the peptide linker (2) may be (G4S)$_n$ (where n is an integer of 1 to 10). Here, in (G4S)$_n$, n may be 1, 2, 3, 4, 5, 6, 7, 8, 9, or 10. In an embodiment, the peptide linker (2) may be a peptide linker consisting of the amino acid sequence of SEQ ID NO: 5.

In another aspect of the present invention, there is provided a dimer obtained by binding of two fusion proteins, each of which comprises an IL-2 protein and a CD80 protein. The fusion protein comprising IL-2 or a variant thereof and CD80 or a fragment thereof is as described above.

Here, the binding between the fusion proteins constituting the dimer may be achieved by, but is not limited to, a disulfide bond formed by cysteines present in the linker. The fusion proteins constituting the dimer may be the same or different fusion proteins from each other. Preferably, the dimer may be a homodimer. An embodiment of the fusion protein constituting the dimer may be a protein having the amino acid sequence of SEQ ID NO: 9.

A pharmaceutical composition of the present invention containing, as active ingredients, a fusion protein dimer comprising an IL-2 protein or a variant thereof and a CD80 protein or a fragment thereof, and an immune checkpoint inhibitor show an efficacy for preventing or treating cancer.

The cancer may be selected from the group consisting of gastric cancer, liver cancer, lung cancer, colorectal cancer, breast cancer, prostate cancer, ovarian cancer, pancreatic cancer, cervical cancer, thyroid cancer, laryngeal cancer, acute myeloid leukemia, brain tumor, neuroblastoma, retinoblastoma, head and neck cancer, salivary gland cancer, and lymphoma.

A preferred dose of the pharmaceutical composition varies depending on the patient's condition and body weight, severity of disease, form of drug, route and duration of administration and may be appropriately selected by those skilled in the art. In the pharmaceutical composition for treating or preventing cancer of the present invention, the active ingredient may be contained in any amount (effective amount) depending on application, dosage form, blending purpose, and the like, as long as the active ingredient can exhibit an anticancer activity. A conventional effective amount thereof will be determined within a range of 0.001% to 20.0% by weight, based on the total weight of the composition. Here, the term "effective amount" refers to an amount of an active ingredient capable of inducing an anticancer effect. Such an effective amount can be experimentally determined within the scope of common knowledge of those skilled in the art.

As used herein, the term "treatment" may be used to mean both therapeutic and prophylactic treatment. Here, prophylaxis may be used to mean that a pathological condition or disease of an individual is alleviated or mitigated. In an embodiment, the term "treatment" includes both application or any form of administration for treating a disease in a mammal, including a human. In addition, the term includes inhibiting or slowing down a disease or disease progression; and includes meanings of restoring or repairing impaired or lost function so that a disease is partially or completely alleviated; stimulating inefficient processes; or alleviating a serious disease.

As used herein, the term "efficacy" refers to capacity that can be determined by one or parameters, for example, survival or disease-free survival over a certain period of time such as one year, five years, or ten years. In addition, the parameter may include inhibition of size of at least one tumor in an individual.

Pharmacokinetic parameters such as bioavailability and underlying parameters such as clearance rate may also affect efficacy. Thus, "enhanced efficacy" (for example, improvement in efficacy) may be due to enhanced pharmacokinetic parameters and improved efficacy, which may be measured by comparing clearance rate and tumor growth in test animals or human subjects, or by comparing parameters such as survival, recurrence, or disease-free survival.

As used herein, the term "therapeutically effective amount" or "pharmaceutically effective amount" refers to an amount of a compound or composition effective to prevent or treat the disease in question, which is sufficient to treat the disease at a reasonable benefit/risk ratio applicable to medical treatment and does not cause adverse effects. A level of the effective amount may be determined depending on factors including the patient's health condition, type and severity of disease, activity of drug, the patient's sensitivity to drug, mode of administration, time of administration, route of administration and excretion rate, duration of treatment, formulation or simultaneously used drugs, and other factors well known in the medical field. In an embodiment, the therapeutically effective amount means an amount of drug effective to treat cancer.

Here, the pharmaceutical composition may further comprise a pharmaceutically acceptable carrier. The pharmaceutically acceptable carrier may be any carrier as long as the carrier is a non-toxic substance suitable for delivery to a patient. Distilled water, alcohol, fat, wax, and inert solid may be contained as the carrier. A pharmaceutically acceptable adjuvant (buffer, dispersant) may also be contained in the pharmaceutical composition.

Specifically, by including a pharmaceutically acceptable carrier in addition to the active ingredient, the pharmaceutical composition may be prepared into a parenteral formulation depending on its route of administration using conventional methods known in the art. Here, the term "pharmaceutically acceptable" means that the carrier does not have more toxicity than the subject to be applied (prescribed) can adapt while not inhibiting activity of the active ingredient.

When the pharmaceutical composition is prepared into a parenteral formulation, it may be made into preparations in the form of injections, transdermal patches, nasal inhalants, or suppositories with suitable carriers according to methods known in the art. In a case of being made into injections, sterile water, ethanol, polyol such as glycerol or propylene glycol, or a mixture thereof may be used as a suitable carrier; and an isotonic solution, such as Ringer's solution, phosphate buffered saline (PBS) containing triethanol amine or sterile water for injection, and 5% dextrose, or the like may preferably be used. Formulation of pharmaceutical compositions is known in the art, and reference may specifically be made to Remington's Pharmaceutical Sciences (19th ed., 1995) and the like. This document is considered part of the present description.

A preferred dose of the pharmaceutical composition may range from 0.01 µg/kg to 10 g/kg, or 0.01 mg/kg to 1 g/kg, per day, depending on the patient's condition, body weight, sex, age, severity of the patient, and route of administration. The dose may be administered once a day or may be divided into several times a day. Such a dose should not be construed as limiting the scope of the present invention in any aspect.

Subjects to which the pharmaceutical composition can be applied (prescribed) are mammals and humans, with humans being particularly preferred. In addition to the active ingredient, the pharmaceutical composition of the present application may further contain any compound or natural extract, which has already been validated for safety and is known to have an anticancer activity, so as to boost or reinforce an anticancer activity.

In still yet another aspect of the present invention, there is provided a kit for treating cancer containing a fusion protein dimer comprising an IL-2 protein or a variant thereof and a CD80 protein or a fragment thereof, and an immune checkpoint inhibitor.

In still yet another aspect of the present invention, there is provided a use of a composition for combined administration containing a fusion protein dimer comprising an IL-2 protein or a variant thereof and a CD80 protein or a fragment thereof, and an immune checkpoint inhibitor for preventing or treating cancer.

In still yet another aspect of the present invention, there is provided a use of a composition for combined administration containing a fusion protein comprising an IL-2 protein or a variant thereof and a CD80 protein or a fragment thereof, and an immune checkpoint inhibitor for enhancing a therapeutic effect on cancer.

In still yet another aspect of the present invention, there is provided a use of a composition for combined administration containing a fusion protein comprising an IL-2 protein or a variant thereof and a CD80 protein or a fragment thereof, and an immune checkpoint inhibitor for manufacture of a medicament for treating cancer.

In still yet another aspect of the present invention, there is provided a method for preventing or treating cancer and/or a method for enhancing a therapeutic effect on cancer, comprising administering, to a subject, a composition for combined administration containing a fusion protein dimer comprising an IL-2 protein or a variant thereof and a CD80 protein or a fragment thereof, or a fusion protein dimer where the two fusion proteins are attached, and an immune checkpoint inhibitor.

The subject may be an individual suffering from cancer. In addition, the subject may be a mammal, preferably a human. The fusion protein comprising an IL-2 protein or a variant thereof and a CD80 protein or a fragment thereof, or the fusion protein dimer where the two fusion proteins are attached is as described above.

Route of administration, dose, and frequency of administration of the fusion protein or fusion protein dimer and NK cells may vary depending on the patient's condition and the presence or absence of side effects, and thus the fusion protein or fusion protein dimer may be administered to a subject in various ways and amounts. The optimal administration method, dose, and frequency of administration can be selected in an appropriate range by those skilled in the art.

Due to IL-2 activity, the fusion protein in an embodiment of the present invention can activate immune cells such as natural killer cells. Thus, the fusion protein can be effectively used for cancer. In particular, it was identified that as compared with the wild type, an IL-2 variant with two to five amino acid substitutions, in particular, an IL-2 variant that contains amino acid substitutions at two, three, four, or five positions among the positions selected from the group consisting of R38A, F42A, Y45A, E61R, and L72G, has low binding ability for the IL-2 receptor alpha chain and thus exhibits improved characteristics with respect to pharmacological side effects of conventional IL-2. Thus, such an IL-2 variant, when used alone or in the form of a fusion protein, can decrease incidence of vascular (or capillary) leakage syndrome (VLS), a problem with IL-2 conventionally known.

Mode for Carrying Out the Invention

Hereinafter, the present invention will be described in more detail by way of the following examples. However, the following examples are only for illustrating the present invention, and the scope of the present invention is not limited thereto.

I. Preparation of Fusion Protein

Preparation Example 1

Preparation of hCD80-Fc-IL-2 Variant (2M): GI101

In order to produce a fusion protein comprising a human CD80 fragment, an Fc domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 8) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (2M) (R38A, F42A) (SEQ ID NO: 6) having two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 9. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI101".

Purification was carried out using chromatography containing MabSelect SuRe protein A resin. The fusion protein was bound thereto under a condition of 25 mM Tris, 25 mM NaCl, pH 7.4. Then, elution was performed with 100 mM NaCl, 100 mM acetic acid, pH 3. 20% 1 M Tris-HCl at pH 9 was placed in a collection tube, and then the fusion protein was collected. For the collected fusion protein, the buffer was exchanged through dialysis with PBS buffer for 16 hours.

Thereafter, absorbance at 280 nm wavelength was measured, over time, with size exclusion chromatography using a TSKgel G3000SWXL column (TOSOH Bioscience), to obtain a highly concentrated fusion protein. Here, the isolated and purified fusion protein was subjected to SDS-PAGE under reduced (R) or non-reduced (NR) condition, and stained with Coomassie Blue to check its purity (FIG. 6). It was identified that the fusion protein was contained at a concentration of 2.78 mg/ml when detected with Nano-Drop (FIG. 7). In addition, the results obtained by analysis using size exclusion chromatography are provided in FIG. 8.

Preparation Example 2

Preparation of mCD80-Fc-IL-2 Variant (2M): mGI101

In order to produce a fusion protein comprising a mouse CD80, an Fc domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 14) which encodes a fusion protein that contains a signal peptide (SEQ ID NO: 1), a mCD80 (SEQ ID NO: 13), an Ig hinge (SEQ ID NO: 3), an Fc domain (SEQ ID NO: 4), a linker (SEQ ID NO: 5), and an IL-2 variant (2M) (R38A, F42A) (SEQ ID NO: 6) with two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 15. After the vector was introduced, culture was performed for 7 days in an environment of 37° C., 125 rpm, and 8% $CO_2$ concentration. Then, the culture was harvested and the fusion protein was purified therefrom. The purified fusion protein was designated "mGI101".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 9). It was found that the fusion protein was contained at a concentration of 1.95 mg/ml when detected by absorbance at 280 nm using NanoDrop.

Preparation Example 3

Preparation of hCD80-Fc: GI101C1

In order to produce a fusion protein comprising a human CD80 fragment and an Fc domain, a polynucleotide was synthesized through the Invitrogen GeneArt Gene Synthesis service of ThermoFisher Scientific. Specifically, the polynucleotide contains a nucleotide sequence (SEQ ID NO: 16) which encodes a fusion protein that contains a signal peptide (SEQ ID NO: 1), a CD80 fragment (SEQ ID NO: 2), an Ig hinge (SEQ ID NO: 3), and an Fc domain (SEQ ID NO: 4). The polynucleotide was inserted into pcDNA3_4 vector. In addition, the vector was introduced into CHO cells (Expi-CHO™) to express the fusion protein of SEQ ID NO: 17. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI101C1".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 10). It was observed that the fusion protein was contained at a concentration of 3.61 mg/ml when detected by absorbance at 280 nm using NanoDrop.

Preparation Example 4

Preparation of Fc-IL-2 Variant (2M): GI101C2

In order to produce a fusion protein comprising an Fc domain and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 18) which encodes a fusion protein that contains a signal peptide (SEQ ID NO: 1), an Fc domain (SEQ ID NO: 4), a linker (SEQ ID NO: 5), and an IL-2 variant (2M) (R38A, F42A) (SEQ ID NO: 6) with two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 19. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI101C2".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 11). It was found that the fusion protein was contained at a concentration of 4.79 mg/ml when detected by absorbance at 280 nm using NanoDrop.

Preparation Example 5

Preparation of mCD80-Fc: mGI101C1

In order to produce a fusion protein comprising a mouse CD80 and an Fc domain, a polynucleotide was synthesized through the Invitrogen GeneArt Gene Synthesis service of ThermoFisher Scientific. Specifically, the polynucleotide contains a nucleotide sequence (SEQ ID NO: 20) which encodes a fusion protein that contains a signal peptide (SEQ ID NO: 1), a mCD80 (SEQ ID NO: 13), an Ig hinge (SEQ ID NO: 3), and an Fc domain (SEQ ID NO: 4), in this order, from the N-terminus. The polynucleotide was inserted into pcDNA3_4 vector. In addition, the vector was introduced into CHO cells (Expi-CHO™) to express the fusion protein of SEQ ID NO: 21. After the vector was introduced, culture was performed for 7 days in an environment of 37° C., 125 rpm, and 8% $CO_2$ concentration. Then, the culture was harvested and the fusion protein was purified therefrom. The purified fusion protein was designated "mGI101C1".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 12). It was observed that the fusion protein was contained at a concentration of 2.49 mg/ml when detected by absorbance at 280 nm using NanoDrop.

The fusion proteins prepared in Preparation Examples 1 to 5 are summarized in Table 1 below.

TABLE 1

| Item | N-terminus | Linker | C-terminus |
| --- | --- | --- | --- |
| Preparation Example 1 (GI101) | hCD80 fragment | Fc domain | hIL-2m |
| Preparation Example 2 (mGI101) | mCD80 fragment | Fc domain | hIL-2m |
| Preparation Example 3 (GI101C1) | CD80 fragment | Fc domain | — |
| Preparation Example 4 (GI101C2) | — | Fc domain | IL-2m |
| Preparation Example 5 (mGI101C1) | mCD80 fragment | Fc domain | — |

Preparation Example 6

Preparation of CD80-Fc-IL-2: GI101w

In order to produce a fusion protein comprising a human CD80 fragment, an Fc domain, and a human IL-2, a polynucleotide was synthesized through the Invitrogen GeneArt Gene Synthesis service of ThermoFisher Scientific. Specifically, the polynucleotide contains a nucleotide sequence (SEQ ID NO: 31) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and mature human IL-2 (SEQ ID NO: 10), in this order, from the N-terminus. The polynucleotide was inserted into pcDNA3_4 vector. In addition, the vector was introduced into CHO cells (Expi-CHO™) to express the fusion protein of SEQ ID NO: 32. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI101w". The purification and collection of the fusion protein were carried out in the same manner as in Preparation Example 1.

Preparation Example 7

Preparation of hCD80-Fc-IL-2 Variant (3M): GI102-M45

In order to produce a fusion protein comprising a human CD80 fragment, an Fc domain, and an IL-2 variant (3M) (R38A, F42A, Y45A) (GI102-M45) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 25) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 22), in this order, from the N-terminus. The polynucleotide was inserted into pcDNA3_4 vector. In addition, the vector was introduced into CHO cells (Expi-CHO™) to express the fusion protein of SEQ ID NO: 26. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI102-M45". The purification and collection of the fusion protein were carried out in the same manner as in Preparation Example 1. The isolated and purified fusion protein was subjected to SDS- PAGE under reduced (R) or non-reduced (NR) condition and stained with Coomassie Blue to check its purity (FIG. 13).

Preparation Example 8

Preparation of hCD80-Fc-IL-2 Variant (3M): GI102-M61

In order to produce a fusion protein comprising a human CD80 fragment, an Fc domain, and an IL-2 variant (3M) (R38A, F42A, E61R) (GI102-M61) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 27) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 23), in this order, from the N-terminus. The polynucleotide was inserted into pcDNA3_4 vector. In addition, the vector was introduced into CHO cells (Expi-CHO™) to express the fusion protein of SEQ ID NO: 28. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI102-M61".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 14).

Preparation Example 9

Preparation of hCD80-Fc-IL-3M: GI102-M72

In order to produce a fusion protein comprising a human CD80 fragment, an Fc domain, and an IL-2 variant (3M) (R38A, F42A, L72G) (GI102-M72) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 29) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 24), in this order, from the N-terminus. The polynucleotide was inserted into pcDNA3_4 vector. In addition, the vector was introduced into CHO cells (Expi-CHO™) to express the fusion protein of SEQ ID NO: 30. After the vector was introduced, culture was performed for 7 days in an environment of 37° C., 125 rpm, and 8% $CO_2$ concentration. Then, the culture was harvested and the fusion protein was purified therefrom. The purified fusion protein was designated "GI102-M72".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 15).

Preparation Example 10

Preparation of mCD80-Fc-IL-3M: mGI102-M61

In order to produce a fusion protein comprising a mouse CD80 fragment, an Fc domain, and an IL-2 variant (3M) (R38A, F42A, E61R) (GI102-M61) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 33) which encodes a fusion protein that contains a signal peptide (SEQ ID NO: 1), a mCD80 fragment (SEQ ID NO: 13), an Ig hinge (SEQ ID NO: 3), an Fc domain (SEQ ID NO: 4), a linker (SEQ ID NO: 5), and an IL-2 variant (SEQ ID NO: 23), in this order, from the N-terminus. The polynucleotide was inserted into pcDNA3_4 vector. In addition, the vector was introduced into CHO cells (Expi-CHO™) to express the fusion protein of SEQ ID NO: 34. After the vector was introduced, culture was performed for 7 days in an environment of 37° C., 125 rpm, and 8% $CO_2$ concentration. Then, the culture was harvested and the fusion protein was purified therefrom. The purified fusion protein was designated "mGI102-M61".

The purification and collection of the fusion protein were carried out in the same manner as in Preparation Example 1.

II. Identification of Binding Affinity Between Fusion Protein and its Ligand

In order to identify the binding affinity between the fusion protein and its ligand, the binding affinity was measured using Octet RED 384.

Experimental Example 1

Identification of Binding Affinity Between hCTLA-4 and GI101

AR2G biosensor (Amine Reactive $2^{nd}$ gen, ForteBio, Cat: 18-5092) was previously hydrated with 200 μl of distilled water in a 96-well microplate (GreinerBio-one, Cat: 655209). A ligand (CTLA-4, Human CTLA-4/CD152, His tag, Sino Biological, Cat: 11159-H08H) to be attached to the AR2G biosensor was diluted with 10 mM acetate buffer (pH 5, AR2G reagent Kit, ForteBio, Cat: 18-5095) to a concentration of 5 μg/ml. In addition, GI101 to be attached to the ligand was diluted with 1×AR2G kinetic buffer (AR2G reagent Kit, ForteBio, Cat: 18-5095) to a concentration of 1,000 nM, 500 nM, 250 nM, 125 nM, or 62.5 nM. Activation buffer was prepared by mixing 20 mM EDC and 10 mM s-NHS (AR2G reagent Kit, ForteBio, Cat: 18-5095) in distilled water. 80 μl of each reagent was placed in a 384-well microplate (Greiner Bio-one, Cat: 781209) and the program was set up.

As a result, the binding affinity between hCTLA-4 and GI101 was measured as illustrated in FIG. 16.

Experimental Example 2

Identification of Binding Affinity Between hPD-L1/GI101 and hPD-L1/PD-1

Ni-NTA (Nickel charged Tris-NTA, Ni-NTA Biosensors, ForteBio, 18-5101) was previously hydrated with 200 μl of 1×Ni-NTA kinetic buffer (10×Kinetics buffer, ForteBio, 18-1042) in a 96-well microplate (GreinerBio-one, Cat: 655209). A ligand (Human PD-L1/B7-H1 protein, His-tag, Sino biological, Cat: 10084-H08H) to be attached to the Ni-NTA Biosensors was diluted with 1×Ni-NTA kinetic buffer to a concentration of 5 μg/ml. GI101 to be attached to the ligand was diluted with 1×Ni-NTA kinetic buffer at 1,000 nM, 500 nM, 250 nM, 125 nM, or 62.5 nM. In addition, human PD-1/PDCD1 (Human PD-1/PDCD1, Fc Tag, Sino Biological, Cat: 10377-H02H) to be attached to the ligand was diluted with 1×Ni-NTA kinetic buffer to a concentration of 2,000 nM, 1,000 nM, 500 nM, 250 nM, or 125 nM. Then, 80 μl of each reagent was placed in a 384-well microplate and the program was set up.

As a result, the binding affinity between hPD-L1 and GI101 was measured as illustrated in FIG. 17. In addition, the binding affinity between hPD-L1 and hPD-1 was measured as illustrated in FIG. 18.

Experimental Example 3

Identification of Binding Affinity Between mCTLA-4 and mGI101

The binding affinity between mCTLA-4 and mGI101 was examined in the same manner as in Experimental Example 1. Here, the equipment used is as follows: Biosensor: AR2G, Ligand: mCTLA-4 (Recombinant Mouse CTLA-4 Fc chimera, R&D Systems, Cat: 434-CT-200), Analyte: mGI101 (500 nM, 250 nM, 125 nM, 62.5 nM, 31.3 nM).

As a result, the binding affinity between mCTLA-4 and mGI101 was measured as illustrated in FIG. 19.

Experimental Example 4

Identification of Binding Affinity Between mPD-L1 and mGI101

The binding affinity between mPD-L1 and mGI101 was identified in the same manner as in Experimental Example 1. Here, the equipment used is as follows. Biosensor: AR2G, Ligand: mPD-L1 (Recombinant Mouse mGI101 B7-H1/PD-L1 Fc chimera, R&D Systems, Cat: 434-CT-200), Analyte: mGI101 (500 nM, 250 nM, 125 nM, 62.5 nM, 31.3 nM).

As a result, the binding affinity between mPD-L1 and mGI101 was measured as illustrated in FIG. 20.

Experimental Example 5

Identification of Binding Ability of GI-101 (hCD80-Fc-hIL-2v) to CTLA-4

Binding kinetics measurements were performed using the Octet RED 384 instrument (ForteBio, Pall Life Science) with agitation at 30° C. and 1,000 rpm. The binding ability for CTLA-4 was measured using the Amine Reactive 2 generation (AR2G) biosensor chip, and the binding ability for PD-L1 was measured using the Nickel charged Tris-NTA (Ni-NTA) biosensor chip. The AR2G biosensor chip was activated with a combination of 400 mM EDC and 100 mM sulfo-NHS. Then, Human CTLA-4-His Tag (Sino Biological, Cat: 11159-H08H) was diluted with 10 mM acetate buffer (pH 5) to 5 μg/ml, and loaded on the AR2G biosensor chip for 300 seconds and fixed.

Then, binding of CTLA-4 to GI-101 (hCD80-Fc-hIL-2v), GI-101C1 (hCD80-Fc), Ipilimumab (Bristol-Myers Squibb), and GI-101C2 (Fc-hIL-2v) at various concentrations was measured for 300 seconds and dissociation thereof was also measured for 300 seconds. Binding kinetics analysis was performed using Octet Data Analysis HT software ver. 10 provided by Pall Corporation. The results are illustrated in FIG. 21.

Experimental Example 6

Identification of Binding Affinity Between IL-2Rα or IL-2Rβ and GI101

The binding ability for IL-2Rα was measured using the AR2G biosensor, and the binding ability for IL-2Rβ was measured using the Ni-NTA biosensors (Nickel charged Tris-NTA, Ni-NTA Biosensors, ForteBio, 18-5101).

A ligand (IL-2Rα-His Tag, Acro, Cat: ILA-H52H9) to be attached to the AR2G biosensor was diluted with 10 mM acetate buffer (pH 5, AR2G reagent Kit, ForteBio, Cat: 18-5095) to a concentration of 5 μg/ml. The AR2G biosensor was activated with a buffer prepared by mixing 400 mM EDC and 100 mM sulfo-NHS, and then the diluted ligand was loaded on the AR2G biosensor for 300 seconds and fixed.

Meanwhile, a ligand (IL-2Rβ-His Tag, Acro, Cat: CD2-H5221) to be attached to the Ni-NTA biosensor was diluted with 1×Ni-NTA kinetic buffer to a concentration of 5 μg/ml. The diluted ligand was loaded on the Ni-NTA biosensor for 600 seconds and fixed.

Thereafter, GI101, GI101w, or Proleukin (Novartis, hIL-2), at various concentrations, to be attached to the ligand was loaded thereon for 300 seconds. Then, binding thereof was measured and dissociation thereof was also measured for 300 seconds. Binding kinetics analysis was performed using Octet Data Analysis HT software ver. 10 provided by Pall Corporation. The results are illustrated in FIGS. 22 to 24.

As a result, it was identified that GI101 has low binding ability for the IL-2 receptor alpha chain, IL-2Rα, and high binding ability for IL-2Rβ, as compared with GI101w and Proleukin.

Experimental Example 7

Measurement of Binding Affinity Between Fusion Protein and Ligand

In order to identify binding affinity between the fusion protein and its ligand, binding affinity was measured using Octet RED 384.

Experimental Example 7.1

Identification of Binding Affinity Between IL-2 Alpha Receptor and GI101-M45, GI101-M61, or GI101-M72

AR2G biosensor (Amine Reactive 2nd gen, ForteBio, Cat: 18-5092) was previously hydrated with 200 μl of distilled water (DW) in a 96-well microplate (GreinerBio-one, Cat: 655209). A ligand (Human IL-2 R alpha protein, His Tag, Acro, ILA-H52H9) to be attached to the biosensor was diluted with 10 mM acetate buffer (pH 5) (AR2G reagent Kit, ForteBio, Cat: 18-5095) to a concentration of 5 μg/ml. An analyte (GI101-M45, GI101-M61, GI101-M72) to be attached to the ligand was diluted with 1×AR2G kinetic buffer (AR2G reagent Kit, ForteBio, Cat: 18-5095) to 500 nM, 250 nM, 125 nM, and 62.5 nM, respectively. Activation buffer was prepared by mixing 20 mM EDC and 10 mM s-NHS (AR2G reagent Kit, ForteBio, Cat: 18-5095) in DW. 80 μl of each reagent was placed in a 384-well microplate (Greiner Bio-one, Cat: 781209) and the program was set up.

As a result, the binding affinity between IL-2 alpha receptor and GI101-M45 is illustrated in FIG. 25. In addition, the binding affinity between IL-2 alpha receptor and GI101-M61 is illustrated in FIG. 26, and the binding affinity between IL-2 alpha receptor and GI101-M72 is illustrated in FIG. 27.

Experimental Example 7.2

Identification of Binding Affinity of GI102-M45, GI102-M61, and GI102-M72 to IL-2 10

Ni-NTA Biosensors were previously hydrated with 200 µl of 1×Ni-NTA kinetic buffer (10×Kinetics buffer, ForteBio, 18-1042) in a 96-well microplate. A ligand (Human IL-2 R beta protein, His-Tag, Acro, CD2-H5221) to be attached to the biosensor was diluted with 1×Ni-NTA kinetic buffer to a concentration of 2 µg/ml. GI102-M45, GI102-M61, or GI102-M72 to be attached to the ligand was diluted with 1×Ni-NTA kinetic buffer to a concentration of 500 nM, 250 nM, 125 nM, or 62.5 nM. 80 µl of each reagent was placed in a 384-well microplate and the program was set up.

As a result, the binding affinity between IL-2Rβ and GI102-M45 was measured as illustrated in FIG. 28, and the binding affinity between IL-2Rβ and GI102-M61 was measured as illustrated in FIG. 29. In addition, the binding affinity between IL-2Rβ and GI102-M72 was measured as illustrated in FIG. 30.

III. Identification of Immune Activity of Fusion Protein

Experimental Example 8

Identification of IFN-γ Production Caused by Fusion Protein

Experimental Example 8.1

Culture of CFSE-Labeled PBMCs

Peripheral blood mononuclear cells (PBMCs) isolated from a human were labeled with carboxyfluorescein succinimidyl ester (CFSE) by being reacted with 1 µM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFB-labeled PBMCs were resuspended in the culture medium (RPMI1640 medium containing 10% fetal bovine serum (FBS), 10 mM HEPES, 100 U/ml penicillin/streptomycin, 1 mM sodium pyruvate, 55 µM 2-mercaptoethanol, 1 mM non-essential amino acid, and 2 mM L-glutamine), and then added to a 96-well microplate at 1×10⁵ cells per well. Treatment with 5 µg/ml of PHA (Lectin from Phaseolus Vulgaris, red kidney bean, Sigma-Aldrich, St. Louis, Mo., USA, Cat. No. L1668-5MG), and GI101, GI101C1, GI101C2, or IL-2 (Aldesleukin; human recombinant IL-2, Novartis) was performed and incubation was performed in a 5% CO$_2$ incubator at 37° C. for 6 days.

Here, the treatment with GI101, GI101C1, GI101C2, and IL-2 was performed at a concentration of 1 nM, 10 nM, or 100 nM. The cells were analyzed by FACS, and human IFN-γ present in the culture medium was measured using an ELISA kit (Biolegend, San Diego, Calif., USA, Cat. No. 430103).

Experimental Example 8.2

FACS Analysis

The cell pellets obtained by removing the supernatant were washed with FACS buffer (3% fetal bovine serum (FBS), 10 mM EDTA, 1M HEPES, 100 unit/ml Penicillin, Streptomycin, 10 µg/ml, 1 mM sodium pyruvate), and then reacted with Fc blocker (Biolegend, Cat. No. 422302) at 4° C. for 5 minutes. Then, treatment with APC anti-CD3 Ab (Biolegend, Cat. No. 300412) and PE anti-CD8a Ab (Biolegend, Cat. No. 300908) was performed and reaction was allowed to proceed at 4° C. for 20 minutes. Then, the resultant was washed with FACS buffer. The cell pellets were resuspended in FACS buffer and then analyzed using BD LSR Fortessa (BD Biosciences, San Diego, Calif., USA) and FlowJo software.

Experimental Example 8.3

Human IFN-γ ELISA

The amount of human IFN-γ secreted into the supernatant of each sample in which the cells had been cultured was measured using a human IFN-γ ELISA kit (Biolegend, Cat. No. 430103). Briefly, anti-human-IFN-γ antibodies were added to an ELISA plate, and reaction was allowed to proceed overnight at 4° C. so that these antibodies were coated thereon. Then, blocking was performed at room temperature for 1 hour with a PBS solution to which 1% BSA had been added. Washing with a washing buffer (0.05% Tween-20 in PBS) was performed, and then a standard solution and each sample were properly diluted and added thereto. Then, reaction was allowed to proceed at room temperature for 2 hours.

After the reaction was completed, the plate was washed and secondary antibodies (detection antibodies) were added thereto. Reaction was allowed to proceed at room temperature for 1 hour. Washing with a washing buffer was performed, and then an Avidin-HRP solution was added thereto. Reaction was allowed to proceed at room temperature for 30 minutes. A substrate solution was added thereto and color development reaction was induced in the dark at room temperature for 20 minutes. Finally, H$_2$SO$_4$ was added thereto to stop the color development reaction, and the absorbance at 450 nm was measured with Epoch Microplate Spectrophotometer (BioTek Instruments, Inc., Winooski, Vt., USA).

As a result, it was found that cells treated with GI101 exhibited a remarkable increase in IFN-γ secretion, as compared with cells treated with GI101C1, GI101C2, or IL-2 (FIGS. 31 and 32).

Experimental Example 9

Identification of Effect of GI101 on Proliferation of CD8+ T Cells

Peripheral blood mononuclear cells (PBMCs) isolated from a human were labeled with CFSE by being reacted with 1 µM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFB-labeled PBMCs were resuspended in the culture medium (RPMI1640 medium containing 10% fetal bovine serum (FBS), 10 mM HEPES, 100 U/ml penicillin/streptomycin, 1 mM sodium pyruvate, 55 μM 2-mercaptoethanol, 1 mM non-essential amino acid, and 2 mM L-glutamine), and then added to a 96-well microplate at 1×10$^5$ cells per well.

Thereafter, treatment with 1 μg/ml of an anti-CD3ε antibody (Biolegend Cat. No. L1668-5MG), and GI101, GI101C1, GI101C2, or Proleukin (Novartis) was performed and incubation was performed in a 5% $CO_2$ incubator at 37° C. for 6 days. Here, the cells were treated with GI101, GI101C1, GI101C2, and IL-2 at a concentration of 100 nM. The incubated cells were examined for their degree of proliferation by measuring, with FACS analysis using APC-TCRαβ and PE-CD8α antibodies, a proportion of CD8+ T cells that had not been labeled with CFSE.

As a result, it was found that GI101 activated proliferation of CD8+ T cells in vitro to a similar extent to the wild-type IL-2 Proleukin (FIGS. 33 and 34).

Experimental Example 10

Identification of Effect of GI101 and GI102 on Proliferation of CD8+ T Cells

Human PBMCs were purchased from Allcells (Lot #3014928, USA). 1M CellTrace CFSE dye was used, which was reacted with the human PBMCs under a light-blocking condition at room temperature for 20 minutes. The cells were labeled with CFSE by being reacted with 1 μM CellTrace CFSE dye at 37° C. for 20 minutes. CFSE not bound to the cells was removed by being reacted for 5 minutes with culture medium having a 5-fold volume of the staining reaction solution and then by being centrifuged at 1,300 rpm for 5 minutes. The CFB-labeled PBMCs were resuspended in the culture medium (RPMI1640 medium containing 10% fetal bovine serum (FBS), 10 mM HEPES, 100 U/ml penicillin/streptomycin, 1 mM sodium pyruvate, 55 μM 2-mercaptoethanol, 1 mM non-essential amino acid, and 2 mM L-glutamine), and then added to a 96-well microplate at 1×10$^5$ cells per well.

Thereafter, the CFB-labeled PBMCs were subjected to treatment with 1 μg/ml of an anti-CD3ε antibody (OKT3, eBioscience, USA), and GI101, GI101C1, GI101C2, or Proleukin (Novartis), and incubation was performed in a 5% $CO_2$ incubator at 37° C. for 7 days. Here, the cells were subjected to treatment with GI101, GI101C1, GI101C2, and IL-2 at a concentration of 10 μM.

The incubated cells were examined for their degree of proliferation by measuring, with FACS analysis using an anti-human CD4-PE antibody (BioLegend, USA), an anti-human CD8-PE/Cy7 antibody (BioLegend, USA), and an anti-human FoxP3-APC antibody (BioLegend, USA), a proportion of CD8+ T cells that had not been labeled with CFSE.

As a result, the GI101, GI102_M61, GI101C2, and Proleukin treatment groups exhibited a significant increase in proportion of CD8+ T cells, as compared with the control group (no stimulus), the anti-CD3 antibody alone treatment group, and the GI101C1 treatment group. In addition, as compared with the negative control group (no stimulus) and the anti-CD3 alone treatment group, the GI101, GI101C2, and Proleukin treatment groups exhibited a significant increase in proliferation of CD4+/FoxP3+ Treg cells, whereas the GI102 and GI101C1 treatment groups did not exhibit a significant increase in proliferation of CD4+/FoxP3+ Treg cells (FIG. 35).

Experimental Example 11

Identification of Effect of GI101 or GI101w on Proliferation of CD8+ T Cells and NK Cells 7-week-old C57BL/6 mice purchased from Orient Bio (Korea) were divided into 3 groups, each group containing 3 mice, and PBS, GI101, or GI101w was injected intraperitoneally thereinto. Here, GI101 and GI101w were respectively prepared to be at 40.5 μg in 200 μl of PBS, and injected intraperitoneally thereinto. Five days after the injection, the spleens were removed from the mice of each group. The cells were isolated therefrom, and the total number of cells was measured using a hematocytometer. Splenocytes were examined for proportions of CD8+ T cells and NK cells therein, with FACS analysis using staining with APC-CD3ε antibody (Biolegend; 145-2C11), PE-NK1.1 antibody (Biolegend; PK136), and Pacific blue-CD8a antibody (BD; 53-6.7). As such, the numbers of CD8+ T cells and NK cells present in the spleen were calculated.

As a result, it was identified that GI101 activated proliferation of CD8+ T cells and NK cells in vivo as compared with GI101w (FIGS. 36 and 37).

Experimental Example 12

Identification of Effect of GI101 on Function of T Cells

An experiment was performed using a CTLA-4 blockade bioassay kit (Promega Cat. No. JA4005). The experiment is briefly described as follows. CTLA-4 effector cells kept in liquid nitrogen were thawed in a 37° C. constant temperature water bath for 3 minutes, and 0.8 ml of CTLA-4 effector cells were mixed well with 3.2 ml of pre-warmed assay buffer (90% RPMI+10% fetal bovine serum). Then, the mixture was added to a 96-well white cell culture plate (SPL, Cat. No. 30196) at 25 μl per well. Then, 25 μl of GI101 at various concentrations was added thereto. For a negative control, 25 μl of assay buffer was added thereto. Then, the 96-well-white cell culture plate was covered and placed at room temperature until aAPC/Raji cells were prepared.

aAPC/Raji cells kept in liquid nitrogen were thawed in a 37° C. constant temperature water bath for 3 minutes, and 0.8 ml of aAPC/Raji cells were mixed well with 3.2 ml of pre-warmed assay buffer. Then, 25 μl of the mixture was added to the plate at per well, and reaction was allowed to proceed in a 5% $CO_2$ incubator at 37° C. for 16 hours. After the reaction was completed, the resultant was allowed to stand at room temperature for 15 minutes, and then the Bio-Glo reagent was added thereto while taking care to avoid bubbles. The Bio-Glo reagent was also added to three of the outermost wells and the wells were used as blanks to correct the background signal. Reaction was allowed to proceed at room temperature for 10 minutes, and then luminescence was measured with Cytation 3 (BioTek Instruments, Inc., Winooski, Vt., USA). Final data analysis was performed by calculating RLU (GI101-background)/RLU (no treatment-background).

As a result, it was found that GI101 attached to CTLA-4 expressed on effector T cells, and activated the function of T cells rather than inhibiting the same (FIGS. 38 and 39).

Experimental Example 13

Identification of Effect of mGI101 and mGI102 on Immune Cells 7-week-old C57BL/6 mice purchased from Orient Bio (Korea) were divided into 3 groups, each group containing 3 mice, and PBS, 3 mg/kg, 6 mg/kg, or 12 mg/kg of GI101, or 3 mg/kg, 6 mg/kg, or 12 mg/kg of mGI102 (mGI102-M61) was administered intravenously thereinto. On days 1, 3, 5, 7, and 14 after the injection, the spleens were removed from the mice of each group. Thereafter, for the spleen tissue, the numbers of effector CD8+ T cells, NK cells, and Treg cells were calculated with FACS analysis using respective antibodies, and proportions of effector CD8+ T cells and NK cells with respect to Treg cells were respectively calculated. The information on the antibodies used in each cell assay is as follows:

Effector CD8+ T cells: PB anti-mouse CD3ε antibody (Biolegend, #155612; KT3.1.1), FITC anti-mouse CD8a antibody (BD, #553031, 53-6.7), PE/Cy7 anti-mouse CD44 antibody (Biolegend, #103030; IM7), APC anti-mouse CD122 antibody (Biolegend, #123214; TM-(β1)

NK cells: PB anti-mouse CD3ε antibody (Biolegend, #155612; KT3.1.1), PE anti-mouse NK-1.1 (Biolegend, #108708; PK136)

Treg cells: FITC anti-mouse CD3 antibody (Biolegend, #100204; 17A2), PB anti-mouse CD4 antibody (Biolegend, #100531; RM4-5), PE anti-mouse CD25 antibody (Biolegend, #102008; PC61), APC anti-mouse Foxp3 antibody (Invitrogen, #FJK-16s, 17-5773-82).

As a result, the group having received mGI101 or mGI102 (mGI102-M61) exhibited a significant increase in numbers of CD8+ T cells and NK cells at the time points from 3 days to 14 days after administration, as compared with the PBS administration group. In addition, it was found that the group having received mGI102 exhibited a significant increase in proportions of activated CD8+ T cells/Treg cells and NK cells/Treg cells at the time points from 3 days to 14 days after administration, as compared with the PBS administration group (FIG. 40).

IV. Identification of Anticancer Effect of Fusion Protein

Experimental Example 14

Identification of Effect of GI101 on Inhibition of T Cell Activity by Cancer Cells Expressing PD-L1 and CTLA-4

NC1-H292 cancer cell line expressing PD-L1 and CTLA-4 was cultured for 3 hours in a culture medium containing 10 μg/ml Mitomycin C (Sigma), and then Mitomycin C was removed by washing with the culture medium. Thereafter, $5 \times 10^4$ cells of the Mitomycin C-treated NC1-H292 cancer cell line were incubated with $1 \times 10^5$ cells of human PBMCs in a 96-well microplate. Here, treatment with 5 μg/ml of PHA (Sigma) was performed for T cell activity. In addition, GI101C1 and GI101 at a concentration of 50 nM were reacted with IgG1-Fc (Biolegend) or abatacept (=Orencia; Bristol-Myers Squibb) at a concentration of 50 nM for 30 minutes at 4° C., and then the resultant was used to treat the NC1-H292 cancer cells. After 3 days, the supernatant of the cell incubate was collected and the amount of IFN-γ was quantified using an ELISA kit (Biolegend).

As a positive control group, human PBMCs stimulated with PHA in the absence of the Mitomycin C-treated NC1-H292 cancer cell line were used; and as a negative control group, human PBMCs stimulated with PHA in the presence of the Mitomycin C-treated NC1-H292 cancer cell line was used. An experimental method using the IFN-γ ELISA kit was carried out in the same manner as in Experimental Example 9.3.

As a result, GI101 effectively activated the immune response that had been inhibited by the cancer cell line overexpressing PD-L1. In addition, it was discovered that GI101 inhibited signaling of CTLA-4 expressed on effector T cells (FIGS. 41 and 42).

Experimental Example 15

Identification of Anticancer Effect of mGI101 in Mice Transplanted with Mouse-Derived Colorectal Cancer Cells BALB/c mice (female, 7-week-old) acquired from Orient Bio were subjected to an acclimation period of 7 days. Then, $5 \times 10^6$ cells of CT-26 cancer cell line (ATCC, USA) were mixed with 0.05 ml of phenol red-free matrigel matrix (BD), and allotransplantation of the mixture was performed by subcutaneous administration at 0.1 ml in the right dorsal region of the mice. A certain period of time after the cancer cell transplantation, the tumor volume was measured and subjects that reached about 28 mm³ were selected, and then the selected mice were grouped evenly based on tumor size and body weight, each group containing 10 mice. Thereafter, using a disposable syringe (31G, 1 mL), hIgG4 was administered at a dose of 6 mg/kg to a negative control group. For experimental groups, mGI101 at a dose of 3 mg/kg, 6 mg/kg or 12 mg/kg was administered intravenously thereto. A total of three administrations were given once every three days after the first administration. The tumor size was measured daily.

As a result, in the groups having received mGI101 at a dose of 6 mg/kg and 12 mg/kg, respectively, the tumor size was significantly inhibited as compared with the negative control group at some measurement time points and at the end of the test (FIG. 43). Further, as a result of measuring the survival rate, in the group having received mGI101 at a dose of 6 mg/kg, significant improvement was observed as compared with the negative control group at some measurement time points and at the end of the test (FIG. 44).

Experimental Example 16

Identification of Anticancer Effect of GI101 in Mice Transplanted with Mouse-Derived Colorectal Cancer Cells Experimental Example 16.1

Identification of Tumor Inhibitory Effect

BALB/c mice (female, 7-week-old) acquired from Orient Bio were subjected to an acclimation period of 7 days. Then, $5 \times 10^6$ cells of CT-26 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm³ to 200 mm³ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI101 at a dose of 0.1 mg/kg or 1 mg/kg was administered intravenously thereto. A total of three administrations were given once every three days after the first administration. The tumor size was measured daily.

As a result, in the CT-26 cancer cell line-transplanted mice, all groups having received an anti-PD-1 antibody, an anti-PD-1 antibody and an anti-CTLA-4 antibody, or GI101 at a dose of 0.1 mg/kg or 1 mg/kg exhibited significant inhibition of tumor growth, as compared with the negative control group. In particular, the experimental group having received GI101 at a dose of 0.1 mg/kg exhibited a significant tumor inhibitory effect, as compared with the anti-PD-1 antibody treatment group (*p<0.05) (FIG. 45).

Experimental Example 16.2

Immune Cell Analysis in Cancer Tissues

The mice of each group in Experimental Example 16.1 were sacrificed when the tumor volume reached an average of 200 mm$^3$, and cancer tissues were collected. Thereafter, the cancer tissues were separated to a single-cell level to analyze immune cells therein, and then FACS analysis was performed on immune cells in the cancer tissues using the following antibodies. Specifically, Anti-mouse-CD3 (Biolegend, Cat. No. 100320), Anti-mouse-CD4 (Biolegend, Cat. No. 100526), Anti-mouse-CD8 (Biolegend, Cat. No. 100750), Anti-mouse-FoxP3 (eBioscience, Cat. No. 12-5773-82), Anti-mouse-CD25 (Biolegend, Cat. No. 102049), Anti-mouse-CD44 (eBioscience, Cat. No. 61-0441-82), Anti-mouse-PD-1 (Biolegend, Cat. No. 135218), Anti-mouse-IFN-gamma (Biolegend, Cat. No. 505832), Anti-mouse-CD49b (Biolegend, Cat. No. 108906), Anti-mouse-H2 (Invitrogen, Cat. No. A15443), Anti-mouse-CD11c (Biolegend, Cat. No. 117343), Anti-mouse-CD80 (eBioscience, Cat. No. 47-4801-82), Anti-mouse-CD86 (Biolegend, Cat. No. 104729), Anti-mouse-F4/80 (eBioscience, Cat. No. 47-4801-82), and Anti-mouse-CD206 (eBioscience, Cat. No. 17-2061-80) were used as the antibodies.

As a result, the experimental group having received GI101 at a dose of 0.1 mg/kg exhibited a significant increase in CD8+ T cells, as compared with the positive control group having received an anti-PD-1 antibody alone at a dose of 5 mg/kg (*p<0.05, FIGS. 46 and 47). Furthermore, all experimental groups having received GI101 exhibited a significantly increased level of expression of IFN-γ in T cells, as compared with the negative control group (*p<0.05, FIGS. 46 and 47). In addition, the experimental group having received GI101 at a dose of 0.1 mg/kg exhibited an increase in M1 macrophages as compared with the negative control group and the positive control group having received an anti-PD-1 antibody alone (FIGS. 48 and 49). In addition, all experimental groups having received GI101 exhibited an increased level of CD86 expression in macrophages and dendritic cells (*p<0.05, FIGS. 48 to 51).

Experimental Example 17

Identification of Anticancer Effect of GI101 in Mice Transplanted with Mouse-Derived Lung Cancer Cells Experimental Example 17.1. Identification of Tumor Inhibitory Effect C57BL/6 mice (female, 7-week-old) acquired from Orient Bio were subjected to an acclimation period of 7 days. Then, 5×10$^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 mm$^3$ to 200 mm$^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI101 at a dose of 0.1 mg/kg or 1 mg/kg was administered intravenously thereto. A total of three administrations were given once every three days after the first administration. The tumor size was measured daily.

As a result, all experimental groups exhibited a significant tumor inhibitory effect, as compared with the negative control group (*p<0.05) (FIG. 52).

Experimental Example 17.2

Immune Cell Analysis in Cancer Tissues

The mice of each group in Experimental Example 17.1 were sacrificed when the tumor volume reached an average of 200 mm$^3$, and cancer tissues were collected. Thereafter, FACS analysis was performed in the same manner as Experimental Example 16.2 to analyze immune cells in the cancer tissues.

As a result, the experimental group having received GI101 at a dose of 0.1 mg/kg exhibited a significant increase in CD8+ T cells, as compared with the positive control group having received an anti-PD-1 antibody alone (*p<0.05, FIG. 59). Furthermore, all experimental groups having received GI101 exhibited a significantly increased level of expression of IFN-γ, as compared with the negative control group (*p<0.05, FIG. 59). In addition, all experimental groups having received GI101 exhibited an increased level of CD86 expression in macrophages and dendritic cells (*p<0.05, FIGS. 53 to 55).

Experimental Example 18

Identification of Anticancer Effect of mGI102-M61 in Mice Transplanted with Mouse-Derived Colorectal Cancer Cells BALB/c mice (female, 7-week-old) acquired from Orient Bio were subjected to an acclimation period of 7 days. Then, 5×10$^6$ cells of CT-26 cancer cell line (ATCC, USA) were mixed with 0.05 ml of phenol red-free matrigel matrix (BD), and allotransplantation of the mixture was performed by subcutaneous administration at 0.1 ml in the right dorsal region of the mice. A certain period of time after the cancer cell transplantation, the tumor volume was measured and subjects that reached about 28 mm$^3$ were selected, and then the selected mice were grouped evenly based on tumor size and body weight, each group containing 10 mice. Thereafter, using a disposable syringe (31G, 1 mL), hIgG4 was administered at a dose of 6 mg/kg to a negative control group. For experimental groups, mGI102-M61 at a dose of 3 mg/kg, 6 mg/kg, or 12 mg/kg was administered intravenously thereto.

A total of three administrations were given once every three days after the first administration. The tumor size was measured daily.

As a result, it was identified that the experimental group having received mGI102-M61 at a dose of 12 mg/kg exhibited significant inhibition of tumor growth at some measurement time points and at the end of the test, as compared with the negative control group (FIG. 56). In addition, as a result of measuring a survival rate, it was identified that the experimental group having received mGI102-M61 at a dose of 12 mg/kg exhibited significant improvement at some measurement time points and at the end of the test, as compared with the negative control group (FIG. 57).

Experimental Example 19

Identification of Anticancer Effect of mGI101 in Mice Transplanted with Mouse-Derived Colorectal Cancer Cells BALB/c mice (female, 7-week-old) acquired from Orient Bio were subjected to an acclimation period of 7 days. Then, $5 \times 10^6$ cells of CT-26 cancer cell line (ATCC, USA) were mixed with 0.05 ml of phenol red-free matrigel matrix (BD), and allotransplantation of the mixture was performed by subcutaneous administration at 0.1 ml in the right dorsal region of the mice. A certain period of time after the cancer cell transplantation, the tumor volume was measured and subjects that reached about 200 mm$^3$ to 250 mm$^3$ were selected, and then the selected mice were grouped evenly based on tumor size and body weight, each group containing 10 mice.

Thereafter, using a disposable syringe (31G, 1 mL), hIgG4 was administered at a dose of 4 mg/kg to a negative control group. For experimental groups, mGI101 at a dose of 1 mg/kg, 4 mg/kg, or 6 mg/kg was administered intravenously thereto. Additionally, groups having received mCD80 at 4.9 mg/kg or Fc-IL-2v (GI101C2) at 2.8 mg/kg were set as control groups. In addition, a group having simultaneously received mCD80 at 4.9 mg/kg and Fc-IL-2v (GI101C2) at 2.8 mg/kg was set as a control group.

In tumor volume measurement, it was identified that the group having received mGI101 at a dose of 6 mg/kg exhibited significant inhibition at some measurement time points and at the end of the test, as compared with the negative control. An excellent tumor growth inhibition rate was observed as compared with the group having received a combination of mCD80 and Fc-IL-2v (GI101C2) (FIGS. 58 and 59).

In conclusion, in the tumor growth-inhibitory efficacy test on BALB/c mice allotransplanted with CT-26, a BALB/c mouse-derived colorectal cancer cell line, it was demonstrated that the test substance mGI101 had tumor inhibitory efficacy under this test condition as compared with mCD80 and IL-2v single preparations; and it was identified that mGI101 exhibited an excellent anticancer efficacy as compared with the group having received a combination of mCD80 and IL-2v (FIGS. 58 and 59). In particular, the group having received mGI101 at a dose of 6 mg/kg exhibited significant inhibition of tumor size, as compared with the negative control group and the group having received a combination of mCD80 and Fc-IL2v (GI101C2).

V. Determination of Anticancer Effect of Combined Administration of Fusion Protein Dimer and Immune Checkpoint Inhibitor Experimental Example 20

Determination of Anticancer Effect by Combined Administration of GI101 and Anti-PD-1 Antibody in Human-Derived Breast Cancer Cell Transplanted Mice This test evaluated tumor growth inhibitory effect in a tumor model transplanted with xenogeneic MDA-MB-231 cells which are human-derived breast cancer cells, using a humanized mouse model prepared by xenogeneic transplant of human PBMC into a NSGb2m mouse, after intraperitoneal administration of GI101 as a test material, and Keytruda (Pembrolizumab, MSD), an anti-PD-1 antibody as a positive control material, alone or in combination.

Stock solutions of the test material, negative control material, and positive control material described in Table 2 were diluted by adding an excipient according to each dose.

TABLE 2

|  | Test material | Positive control material | Negative control material | Excipient |
| --- | --- | --- | --- | --- |
| Name of material | GI101 | Keytruda | hIgG4 | PBS |
| Description | clear liquid | clear liquid | clear liquid | clear liquid |
| Component | Fc fusion protein | anti-PD-1 antibody | — | — |
| pH | 7.5 | — | — | — |
| Storage condition | stored under refrigeration (4° C.) | stored under refrigeration (4° C.) | stored under refrigeration (4° C.) | stored under refrigeration (4° C.) |
| Handling precautions | stored under refrigeration until administration and used by reconstitution on the administration day | stored under refrigeration until administration and used by reconstitution on the administration day | stored under refrigeration until administration and used by reconstitution on the administration day | — |

Human-derived breast cancer cells, MDA-MB-231 (Homo sapiens, human mammary gland/breast; derived from metastatic site: pleural effusion) were purchased from Korea cell line bank (Korea) and used in the test. A cell culture medium was used by mixing fetal bovine serum (FBS, 16000-044, Thermofisher scientific, U.S.A.), penicillin-streptomycin; 10,000 units/ml penicillin and 10,000 µg/ml streptomycin (15140122, Thermofisher scientific, U.S.A.), and RPMI1640 (A1049101, Thermofisher scientific, U.S.A.) per 100 ml as the composition shown in the table below.

TABLE 3

| Name | Composition (ml) |
| --- | --- |
| FBS | 10 |
| Penicillin-Streptomycin | 1 |
| RPMI1640 | 89 |
| Total volume | 100 |

Cells to be used in the test were thawed, placed in a flask for cell culture, and cultured at 37° C., in a 5% $CO_2$ incubator (MCO-170M, Panasonic, Japan). The cultured cells were suspended using trypsin-EDTA (Cat. 25200-072, Thermofisher scientific, U.S.A.). The suspended cells were collected by centrifugation (125×g, 5 minutes) by using a centrifuge, transferred to a new medium and a new flask, and subcultured. On the day of cell line transplantation, the cultured cells were placed in a centrifuge tube, recovered, and then centrifuged (125×g, 5 minutes) to discard the supernatant. Then, a cell suspension ($5 \times 10^6$ cells/0.05 ml) was made with PBS (Cat. LB 001-04, Welgene Inc., KOREA), and stored on ice until inoculation.

For the test, 8-week-old female NSGb2m (NOD.Cg-B2M$^{tm1Unc}$Prkdc$^{scid}$Il2rd$^{tm1Wjl}$/SzJ), mice were purchased from JoongABio (Korea) and used. The body weight was measured the next day after the end of quarantine and acclimatization period, and then a human-derived PBMC cell suspension ($5 \times 10^6$ cells/0.2 ml) prepared for healthy animals was filled in a disposable syringe, and administered to the caudal vein of the animals. General symptoms were observed once a day after cell transplantation.

A solution prepared by adding phenol red-free matrigel matrix (0.05 ml, 356237, BD, U.S.A.) to the prepared MDA-MB-231 cell suspension ($5 \times 10^6$ cells/0.05 ml) was filled in a disposable syringe, and transplanted by administering subcutaneously (0.1 ml/head) to the right back of the animal transplanted with human PBMC. General symptoms were observed once a day during the engraftment and growth period following cell line transplantation.

After a certain period following cell transplantation, the tumor volume was measured for mice showing no abnormal health status, and 32 individuals were selected so that the average of each group reached 40 to 80 mm³. The selected animals were divided into 4 groups (8 animals per group) as evenly as possible, based on the tumor volume and body weight.

The test groups were organized as shown in Table 4. The test material was administered to animals using a disposable syringe (31G, 1 ml), and the frequency of administration was twice a week with a total of 4 administrations.

TABLE 4

| | Group | Dosage (mg/kg) | Volume administered (ml/kg) | Number of animal |
| --- | --- | --- | --- | --- |
| G1 | hIgG4 | 6 | 10 | 8 |
| G2 | GI101 | 6 | 10 | 8 |
| G3 | Keytruda | 5 | 10 | 8 |
| G7 | GI101 + Keytruda | 6 + 5 | 10 | 8 |

During the observation period, general symptoms such as appearance, behavior, excretion, or the like were observed once a day, and deceased animals were identified. Body weight was measured on the day of cell line transplantation, twice a week, and on sacrifice day of the animal.

During the observation period, maximum length (L) and perpendicular width (W) of the tumor were measured three times a week using a digital caliper (mitutoyo, Japan), and applied to the following equation to calculate the tumor volume (TV).

$$TV(mm^3) = (W^2 \times L)/2 \qquad \text{<Equation 1>}$$

$$\% \ TGI(\text{Tumor Growth Inhibition}) = (1-(Ti-T0)/(Vi-V0)) \times 100 \qquad \text{<Equation 2>}$$

The tumor volume of each individual before administration was set as the value measured at the time of grouping.

On day 21, day 25, day 28, and day 31 after tumor transplantation, the drugs shown in Table 4 were respectively administered, and as a result, tumor growth was inhibited in the GI101 or Keytruda alone treatment groups compared to the control group (hIgG4). Tumor growth was inhibited in the GI101 and Keytruda combined treatment groups compared to the control group. Tumor growth was inhibited in the GI101 and Keytruda combined treatment group compared to the GI101 or Keytruda alone treatment groups (FIG. 60).

Tumor growth inhibition rate was calculated at the end of the experiment (day 42 after tumor transplantation), as compared to the drug treatment day 1 (day 17 after tumor transplantation). As a result, the hIgG4 treatment group had 2 mice having tumor growth inhibition rate of 30% or more, 1 mouse having tumor growth inhibition rate of 50% or more, and 1 mouse having tumor growth inhibition rate of 80% or more; the GI101 treatment group had 5 mice having tumor growth inhibition rate of 30% or more, 5 mice having tumor growth inhibition rate of 50% or more, and 2 mice having tumor growth inhibition rate of 80% or more; the Keytruda treatment group had 7 mice having tumor growth inhibition rate of 30% or more, 5 mice having tumor growth inhibition rate of 50% or more, and 3 mice having tumor growth inhibition rate of 80% or more; and the GI101 and Keytruda combined treatment group had 8 mice having tumor growth inhibition rate of 30% or more, 8 mice having tumor growth inhibition rate of 50% or more, and 6 mice having tumor growth inhibition rate of 80% or more (FIG. 61).

In addition, the degree of tumor growth of individual experimental animals in each treatment group when GI101 and Keytruda were used in combination in mice transplanted with human-derived breast cancer cells are shown in FIGS. 62 to 66.

Experimental Example 21

Determination of Anticancer Effect by Combined Administration of mGI101 and Anti-PD-1 Antibody in Mouse-Derived Colorectal Cancer Cell Transplanted Mice This test evaluated tumor growth inhibitory effect in a tumor model in which allogeneic murine colon adenocarcinoma cells (MC38) were transplanted to C57BL/6 mice, after intraperitoneal administration of mGI101 as a test material, and an anti-PD-1 antibody as a positive control material, alone or in combination.

Murine colon adenocarcinoma cells (MC38), which are rodent-derived colorectal cancer cells, were purchased from Kerafast Inc. (USA) and used in the test. MC38 cells were cultured in a RPMI1640 medium (Gibco) containing 10% fetal bovine serum (Gibco) and 1% antibiotic/antifungal agent (Gibco). The cultured cells were harvested using trypsin and suspended in PBS. 1×10^6 MC38 cells were injected s.c. into the right flank of C57BL/6 female mice (7-week-old) to establish an allograft tumor model.

Mice were randomly assigned (5 per group) based on the tumor volume (30 mm$^3$). Tumor grafts were identified about 2 days after cell inoculation. The test groups were organized as shown in Table 5, and test materials were administered.

TABLE 5

|   | Test group | Administration route, administration interval | Dosage | Number of animal |
|---|---|---|---|---|
| G1 | Vehicle control(hIgG4) | i.p. BIW × 16 days | 10 mg/kg | 5 |
| G2 | mGI101 | i.p. day 1, 5, 9 | 6 mg/kg | 6 |
| G3 | Anti-PD-1 antibody (cloneRMP1-14, InVivoMab) | i.p. BIW × 16 days | 5 mg/kg | 5 |
| G4 | mGI101 + anti-PD-1 antibody | i.p. day 1, 5, 9 (mGI101) i.p. BIW × 16 days (anti-PD-1 antibody) | 0.6 mg/kg 5 mg/kg | 5 |

During the test period, clinical symptoms such as disease and behavior changes, or the like were observed once a day, and deceased animals were identified. The animals were sacrificed after the test period. The size of MC38 solid cancer was measured using a tumor 3D scanner (TM900, Peria, belgium). The average weight loss and percentage change, and average tumor growth inhibition were calculated for each experimental group. Antitumor efficacy was evaluated compared to the vehicle control group.

All statistical calculations were performed using Prism 8.0 (Graph Pad Software Inc., USA). Tumor volume measurements were compared through one-way ANOVA (end time) followed by Bonferroni's multiple comparison test. A "p" value <0.05 was considered significant.

All test animals remained healthy without showing signs of pathological abnormalities after administration of mGI101 and co-administration of mGI101 and an anti-PD-1 antibody. The results of combination therapy using mGI101 and/or an anti-PD-1 antibody against MC38 tumors are shown in FIGS. 67 to 73. An anticancer effect was observed in the drug treatment group compared to the control group, and the difference in tumor size was noticeable during 16 days of test period. MC38 tumor was known as a model responsive to anti-PD-1 antibodies in previous literature, and an anticancer effect was also observed in the anti-PD-1 antibody administration group of this test (p>0.01). The anticancer effect was also found in the mGI101 (6 mpk) alone administration group as much as in the anti-PD-1 antibody administration group (p>0.01). mGI101 (0.6 mpk)+anti-PD-1 (5 mpk) combined administration group showed a remarkably excellent anticancer effect (p>0.0001).

Individual tumor sizes for each test group are shown in FIGS. 69 to 73. According to the results of individual tumor size, slight tumor regression was observed in some animals among the anti-PD-1 antibody administration group. The mGI101 (6 mpk) alone administration group showed better tumor growth inhibitory effect than the anti-PD-1 antibody administration group. The tumor size remained the same until 5 to 7 days, but regrew after 7 days. The tumor size remained the same until 5 to 7 days, but regrew after 7 days. The combined administration group (GI101 (0.6 mpk)+anti-PD-1 antibody (5 mpk)) showed remarkably excellent tumor growth inhibition. In particular, two of the combined administration group showed complete response (no tumor).

MC38 cells were re-injected into the left flank (opposite to the initial injection site of cancer cells) of the two mice of the combined administration group showing complete remission. These mice continued anti-PD-1 antibody administration (5 mpk, BIW) until day 32 (FIG. 74). A small tumor (>30 mm$^3$) was found in one of the two mice, but the tumor size did not grow any more until day 35 (FIG. 69). Tumor was not found in another mouse after tumor was re-injected (FIGS. 69 and 74).

In conclusion, the anti-tumor efficacy of mGI101 alone and in combination with an anti-PD-1 antibody was tested in the MC38 allogeneic tumor model, and as a result, the combined administration group (GI101 (0.6 mpk)+anti-PD-1 (5 mpk)) showed the best anti-tumor efficacy. Two experimental animals of the combined administration group showed a complete response, and the mice showing a complete response showed an anticancer effect when MC38 was re-injected (Table 6).

TABLE 6

| | CR mouse | |
|---|---|---|
| Days After treatment | No. 1 Tumor Vol.(mm$^3$) | No. 2 Tumor Vol.(mm$^3$) |
| D1 | 78.2 | 23.6 |
| D2 | 84.5 | 13.5 |
| D3 | 36.3 | 0 |
| D4 | 0 | 0 |
| D5 | 0 | 0 |
| D6 | 0 | 0 |
| D7 | 0 | 0 |
| D8 | 0 | 0 |
| D9 | 0 | 0 |
| D10 | 0 | 0 |
| D11 | 0 | 0 |
| D12 | 0 | 0 |
| D13 | 0 | 0 |
| D14 | 0 | 0 |
| D15 | 0 | 0 |
| D16 | 0 | 0 |
| D17 | 0 | 0 |
| D18 | 0 | 0 |
| D19 | 0 | 0 |
| D20 | 0 | 0 |
| D21 | 0 | 0 |
| D22 | 0 | 0 |
| D23 | 0 | 0 |
| D24 | 0 | 0 |
| *D25 | 0 | 0 |
| D26 | 0 | 0 |
| D27 | 0 | 0 |
| D28 | 0 | 0 |
| D29 | 0 | 0 |
| D30 | 0 | 0 |
| D31 | 0 | 0 |
| D32 | 12.8 | 0 |

Experimental Example 22

Determination of Anticancer Effect by Combined Administration of mGI101 and Anti-PD-L1 Antibody in Mouse-Derived Colorectal Cancer Cell Transplanted Mice This test evaluated tumor growth inhibitory effect in a tumor model in which allogeneic murine colon carcinoma cells (CT26) were transplanted to BALB/c mice, after intraperitoneal administration of mGI101 as a test material, and an anti-PD-L1 antibody (BioXcell, Cat #BE0101) as a positive control material, alone or in combination.

CT26 cells were cultured in a RPMI1640 medium (Gibco) containing 10% fetal bovine serum (Gibco) and 1% antibiotic/antifungal agent (Gibco). The cultured cells were harvested using trypsin and suspended in PBS. $5 \times 10^5$ CT26 cells were subcutaneously injected into the right flank of BALB/c female mice (7-week-old) to establish an allograft tumor model.

Mice were randomly assigned (4 per group) based on the tumor volume (50~120 mm$^3$). Tumor grafts were identified about 2 days after cell inoculation. The test groups were organized as shown in Table 7, and test materials were administered.

TABLE 7

| Test group | | Administration route, administration interval | Dosage | Number of animal |
|---|---|---|---|---|
| G1 | Vehicle control(PBS) | i.p. BIW × 9 days | — | 4 |
| G2 | mGI101 | i.v. QW × 9 days | 3 mg/kg | 4 |
| G3 | Anti-PD-L1 antibody (BioXcell, Cat# BE0101) | i.p. BIW × 9 days | 10 mg/kg | 4 |
| G4 | mGI101 + anti-PD-L1 antibody | i.v. QW × 9 days (mGI101) | 3 mg/kg | 4 |
| G4 | mGI101 + anti-PD-L1 antibody | i.p. BIW × 9 days (anti-PD-L1 antibody) | 10 mg/kg | 4 |

During the test period, clinical symptoms such as disease and behavior changes, or the like were observed once a day, and deceased animals were identified. The animals were sacrificed after the test period. The size of CT26 solid cancer was measured using a tumor 3D scanner (TM900, Peria, belgium). The average weight loss and percentage change, and average tumor growth inhibition were calculated for each experimental group. An antitumor efficacy was evaluated compared to the vehicle control group.

All statistical calculations were performed using Prism 8.0 (Graph Pad Software Inc., USA). Tumor volume measurements were compared through one-way ANOVA (end time) followed by Bonferroni's multiple comparison test. A "p" value <0.05 was considered significant.

The anti-tumor efficacy of mGI101 alone and in combination with an anti-PD-L1 antibody was tested in the CT26 allogeneic tumor model, and as a result, the combined administration group (mGI101 (3 mpk)+anti-PD-L1 (10 mpk)) showed the best anti-tumor efficacy (FIG. 75).

Experimental Example 23

Determination of Anticancer Effect by Combined Administration of mGI101 and Anti-TIGIT Antibody in Mouse-Derived Colorectal Cancer Cell Transplanted Mice This test evaluated tumor growth inhibitory effect in a tumor model in which allogeneic murine colon carcinoma cells (CT26) were transplanted to BALB/c mice, after intraperitoneal administration of mGI101 as a test material, and an anti-TIGIT antibody specifically binding to the extracellular domain (ECD) of TIGIT having the amino acid sequence of SEQ ID NO: 39 as a positive control material, alone or in combination.

CT26 cells were cultured in a RPMI1640 medium (Gibco) containing 10% fetal bovine serum (Gibco) and 1% antibiotic/antifungal agent (Gibco). The cultured cells were harvested using trypsin and suspended in PBS. $5 \times 10^5$ CT26 cells were subcutaneously injected into the right flank of BALB/c female mice (7-week-old) to establish an allograft tumor model.

Mice were randomly assigned (5 per group) based on the tumor volume (50~120 mm$^3$). Tumor grafts were identified about 2 days after cell inoculation. The test groups were organized as shown in Table 8, and test materials were administered.

TABLE 8

| Test group | | Administration route, administration interval | Dosage | Number of animal |
|---|---|---|---|---|
| G1 | Vehicle control(PBS) | i.p. BIW × 9 days | — | 5 |
| G2 | mGI101 | i.v. QW × 9 days | 3 mg/kg | 5 |
| G3 | Anti-TIGIT antibody (Merck, MK-7684) | i.p. BIW × 9 days | 20 mg/kg | 5 |
| G4 | mGI101 + anti-TIGIT antibody | i.v. QW × 9 days (mGI101) | 3 mg/kg | 5 |
| G4 | mGI101 + anti-TIGIT antibody | i.p. BIW × 9 days (anti-TIGIT antibody) | 20 mg/kg | |

During the test period, clinical symptoms such as disease and behavior changes, or the like were observed once a day, and deceased animals were identified. The animals were sacrificed after the test period. The size of CT26 solid cancer was measured using a tumor 3D scanner (TM900, Peria, belgium). The average weight loss and percentage change, and average tumor growth inhibition were calculated for each experimental group. An antitumor efficacy was evaluated compared to the vehicle control group.

All statistical calculations were performed using Prism 8.0 (Graph Pad Software Inc., USA). Tumor volume measurements were compared through one-way ANOVA (end time) followed by Bonferroni's multiple comparison test. A "p" value <0.05 was considered significant.

The anti-tumor efficacy of mGI101 alone and in combination with an anti-TIGIT antibody was tested in the CT26 allogeneic tumor model, and as a result, the combined administration group (mGI101 (3 mpk)+anti-TIGIT (20 mpk)) showed the best anti-tumor efficacy (FIG. 76). An anti-tumor effect was not observed in the anti-TIGIT antibody alone administration group, as compared with the control group. However, the combined administration of an anti-TIGIT antibody and mGI101 showed a remarkably superior anti-tumor effect, as compared with the mGI101 alone administration group.

What is claimed is:

1. A pharmaceutical composition comprising, as active ingredients, a fusion protein dimer comprising an IL-2 protein variant comprising substitutions of the 38th and 42nd in the amino acid of SEQ ID NO: 10 and an extracellular domain of CD80 protein; and an immune checkpoint inhibitor selected from the group consisting of an anti-PD-1 antibody, an anti-PD-L1 antibody and an anti-TIGIT antibody.

2. The pharmaceutical composition according to claim 1, wherein the IL-2 protein variant and the extracellular domain of CD80 protein are linked to each other via a linker.

3. The pharmaceutical composition according to claim 1, wherein the extracellular domain of CD80 consists of the 35th to 242nd amino acid sequence of SEQ ID NO: 11.

4. The pharmaceutical composition according to claim 1, wherein the fusion protein comprises the amino acid sequence of SEQ ID NO: 9.

5. The pharmaceutical composition according to claim 1, wherein
the anti-PD-1 antibody is any one selected from the group consisting of pembrolizumab, nivolumab, cemiplimab, JTX-4014, spartalizumab, camrelizumab, sintilimab, tislelizumab, toripalimab, dostarlimab, INCMGA00012, AMP-224, and AMP-514; and
the anti-PD-L1 antibody is any one selected from the group consisting of atezolizumab, avelumab, durvalumab, KN035, CK-301, AUNP12, CA-170, and BMS-986189.

* * * * *

SEQUENCE LISTING

<160> NUMBER OF SEQ ID NOS: 39

<210> SEQ ID NO 1
<211> LENGTH: 25
<212> TYPE: PRT
<213> ORGANISM: Artificial Sequence
<220> FEATURE:
<223> OTHER INFORMATION: signal peptide (TPA)

<400> SEQUENCE: 1

Met Asp Ala Met Leu Arg Gly Leu Cys Cys Val Leu Leu Leu Cys Gly
1               5                   10                  15

Ala Val Phe Val Ser Pro Ser His Ala
            20                  25

<210> SEQ ID NO 2
<211> LENGTH: 208
<212> TYPE: PRT
<213> ORGANISM: Artificial Sequence
<220> FEATURE:
<223> OTHER INFORMATION: hB7-1:35-242

<400> SEQUENCE: 2

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
            195                 200                 205

<210> SEQ ID NO 3
<211> LENGTH: 30
<212> TYPE: PRT
<213> ORGANISM: Artificial Sequence
<220> FEATURE:
<223> OTHER INFORMATION: hinge

<400> SEQUENCE: 3

Gly Ser Gly Gly Gly Ser Gly Gly Gly Ser Gly Gly Gly
1               5                   10                  15

Ser Ala Glu Ser Lys Tyr Gly Pro Pro Cys Pro Pro Cys Pro
            20                  25                  30

<210> SEQ ID NO 4
<211> LENGTH: 216
<212> TYPE: PRT
<213> ORGANISM: Artificial Sequence
<220> FEATURE:
<223> OTHER INFORMATION: immunoglobulin fc

<400> SEQUENCE: 4

Ala Pro Glu Ala Ala Gly Gly Pro Ser Val Phe Leu Phe Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly
    210                 215

<210> SEQ ID NO 5
<211> LENGTH: 5
<212> TYPE: PRT
<213> ORGANISM: Artificial Sequence
<220> FEATURE:
<223> OTHER INFORMATION: linker

```
<400> SEQUENCE: 5

Gly Gly Gly Gly Ser
1               5

<210> SEQ ID NO 6
<211> LENGTH: 133
<212> TYPE: PRT
<213> ORGANISM: Artificial Sequence
<220> FEATURE:
<223> OTHER INFORMATION: hIL-2M

<400> SEQUENCE: 6

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 7
<211> LENGTH: 617
<212> TYPE: PRT
<213> ORGANISM: Artificial Sequence
<220> FEATURE:
<223> OTHER INFORMATION: fusion protein comprising variants of IL-2 and
      fragments of CD80

<400> SEQUENCE: 7

Met Asp Ala Met Leu Arg Gly Leu Cys Cys Val Leu Leu Leu Cys Gly
1               5                   10                  15

Ala Val Phe Val Ser Pro Ser His Ala Val Ile His Val Thr Lys Glu
            20                  25                  30

Val Lys Glu Val Ala Thr Leu Ser Cys Gly His Asn Val Ser Val Glu
        35                  40                  45

Glu Leu Ala Gln Thr Arg Ile Tyr Trp Gln Lys Glu Lys Lys Met Val
    50                  55                  60

Leu Thr Met Met Ser Gly Asp Met Asn Ile Trp Pro Glu Tyr Lys Asn
65                  70                  75                  80

Arg Thr Ile Phe Asp Ile Thr Asn Asn Leu Ser Ile Val Ile Leu Ala
                85                  90                  95

Leu Arg Pro Ser Asp Glu Gly Thr Tyr Glu Cys Val Val Leu Lys Tyr
            100                 105                 110

Glu Lys Asp Ala Phe Lys Arg Glu His Leu Ala Glu Val Thr Leu Ser
        115                 120                 125

Val Lys Ala Asp Phe Pro Thr Pro Ser Ile Ser Asp Phe Glu Ile Pro
```

-continued

```
            130                 135                 140
Thr Ser Asn Ile Arg Arg Ile Ile Cys Ser Thr Ser Gly Gly Phe Pro
145                 150                 155                 160

Glu Pro His Leu Ser Trp Leu Glu Asn Gly Glu Leu Asn Ala Ile
                165                 170                 175

Asn Thr Thr Val Ser Gln Asp Pro Glu Thr Glu Leu Tyr Ala Val Ser
                180                 185                 190

Ser Lys Leu Asp Phe Asn Met Thr Thr Asn His Ser Phe Met Cys Leu
                195                 200                 205

Ile Lys Tyr Gly His Leu Arg Val Asn Gln Thr Phe Asn Trp Asn Thr
            210                 215                 220

Thr Lys Gln Glu His Phe Pro Asp Asn Gly Ser Gly Gly Gly Gly Ser
225                 230                 235                 240

Gly Gly Gly Gly Ser Gly Gly Gly Ser Ala Glu Ser Lys Tyr Gly
                245                 250                 255

Pro Pro Cys Pro Pro Cys Pro Ala Pro Glu Ala Ala Gly Gly Pro Ser
                260                 265                 270

Val Phe Leu Phe Pro Pro Lys Pro Lys Asp Gln Leu Met Ile Ser Arg
            275                 280                 285

Thr Pro Glu Val Thr Cys Val Val Asp Val Ser Gln Glu Asp Pro
290                 295                 300

Glu Val Gln Phe Asn Trp Tyr Val Asp Gly Val Glu Val His Asn Ala
305                 310                 315                 320

Lys Thr Lys Pro Arg Glu Glu Gln Phe Asn Ser Thr Tyr Arg Val Val
                325                 330                 335

Ser Val Leu Thr Val Leu His Gln Asp Trp Leu Asn Gly Lys Glu Tyr
                340                 345                 350

Lys Cys Lys Val Ser Asn Lys Gly Leu Pro Ser Ser Ile Glu Lys Thr
            355                 360                 365

Ile Ser Lys Ala Lys Gly Gln Pro Arg Glu Pro Gln Val Tyr Thr Leu
            370                 375                 380

Pro Pro Ser Gln Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
                420                 425                 430

Ser Asp Gly Ser Phe Phe Leu Tyr Ser Arg Leu Thr Val Asp Lys Ser
                435                 440                 445

Arg Trp Gln Glu Gly Asn Val Phe Ser Cys Ser Val Leu His Glu Ala
            450                 455                 460

Leu His Asn His Tyr Thr Gln Lys Ser Leu Ser Leu Ser Leu Gly Gly
465                 470                 475                 480

Gly Gly Gly Ser Ala Pro Thr Ser Ser Ser Thr Lys Lys Thr Gln Leu
                485                 490                 495

Gln Leu Glu His Leu Leu Leu Asp Leu Gln Met Ile Leu Asn Gly Ile
                500                 505                 510

Asn Asn Tyr Lys Asn Pro Lys Leu Thr Ala Met Leu Thr Ala Lys Phe
                515                 520                 525

Tyr Met Pro Lys Lys Ala Thr Glu Leu Lys His Leu Gln Cys Leu Glu
            530                 535                 540

Glu Glu Leu Lys Pro Leu Glu Glu Val Leu Asn Leu Ala Gln Ser Lys
545                 550                 555                 560
```

Asn Phe His Leu Arg Pro Arg Asp Leu Ile Ser Asn Ile Asn Val Ile
            565                 570                 575

Val Leu Glu Leu Lys Gly Ser Glu Thr Thr Phe Met Cys Glu Tyr Ala
        580                 585                 590

Asp Glu Thr Ala Thr Ile Val Glu Phe Leu Asn Arg Trp Ile Thr Phe
        595                 600                 605

Cys Gln Ser Ile Ile Ser Thr Leu Thr
    610                 615

<210> SEQ ID NO 8
<211> LENGTH: 1857
<212> TYPE: DNA
<213> ORGANISM: Artificial Sequence
<220> FEATURE:
<223> OTHER INFORMATION: nucleotiedes coding fusion protein (GI101)

<400> SEQUENCE: 8

| | | |
|---|---|---|
| atggatgcta tgctgagagg cctgtgttgc gtgctgctgc tgtgtggcgc tgtgttcgtg | 60 |
| tctccttctc acgctgtgat ccacgtgacc aaagaagtga agaggtcgc cacactgtcc | 120 |
| tgcggccaca acgtttcagt ggaagaactg gcccagacca ggatctactg cagaaagaa | 180 |
| aagaaaatgg tgctgaccat gatgtccggc gacatgaaca tctggcctga gtacaagaac | 240 |
| cggaccatct tcgacatcac caacaacctg tccatcgtga ttctggccct gaggccttct | 300 |
| gatgagggca cctatgagtg cgtggtgctg aagtacgaga aggacgcctt caagcgcgag | 360 |
| cacctggctg aagtgacact gtccgtgaag gccgactttc ccacaccttc catctccgac | 420 |
| ttcgagatcc ctacctccaa catccggcgg atcatctgtt ctacctctgg cggctttcct | 480 |
| gagcctcacc tgtcttggct ggaaaacggc gaggaactga cgccatcaa caccaccgtg | 540 |
| tctcaggacc ccgaaaccga gctgtacgct gtgtcctcca gctggactt caacatgacc | 600 |
| accaaccaca gcttcatgtg cctgattaag tacggccacc tgagagtgaa ccagaccttc | 660 |
| aactggaaca ccaccaagca agagcactc cctgacaatg gatctggcgg cggaggttct | 720 |
| ggcggaggtg gaagcggagg cggaggatct gctgagtcta gtatggccc tccttgtcct | 780 |
| ccatgtcctg ctccagaagc tgctggcgga ccctctgtgt tcctgtttcc tccaaagcct | 840 |
| aaggaccagc tcatgatctc tcggacaccc gaagtgacct gcgtggtggt ggatgtgtct | 900 |
| caagaggacc ctgaggtgca gttcaattgg tacgtggacg gcgtggaagt gcacaacgcc | 960 |
| aagaccaagc ctagagagga acagttcaac tccacctaca gagtggtgtc cgtgctgacc | 1020 |
| gtgctgcacc aggattggct gaacggcaaa gagtacaagt gcaaggtgtc caacaagggc | 1080 |
| ctgccttcca gcatcgaaaa gaccatctcc aaggctaagg ccagcctag ggaaccccag | 1140 |
| gtttacaccc tgcctccaag ccaagaggaa atgaccaaga accaggtgtc cctgacctgc | 1200 |
| ctggtcaagg gcttctaccc ttccgacatt gccgtggaat gggagtccaa tggccagcct | 1260 |
| gagaacaact acaagaccac acctcctgtg ctggactccg acggctcctt ctttctgtac | 1320 |
| tctcgcctga ccgtggacaa gtctagatgg caagagggca acgtgttctc ctgctctgtg | 1380 |
| ctgcacgagg ccctgcacaa tcactacacc cagaagtccc tgtctctgtc tcttggaggt | 1440 |
| ggtggcggtt ctgccctac cagctcctct accaagaaaa cccagctcca gttggagcat | 1500 |
| ctgctgctgg acctccagat gattctgaac gggatcaaca actataagaa ccccaagctg | 1560 |
| accgccatgc tgaccgctaa gttctacatg cccaagaagg ccaccgagct gaagcacctc | 1620 |
| cagtgcctgg aagaagaact gaagcccctg gaagaggtgc tgaatctggc ccagtccaag | 1680 |

```
aacttccacc tgaggccacg ggacctgatc agcaacatca acgtgatcgt gctggaactg    1740
aagggctccg agacaacctt tatgtgcgag tacgccgacg agacagccac catcgtggaa    1800
tttctgaacc ggtggatcac cttctgccag agcatcatct ccacactgac ctgatga      1857
```

<210> SEQ ID NO 9
<211> LENGTH: 592
<212> TYPE: PRT
<213> ORGANISM: Artificial Sequence
<220> FEATURE:
<223> OTHER INFORMATION: fusion protein (GI101)

<400> SEQUENCE: 9

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335
```

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590

<210> SEQ ID NO 10
<211> LENGTH: 133
<212> TYPE: PRT
<213> ORGANISM: Artificial Sequence
<220> FEATURE:
<223> OTHER INFORMATION: hIL-2

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 11
<211> LENGTH: 288
<212> TYPE: PRT
<213> ORGANISM: Artificial Sequence
<220> FEATURE:
<223> OTHER INFORMATION: CD80

<400> SEQUENCE: 11

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 12
<211> LENGTH: 215
<212> TYPE: PRT
<213> ORGANISM: Artificial Sequence
<220> FEATURE:
<223> OTHER INFORMATION: modified Fc

<400> SEQUENCE: 12

```
Ser His Thr Gln Pro Leu Gly Val Phe Leu Phe Pro Pro Lys Pro Lys
 1               5                  10                  15

Asp Thr Leu Met Ile Ser Arg Thr Pro Glu Val Thr Cys Val Val Val
                20                  25                  30

Asp Val Ser Gln Glu Asp Pro Glu Val Gln Phe Asn Trp Tyr Val Asp
            35                  40                  45

Gly Val Glu Val His Asn Ala Lys Thr Lys Pro Arg Glu Glu Gln Phe
        50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
        195                 200                 205

Leu Ser Leu Ser Leu Gly Lys
210                 215

<210> SEQ ID NO 13
<211> LENGTH: 306
<212> TYPE: PRT
<213> ORGANISM: Artificial Sequence
<220> FEATURE:
<223> OTHER INFORMATION: mCD80

<400> SEQUENCE: 13

Met Ala Cys Asn Cys Gln Leu Met Gln Asp Thr Pro Leu Leu Lys Phe
 1               5                  10                  15

Pro Cys Pro Arg Leu Ile Leu Leu Phe Val Leu Leu Ile Arg Leu Ser
                20                  25                  30

Gln Val Ser Ser Asp Val Asp Glu Gln Leu Ser Lys Ser Val Lys Asp
            35                  40                  45

Lys Val Leu Leu Pro Cys Arg Tyr Asn Ser Pro His Glu Asp Glu Ser
        50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
130                 135                 140
```

```
Phe Ser Thr Pro Asn Ile Thr Glu Ser Gly Asn Pro Ser Ala Asp Thr
145                 150                 155                 160
Lys Arg Ile Thr Cys Phe Ala Ser Gly Gly Phe Pro Lys Pro Arg Phe
                165                 170                 175
Ser Trp Leu Glu Asn Gly Arg Glu Leu Pro Gly Ile Asn Thr Thr Ile
            180                 185                 190
Ser Gln Asp Pro Glu Ser Glu Leu Tyr Thr Ile Ser Ser Gln Leu Asp
        195                 200                 205
Phe Asn Thr Thr Arg Asn His Thr Ile Lys Cys Leu Ile Lys Tyr Gly
    210                 215                 220
Asp Ala His Val Ser Glu Asp Phe Thr Trp Glu Lys Pro Pro Glu Asp
225                 230                 235                 240
Pro Pro Asp Ser Lys Asn Thr Leu Val Leu Phe Gly Ala Gly Phe Gly
                245                 250                 255
Ala Val Ile Thr Val Val Ile Val Val Ile Ile Lys Cys Phe Cys
            260                 265                 270
Lys His Arg Ser Cys Phe Arg Arg Asn Glu Ala Ser Arg Glu Thr Asn
        275                 280                 285
Asn Ser Leu Thr Phe Gly Pro Glu Glu Ala Leu Ala Glu Gln Thr Val
    290                 295                 300
Phe Leu
305

<210> SEQ ID NO 14
<211> LENGTH: 1848
<212> TYPE: DNA
<213> ORGANISM: Artificial Sequence
<220> FEATURE:
<223> OTHER INFORMATION: nucleotiedes coding fusion protein (mGI101)

<400> SEQUENCE: 14
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag      240
aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcccctaa catcaccgag       420
tctggcaacc cttccgccga caccaagaga atcacctgtt tcgcctctgg cggcttccct    480
aagcctcggt tctcttggct ggaaaacggc agagagctgc ccggcatcaa taccaccatt     540
tctcaggacc cagagtccga gctgtacacc atctccagcc agctcgactt aacaccacc     600
agaaaccaca ccatcaagtg cctgattaag tacggcgacg cccacgtgtc cgaggacttt     660
acttgggaga acctcctga ggaccctcct gactctggat ctggcggcgg aggttctggc      720
ggaggtggaa gcggaggcgg aggatctgct gagtctaagt atggccctcc ttgtcctcca     780
tgtcctgctc agaagctgc tggcggaccc tctgtgttcc tgtttcctcc aaagcctaag     840
gaccagctca tgatctctcg gaccctgaa gtgacctgcg tggtggtgga tgtgtctcaa      900
gaggaccctg aggtgcagtt caattggtac gtgacggcg tggaagtgca caacgccaag     960
accaagccta gaggaacaa gttcaactcc acctatagag tggtgtccgt gctgaccgtg    1020
ctgcaccagg attggctgaa cggcaaagag tacaagtgca aggtgtccaa caagggcctg    1080
```

-continued

```
ccttccagca tcgaaaagac catcagcaag gctaagggcc agcctaggga acccaggtt     1140 tacaccctgc ctccaagcca agaggaaatg accaagaacc aggtgtccct gacctgcctg   1200
gtcaagggct tctacccttc cgacattgcc gtggaatggg agtccaatgg ccagcctgag   1260
aacaactaca agaccacacc tcctgtgctg actccgacg gctccttctt tctgtactct    1320
cgcctgaccg tggacaagtc taggtggcaa gagggcaacg tgttctcctg ctctgtgctg   1380
cacgaggctc tgcacaacca ctacacccag aagtccctgt ctctgtctct tggaggtggt   1440
ggcggttctg cccctacctc cagctctacc aagaaaaccc agctccagtt ggagcatctg   1500
ctgctggacc tccagatgat cctgaatggc atcaacaatt acaagaaccc caagctgacc   1560
gccatgctga ccgctaagtt ctacatgccc aagaaggcca ccgagctgaa gcacttgcag   1620
tgcctggaag aggaactgaa gcccctggaa gaagtgctga atctggccca gtccaagaac   1680
ttccacctga ggcctaggga cctgatctcc aacatcaacg tgatcgtgct ggaactgaaa   1740
ggctccgaga caaccttcat gtgcgagtac gccgacgaga cagccaccat cgtggaattt   1800
ctgaaccggt ggatcacctt ctgccagagc atcatctcca cactgacc              1848
```

<210> SEQ ID NO 15
<211> LENGTH: 616
<212> TYPE: PRT
<213> ORGANISM: Artificial Sequence
<220> FEATURE:
<223> OTHER INFORMATION: fusion protein (mGI101)

<400> SEQUENCE: 15

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220
```

```
Pro Pro Glu Asp Pro Asp Ser Gly Ser Gly Gly Gly Ser Gly
225                 230                 235                 240

Gly Gly Gly Ser Gly Gly Gly Ser Ala Glu Ser Lys Tyr Gly Pro
            245                 250                 255

Pro Cys Pro Pro Cys Pro Ala Pro Glu Ala Ala Gly Gly Pro Ser Val
        260                 265                 270

Phe Leu Phe Pro Pro Lys Pro Lys Asp Gln Leu Met Ile Ser Arg Thr
    275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
            355                 360                 365

Ser Lys Ala Lys Gly Gln Pro Arg Glu Pro Gln Val Tyr Thr Leu Pro
370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
            435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
            485                 490                 495

Leu Glu His Leu Leu Leu Asp Leu Gln Met Ile Leu Asn Gly Ile Asn
            500                 505                 510

Asn Tyr Lys Asn Pro Lys Leu Thr Ala Met Leu Thr Ala Lys Phe Tyr
            515                 520                 525

Met Pro Lys Lys Ala Thr Glu Leu Lys His Leu Gln Cys Leu Glu Glu
530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
            565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
            595                 600                 605

Gln Ser Ile Ile Ser Thr Leu Thr
            610                 615

<210> SEQ ID NO 16
<211> LENGTH: 1437
<212> TYPE: DNA
```

<213> ORGANISM: Artificial Sequence
<220> FEATURE:
<223> OTHER INFORMATION: nucleotiedes coding fusion protein (GI101C1)

<400> SEQUENCE: 16

```
atggatgcta tgctgagagg cctgtgttgc gtgctgctgc tgtgtggcgc tgtgttcgtg    60
tctccttctc acgctgtgat ccacgtgacc aaagaagtga agaggtcgc cacactgtcc    120
tgcggccaca acgtttcagt ggaagaactg gcccagacca ggatctactg cagaaagaa    180
aagaaaatgg tgctgaccat gatgtccggc gacatgaaca tctggcctga gtacaagaac    240
cggaccatct tcgacatcac caacaacctg tccatcgtga ttctggccct gaggccttct    300
gatgagggca cctatgagtg cgtggtgctg aagtacgaga aggacgcctt caagcgcgag    360
cacctggctg aagtgacact gtccgtgaag gccgactttc ccacaccttc catctccgac    420
ttcgagatcc ctacctccaa catccggcgg atcatctgtt ctacctctgg cggctttcct    480
gagcctcacc tgtcttggct ggaaaacggc gaggaactga cgccatcaa caccaccgtg    540
tctcaggacc ccgaaaccga gctgtacgct gtgtcctcca gctggactt caacatgacc    600
accaaccaca gcttcatgtg cctgattaag tacggccacc tgagagtgaa ccagaccttc    660
aactggaaca ccaccaagca agagcacttc cctgacaatg gatctggcgg cggaggttct    720
ggcggaggtg aagcggagg cggaggatct gctgagtcta agtatggccc tccttgtcct    780
ccatgtcctg ctccagaagc tgctggcgga ccctctgtgt tcctgtttcc tccaaagcct    840
aaggaccagc tcatgatctc tcggacaccc gaagtgacct gcgtggtggt ggatgtgtct    900
caagaggacc ctgaggtgca gttcaattgg tacgtggacg gcgtggaagt gcacaacgcc    960
aagaccaagc ctagagagga acagttcaac tccacctaca gagtggtgtc cgtgctgacc   1020
gtgctgcacc aggattggct gaacggcaaa gagtacaagt gcaaggtgtc caacaagggc   1080
ctgccttcca gcatcgaaaa gaccatctcc aaggctaagg ccagcctag gaaccccag    1140
gtttacaccc tgcctccaag ccaagaggaa atgaccaaga accaggtgtc cctgacctgc   1200
ctggtcaagg gcttctaccc ttccgacatt gccgtggaat gggagtccaa tggccagcct   1260
gagaacaact acaagaccac acctcctgtg ctggactccg acggctcctt cttttctgtac   1320
tctcgcctga ccgtggacaa gtctaggtgg caagagggca acgtgttctc ctgctctgtg   1380
ctgcacgagg ccctgcacaa tcactacacc cagaagtccc tgtctctgtc cctgggc      1437
```

<210> SEQ ID NO 17
<211> LENGTH: 454
<212> TYPE: PRT
<213> ORGANISM: Artificial Sequence
<220> FEATURE:
<223> OTHER INFORMATION: fusion protein (GI101C1)

<400> SEQUENCE: 17

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80
```

```
Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly
    450

<210> SEQ ID NO 18
<211> LENGTH: 1176
<212> TYPE: DNA
<213> ORGANISM: Artificial Sequence
<220> FEATURE:
<223> OTHER INFORMATION: nucleotiedes coding fusion protein (GI101C2)
```

<400> SEQUENCE: 18

```
atggatgcta tgctgagagg cctgtgttgc gtgctgctgc tgtgtggcgc tgtgttcgtg      60
tctccatctc acgccgctga gtctaagtac ggccctcctt gtcctccatg tcctgctcca     120
gaagctgctg gcggacccte tgtgttcctg tttcctccaa agcctaagga ccagctcatg     180
atctctcgga cccctgaagt gacctgcgtg gtggtggatg tgtctcaaga ggaccctgag     240
gtgcagttca attggtacgt ggacggcgtg gaagtgcaca acgccaagac caagcctaga     300
gaggaacagt tcaactccac ctacagagtg gtgtccgtgc tgaccgtgct gcaccaggat     360
tggctgaacg gcaaagagta caagtgcaag gtgtccaaca agggcctgcc ttccagcatc     420
gaaaagacca tctccaaggc taagggccag cctagggaac ccaggtttta caccctgcct     480
ccaagccaag aggaaatgac caagaaccag gtgtccctga cctgcctggt caagggcttc     540
taccctteeg acattgccgt ggaatgggag tccaatggcc agcctgagaa caactacaag     600
accacacctc ctgtgctgga ctccgacggc tccttctttc tgtactctcg cctgaccgtg     660
gacaagtcta ggtggcaaga gggcaacgtg ttctcctgct ctgtgctgca cgaggccctg     720
cacaatcact acacccagaa gtccctgtct ctgtctcttg gcggaggcgg aggatctgct     780
cctacctcca gctccaccaa gaaaacccag ctccagttgg agcatctgct gctggacctc     840
cagatgatcc tgaatggcat caacaattac aagaacccca agctgaccgc catgctgacc     900
gctaagttct acatgcccaa gaaggccacc gagctgaagc acctccagtg cctggaagag     960
gaactgaagc ccctggaaga agtgctgaat ctggcccagt ccaagaactt ccacctgagg    1020
cctagggacc tgatctccaa catcaacgtg atcgtgctgg aactgaaagg ctccgagaca    1080
accttcatgt gcgagtacgc cgacgagaca gccaccatcg tggaatttct gaaccggtgg    1140
atcaccttct gccagtccat catctccaca ctgacc                              1176
```

<210> SEQ ID NO 19
<211> LENGTH: 367
<212> TYPE: PRT
<213> ORGANISM: Artificial Sequence
<220> FEATURE:
<223> OTHER INFORMATION: fusion protein (GI101C2)

<400> SEQUENCE: 19

```
Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140
```

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Leu His Glu Ala Leu His Asn His Tyr Thr Gln Lys Ser Leu
    210                 215                 220

Ser Leu Ser Leu Gly Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Ala
            260                 265                 270

Met Leu Thr Ala Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Cys Gln Ser Ile Ile Ser Thr Leu Thr
        355                 360                 365

<210> SEQ ID NO 20
<211> LENGTH: 1434
<212> TYPE: DNA
<213> ORGANISM: Artificial Sequence
<220> FEATURE:
<223> OTHER INFORMATION: nucleotiedes coding fusion protein (mGI101C1)

<400> SEQUENCE: 20

```
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag     240 aacaggaccc tgtacgacaa caccacctac agcctgatca tcctgggcct cgtgctgagc     300
gatagaggca cctattcttg cgtggtgcag aagaaagagc ggggcaccta cgaagtgaag     360
cacctggctc tggtcaagct gtccatcaag gccgacttca gcacccctaa catcaccgag     420
tctggcaacc cttccgccga caccaagaga atcacctgtt cgcctctgg cggcttccct     480 aagcctcggt tctcttggct ggaaaacggc agagagctgc ccggcatcaa taccaccatt     540
tctcaggacc cagagtccga gctgtacacc atctccagcc agctcgactt aacaccacc     600 agaaaccaca ccatcaagtg cctgattaag tacggcgacg cccacgtgtc cgaggacttt     660
acttgggaga aacctcctga ggacctcct gactctggat ctggcggcgg aggttctggc     720
ggaggtggaa gcggaggcgg aggatctgct gagtctaagt atggccctcc ttgtcctcca     780
```

-continued

```
tgtcctgctc cagaagctgc tggcggaccc tctgtgttcc tgtttcctcc aaagcctaag    840
gaccagctca tgatctctcg gacccctgaa gtgacctgcg tggtggtgga tgtgtctcaa    900
gaggaccctg aggtgcagtt caattggtac gtggacggcg tggaagtgca caacgccaag    960
accaagccta gagaggaaca gttcaactcc acctatagag tggtgtccgt gctgaccgtg   1020
ctgcaccagg attggctgaa cggcaaagag tacaagtgca aggtgtccaa caagggcctg   1080
ccttccagca tcgaaaagac catcagcaag gctaagggcc agcctaggga accccaggtt   1140
tacaccctgc ctccaagcca gaggaaatg accaagaacc aggtgtccct gacctgcctg    1200
gtcaagggct ctacccttc cgacattgcc gtggaatggg agtccaatgg ccagcctgag    1260
aacaactaca agaccacacc tcctgtgctg gactccgacg gctccttctt tctgtactct   1320
cgcctgaccg tggacaagtc taggtggcaa gagggcaacg tgttctcctg ctctgtgctg   1380
cacgaggctc tgcacaacca ctacacccag aagtccctgt ctctgtccct gggc         1434
```

<210> SEQ ID NO 21
<211> LENGTH: 478
<212> TYPE: PRT
<213> ORGANISM: Artificial Sequence
<220> FEATURE:
<223> OTHER INFORMATION: fusion protein (mGI101C1)

<400> SEQUENCE: 21

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Ser Gly
225                 230                 235                 240

Gly Gly Gly Ser Gly Gly Gly Gly Ser Ala Glu Ser Lys Tyr Gly Pro
                245                 250                 255
```

```
Pro Cys Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly
465                 470                 475

<210> SEQ ID NO 22
<211> LENGTH: 133
<212> TYPE: PRT
<213> ORGANISM: Artificial Sequence
<220> FEATURE:
<223> OTHER INFORMATION: variants of IL-2 (3M, M45)

<400> SEQUENCE: 22

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Ala Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 23
<211> LENGTH: 133
<212> TYPE: PRT
<213> ORGANISM: Artificial Sequence
<220> FEATURE:
<223> OTHER INFORMATION: variants of IL-2 (3M, M61)

<400> SEQUENCE: 23

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Arg Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 24
<211> LENGTH: 133
<212> TYPE: PRT
<213> ORGANISM: Artificial Sequence
<220> FEATURE:
<223> OTHER INFORMATION: variants of IL-2 (3M, M72)

<400> SEQUENCE: 24

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 25
<211> LENGTH: 1851
<212> TYPE: DNA

<213> ORGANISM: Artificial Sequence
<220> FEATURE:
<223> OTHER INFORMATION: nucleotiedes coding fusion protein (GI102-M45)

<400> SEQUENCE: 25

```
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120
tgcggccaca acgtttcagt ggaagaactg gcccagacca ggatctactg cagaaagaa      180
aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga aggacgcctt caagcgcgag      360
cacctggctg aagtgacact gtccgtgaag gccgactttc ccacccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg      540
tctcaggacc ccgaaaccga gctgtacgct gtgtcctcca gctggactt caacatgacc      600
accaaccaca gcttcatgtg cctgattaag tacggccacc tgagagtgaa ccagaccttc      660
aactggaaca ccaccaagca agagcacttc cctgacaatg gatctggcgg cggaggttct      720
ggcggaggtg aagcggagg cggaggatct gctgagtcta agtatggccc tccttgtcct      780
ccatgtcctg ctccagaagc tgctggcgga ccctctgtgt tcctgttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc tagagagga acagttcaac tccacctaca gagtggtgtc cgtgctgacc     1020
gtgctgcacc aggattggct gaacggcaaa gagtacaagt gcaaggtgtc caacaagggc     1080
ctgccttcca gcatcgaaaa gaccatctcc aaggctaagg ccagcctag gaaccccag     1140
gtttacaccc tgcctccaag ccaagaggaa atgaccaaga accaggtgtc cctgacctgc     1200
ctggtcaagg gcttctaccc ttccgacatt gccgtggaat gggagtccaa tggccagcct     1260
gagaacaact acaagaccac acctcctgtg ctggactccg acggctcctt ctttctgtac     1320
tctcgcctga ccgtggacaa gtctagatgg caagagggca acgtgttctc ctgctctgtg     1380
ctgcacgagg ccctgcacaa tcactacacc cagaagtccc tgtctctgtc tcttggaggt     1440
ggtggcggtt ctgcccctac cagctcctct accaagaaaa cccagctcca gttggagcat     1500
ctgctgctgg acctccagat gattctgaac gggatcaaca actataagaa ccccaagctg     1560
accgccatgc tgaccgctaa gttcgccatg cccaagaagg ccaccgagct gaagcacctc     1620
cagtgcctgg aagaagaact gaagcccctg gaagaggtgc tgaatctggc ccagtccaag     1680
aacttccacc tgaggccacg ggacctgatc agcaacatca cgtgatcgt gctggaactg     1740
aagggctccg agacaacctt tatgtgcgag tacgccgacg agacagccac catcgtggaa     1800
tttctgaacc ggtggatcac cttctgccag agcatcatct ccacactgac c               1851
```

<210> SEQ ID NO 26
<211> LENGTH: 592
<212> TYPE: PRT
<213> ORGANISM: Artificial Sequence
<220> FEATURE:
<223> OTHER INFORMATION: fusion protein (GI102-M45)

<400> SEQUENCE: 26

Val Ile His Val Thr Lys Glu Val Lys Glu Val Ala Thr Leu Ser Cys

-continued

```
1               5                   10                  15
Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
                35                  40                  45

Ile Trp Pro Glu Tyr Lys Asn Arg Thr Ile Phe Asp Ile Thr Asn Asn
                50                  55                  60

Leu Ser Ile Val Ile Leu Ala Leu Arg Pro Ser Asp Glu Gly Thr Tyr
65                      70                  75                  80

Glu Cys Val Val Leu Lys Tyr Glu Lys Asp Ala Phe Lys Arg Glu His
                    85                  90                  95

Leu Ala Glu Val Thr Leu Ser Val Lys Ala Asp Phe Pro Thr Pro Ser
                100                 105                 110

Ile Ser Asp Phe Glu Ile Pro Thr Ser Asn Ile Arg Arg Ile Ile Cys
                115                 120                 125

Ser Thr Ser Gly Gly Phe Pro Glu Pro His Leu Ser Trp Leu Glu Asn
            130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                    165                 170                 175

Asn His Ser Phe Met Cys Leu Ile Lys Tyr Gly His Leu Arg Val Asn
                180                 185                 190

Gln Thr Phe Asn Trp Asn Thr Thr Lys Gln Glu His Phe Pro Asp Asn
                195                 200                 205

Gly Ser Gly Gly Gly Ser Gly Gly Gly Ser Gly Gly Gly Gly
210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                    245                 250                 255

Asp Gln Leu Met Ile Ser Arg Thr Pro Glu Val Thr Cys Val Val Val
                260                 265                 270

Asp Val Ser Gln Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
                340                 345                 350

Glu Pro Gln Val Tyr Thr Leu Pro Pro Ser Gln Glu Glu Met Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Arg Leu Thr Val Asp Lys Ser Arg Trp Gln Glu Gly Asn Val Phe Ser
                420                 425                 430
```

```
Cys Ser Val Leu His Glu Ala Leu His Asn His Tyr Thr Gln Lys Ser
            435                 440                 445
Leu Ser Leu Ser Leu Gly Gly Gly Gly Ser Ala Pro Thr Ser Ser
450                 455                 460
Ser Thr Lys Lys Thr Gln Leu Gln Leu Glu His Leu Leu Leu Asp Leu
465                 470                 475                 480
Gln Met Ile Leu Asn Gly Ile Asn Asn Tyr Lys Asn Pro Lys Leu Thr
                485                 490                 495
Ala Met Leu Thr Ala Lys Phe Ala Met Pro Lys Lys Ala Thr Glu Leu
            500                 505                 510
Lys His Leu Gln Cys Leu Glu Glu Glu Leu Lys Pro Leu Glu Glu Val
            515                 520                 525
Leu Asn Leu Ala Gln Ser Lys Asn Phe His Leu Arg Pro Arg Asp Leu
        530                 535                 540
Ile Ser Asn Ile Asn Val Ile Val Leu Glu Leu Lys Gly Ser Glu Thr
545                 550                 555                 560
Thr Phe Met Cys Glu Tyr Ala Asp Glu Thr Ala Thr Ile Val Glu Phe
                565                 570                 575
Leu Asn Arg Trp Ile Thr Phe Cys Gln Ser Ile Ile Ser Thr Leu Thr
            580                 585                 590
```

<210> SEQ ID NO 27
<211> LENGTH: 1851
<212> TYPE: DNA
<213> ORGANISM: Artificial Sequence
<220> FEATURE:
<223> OTHER INFORMATION: nucleotiedes coding fusion protein (GI102-M61)

<400> SEQUENCE: 27

```
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc      120
tgcggccaca acgtttcagt ggaagaactg gcccagacca ggatctactg gcagaaagaa     180
aagaaaatgg tgctgaccat gatgtccggc gacatgaaca tctggcctga gtacaagaac     240
cggaccatct tcgacatcac caacaacctg tccatcgtga ttctggccct gaggccttct     300
gatgagggca cctatgagtg cgtggtgctg aagtacgaga aggacgcctt caagcgcgag     360
cacctggctg aagtgacact gtccgtgaag gccgactttc ccacaccttc catctccgac     420
ttcgagatcc ctacctccaa catccggcgg atcatctgtt ctacctctgg cggctttcct     480
gagcctcacc tgtcttggct ggaaaacggc gaggaactga cgccatcaa caccaccgtg     540
tctcaggacc ccgaaaccga gctgtacgct gtgtcctcca gctggactt caacatgacc     600
accaaccaca gcttcatgtg cctgattaag tacggccacc tgagagtgaa ccagaccttc     660
aactggaaca ccaccaagca agagcacttc cctgacaatg gatctggcgg cggaggttct     720
ggcggaggtg aagcggagg cggaggatct gctgagtcta gtatggcccc tcttgtcct     780
ccatgtcctg ctccagaagc tgctggcgga ccctctgtgt tcctgttcc tccaaagcct     840
aaggaccagc tcatgatctc tcggacaccc gaagtgacct gcgtggtggt ggatgtgtct     900
caagaggacc ctgaggtgca gttcaattgg tacgtggacg gcgtggaagt gcacaacgcc     960
aagaccaagc ctagagagga acagttcaac tccacctaca gtggtgtgtc cgtgctgacc    1020
gtgctgcacc aggattggct gaacggcaaa gagtacaagt gcaaggtgtc caacaagggc    1080
ctgccttcca gcatcgaaaa gaccatctcc aaggctaagg gccagcctag ggaaccccag    1140
```

```
gtttacaccc tgcctccaag ccaagaggaa atgaccaaga accaggtgtc cctgacctgc    1200
ctggtcaagg gcttctaccc ttccgacatt gccgtggaat gggagtccaa tggccagcct    1260
gagaacaact acaagaccac acctcctgtg ctggactccg acggctcctt ctttctgtac    1320
tctcgcctga ccgtggacaa gtctagatgg caagagggca acgtgttctc ctgctctgtg    1380
ctgcacgagg ccctgcacaa tcactacacc cagaagtccc tgtctctgtc tcttggaggt    1440
ggtggcggtt ctgcccctac cagctcctct accaagaaaa cccagctcca gttggagcat    1500
ctgctgctgg acctccagat gattctgaac gggatcaaca actataagaa ccccaagctg    1560
accgccatgc tgaccgctaa gttctacatg cccaagaagg ccaccgagct gaagcacctc    1620
cagtgcctgg aaagggaact gaagcccctg aagaggtgc tgaatctggc ccagtccaag    1680
aacttccacc tgaggccacg ggacctgatc agcaacatca cgtgatcgt gctggaactg    1740 aagggctccg agacaacctt tatgtgcgag tacgccgacg agacagccac catcgtggaa    1800
tttctgaacc ggtggatcac cttctgccag agcatcatct ccacactgac c             1851
```

<210> SEQ ID NO 28
<211> LENGTH: 592
<212> TYPE: PRT
<213> ORGANISM: Artificial Sequence
<220> FEATURE:
<223> OTHER INFORMATION: fusion protein (GI102-M61)

<400> SEQUENCE: 28

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Ser Gly Gly Gly Ser Gly Gly Gly
    210                 215                 220

Ser Ala Glu Ser Lys Tyr Gly Pro Pro Cys Pro Pro Cys Pro Ala Pro
225                 230                 235                 240
```

```
Glu Ala Ala Gly Gly Pro Ser Val Phe Leu Phe Pro Lys Pro Lys
                    245                 250                 255

Asp Gln Leu Met Ile Ser Arg Thr Pro Glu Val Thr Cys Val Val
                260                 265                 270

Asp Val Ser Gln Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Gln Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Ser Ala Pro Thr Ser Ser
450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Arg Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590

<210> SEQ ID NO 29
<211> LENGTH: 1857
<212> TYPE: DNA
<213> ORGANISM: Artificial Sequence
<220> FEATURE:
<223> OTHER INFORMATION: nucleotiedes coding fusion protein (GI102-M72)

<400> SEQUENCE: 29
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc     120
```

```
tgcggccaca acgtttcagt ggaagaactg gcccagacca ggatctactg gcagaaagaa      180
aagaaaatgg tgctgaccat gatgtccggc gacatgaaca tctggcctga gtacaagaac      240
cggaccatct tcgacatcac caacaacctg tccatcgtga ttctggccct gaggccttct      300
gatgagggca cctatgagtg cgtggtgctg aagtacgaga ggacgccttc aagcgcgag       360 cacctggctg aagtgacact gtccgtgaag gccgactttc ccacaccttc catctccgac      420
ttcgagatcc ctacctccaa catccggcgg atcatctgtt ctacctctgg cggctttcct      480
gagcctcacc tgtcttggct ggaaaacggc gaggaactga cgccatcaa caccaccgtg       540 tctcaggacc ccgaaaccga gctgtacgct gtgtcctcca gctggacttc aacatgacc       600 accaaccaca gcttcatgtg cctgattaag tacgccacc tgagagtgaa ccagaccttc       660
aactggaaca ccaccaagca agagcacttc cctgacaatg gatctggcgg cggaggttct      720
ggcggaggtg aagcggagg cggaggatct gctgagtcta agtatggccc tccttgtcct       780
ccatgtcctg ctccagaagc tgctggcgga ccctctgtgt tcctgtttcc tccaaagcct      840
aaggaccagc tcatgatctc tcggacaccc gaagtgacct gcgtggtggt ggatgtgtct      900
caagaggacc ctgaggtgca gttcaattgg tacgtggacg gcgtggaagt gcacaacgcc      960
aagaccaagc ctagagagga acagttcaac tccacctaca gagtggtgtc cgtgctgacc     1020
gtgctgcacc aggattggct gaacggcaaa gagtacaagt gcaaggtgtc caacaagggc     1080
ctgccttcca gcatcgaaaa gaccatctcc aaggctaagg gccagcctag ggaaccccag     1140
gtttacaccc tgcctccaag ccaagaggaa atgaccaaga accaggtgtc cctgacctgc     1200
ctggtcaagg gcttctaccc ttccgacatt gccgtggaat gggagtccaa tggccagcct     1260
gagaacaact acaagaccac acctcctgtg ctggactccg acggctcctt ctttctgtac     1320
tctcgcctga ccgtggacaa gtctagatgg caagagggca cgtgttctc ctgctctgtg      1380 ctgcacgagg ccctgcacaa tcactacacc cagaagtccc tgtctctgtc tcttggaggt     1440
ggtggcggtt ctgcccctac cagctcctct accaagaaaa cccagctcca gttggagcat     1500
ctgctgctgg acctcagat gattctgaac gggatcaaca actataagaa ccccaagctg      1560
accgccatgc tgaccgctaa gttctacatg cccaagaagg ccaccgagct gaagcacctc     1620
cagtgcctgg aagaagaact gaagcccctg gaagaggtgc tgaatggggc ccagtccaag     1680
aacttccacc tgaggccacg ggacctgatc agcaacatca cgtgatcgt gctggaactg      1740 aagggctccg agacaacctt tatgtgcgag tacgccgacg agacagccac catcgtggaa     1800
tttctgaacc ggtggatcac cttctgccag agcatcatct ccacactgac ctgatga        1857
```

<210> SEQ ID NO 30
<211> LENGTH: 592
<212> TYPE: PRT
<213> ORGANISM: Artificial Sequence
<220> FEATURE:
<223> OTHER INFORMATION: fusion protein (GI102-M72)

<400> SEQUENCE: 30

```
Val Ile His Val Thr Lys Glu Val Lys Glu Val Ala Thr Leu Ser Cys
1               5                  10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
```

```
            50                  55                  60
Leu Ser Ile Val Ile Leu Ala Leu Arg Pro Ser Asp Glu Gly Thr Tyr
 65                  70                  75                  80

Glu Cys Val Val Leu Lys Tyr Glu Lys Asp Ala Phe Lys Arg Glu His
                     85                  90                  95

Leu Ala Glu Val Thr Leu Ser Val Lys Ala Asp Phe Pro Thr Pro Ser
                    100                 105                 110

Ile Ser Asp Phe Glu Ile Pro Thr Ser Asn Ile Arg Arg Ile Ile Cys
                    115                 120                 125

Ser Thr Ser Gly Gly Phe Pro Glu Pro His Leu Ser Trp Leu Glu Asn
            130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                    165                 170                 175

Asn His Ser Phe Met Cys Leu Ile Lys Tyr Gly His Leu Arg Val Asn
                180                 185                 190

Gln Thr Phe Asn Trp Asn Thr Thr Lys Gln Glu His Phe Pro Asp Asn
                195                 200                 205

Gly Ser Gly Gly Gly Ser Gly Gly Gly Ser Gly Gly Gly Gly
        210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
                260                 265                 270

Asp Val Ser Gln Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Arg Leu Thr Val Asp Lys Ser Arg Trp Gln Glu Gly Asn Val Phe Ser
                420                 425                 430

Cys Ser Val Leu His Glu Ala Leu His Asn His Tyr Thr Gln Lys Ser
            435                 440                 445

Leu Ser Leu Ser Leu Gly Gly Gly Gly Ser Ala Pro Thr Ser Ser
            450                 455                 460

Ser Thr Lys Lys Thr Gln Leu Gln Leu Glu His Leu Leu Leu Asp Leu
465                 470                 475                 480
```

```
Gln Met Ile Leu Asn Gly Ile Asn Asn Tyr Lys Asn Pro Lys Leu Thr
                485                 490                 495
Ala Met Leu Thr Ala Lys Phe Tyr Met Pro Lys Lys Ala Thr Glu Leu
            500                 505                 510
Lys His Leu Gln Cys Leu Glu Glu Glu Leu Lys Pro Leu Glu Glu Val
        515                 520                 525
Leu Asn Gly Ala Gln Ser Lys Asn Phe His Leu Arg Pro Arg Asp Leu
    530                 535                 540
Ile Ser Asn Ile Asn Val Ile Val Leu Glu Leu Lys Gly Ser Glu Thr
545                 550                 555                 560
Thr Phe Met Cys Glu Tyr Ala Asp Glu Thr Ala Thr Ile Val Glu Phe
                565                 570                 575
Leu Asn Arg Trp Ile Thr Phe Cys Gln Ser Ile Ile Ser Thr Leu Thr
                580                 585                 590

<210> SEQ ID NO 31
<211> LENGTH: 1851
<212> TYPE: DNA
<213> ORGANISM: Artificial Sequence
<220> FEATURE:
<223> OTHER INFORMATION: nucleotiedes coding fusion protein (GI101w)

<400> SEQUENCE: 31
atggatgcta tgctgagagg cctgtgttgc gtgctgctgc tgtgtggcgc tgtgttcgtg      60
tctccttctc acgctgtgat ccacgtgacc aaagaagtga agaggtcgc cacactgtcc     120 tgcggccaca acgtttcagt ggaagaactg gcccagacca ggatctactg cagaaagaa     180 aagaaaatgg tgctgaccat gatgtccggc gacatgaaca tctggcctga gtacaagaac     240
cggaccatct tcgacatcac caacaacctg tccatcgtga ttctggccct gaggccttct     300
gatgagggca cctatgagtg cgtggtgctg aagtacgaga ggacgcctt caagcgcgag     360 cacctggctg aagtgacact gtccgtgaag gccgactttc ccacaccttc catctccgac     420
ttcgagatcc ctacctccaa catccggcgg atcatctgtt ctacctctgg cggctttcct     480
gagcctcacc tgtcttggct ggaaaacggc gaggaactga acgccatcaa caccaccgtg     540
tctcaggacc ccgaaaccga gctgtacgct gtgtcctcca gctggactt caacatgacc     600 accaaccaca gcttcatgtg cctgattaag tacggccacc tgagagtgaa ccagaccttc     660
aactggaaca ccaccaagca gagcacttc cctgacaatg gatctggcgg cggaggttct     720
ggcggaggtg gaagcggagg cggaggatct gctgagtcta agtatggccc tccttgtcct     780
ccatgtcctg ctccagaagc tgctggcgga ccctctgtgt tcctgtttcc tccaaagcct     840
aaggaccagc tcatgatctc tcggacaccc gaagtgacct gcgtggtggt ggatgtgtct     900
caagaggacc ctgaggtgca gttcaattgg tacgtggacg gcgtggaagt gcacaacgcc     960
aagaccaagc ctagagagga acagttcaac tccacctaca gagtggtgtc cgtgctgacc    1020
gtgctgcacc aggattggct gaacggcaaa gagtacaagt gcaaggtgtc caacaagggc    1080
ctgccttcca gcatcgaaaa gaccatctcc aaggctaagg ccagcctag ggaaccccag    1140 gtttacaccc tgcctccaag ccaagaggaa atgaccaaga accaggtgtc cctgacctgc    1200
ctggtcaagg gcttctaccc ttccgacatt gccgtggaat gggagtccaa tggccagcct    1260
gagaacaact acaagaccac acctcctgtg ctggactccg acggctcctt ctttctgtac    1320
tctcgcctga ccgtggacaa gtctagatgg caagagggca acgtgttctc ctgctctgtg    1380
ctgcacgagg ccctgcacaa tcactacacc cagaagtccc tgtctctgtc tcttggaggt    1440
```

-continued

```
ggtggcggtt ctgcccctac cagctcctct accaagaaaa cccagctcca gttggagcat    1500
ctgctgctgg acctccagat gattctgaac gggatcaaca actataagaa ccccaagctg    1560
acccgcatgc tgacctttaa gttctacatg cccaagaagg ccaccgagct gaagcacctc    1620
cagtgcctgg aagaagaact gaagcccctg gaagaggtgc tgaatctggc ccagtccaag    1680
aacttccacc tgaggccacg ggacctgatc agcaacatca acgtgatcgt gctggaactg    1740
aagggctccg agacaacctt tatgtgcgag tacgccgacg agacagccac catcgtggaa    1800
tttctgaacc ggtggatcac cttctgccag agcatcatct ccacactgac c             1851
```

<210> SEQ ID NO 32
<211> LENGTH: 592
<212> TYPE: PRT
<213> ORGANISM: Artificial Sequence
<220> FEATURE:
<223> OTHER INFORMATION: fusion protein (GI101w)

<400> SEQUENCE: 32

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285
```

Gly Val Glu Val His Asn Ala Lys Thr Lys Pro Arg Glu Glu Gln Phe
    290                 295                 300

Asn Ser Thr Tyr Arg Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
                340                 345                 350

Glu Pro Gln Val Tyr Thr Leu Pro Pro Ser Gln Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
                420                 425                 430

Cys Ser Val Leu His Glu Ala Leu His Asn His Tyr Thr Gln Lys Ser
            435                 440                 445

Leu Ser Leu Ser Leu Gly Gly Gly Gly Ser Ala Pro Thr Ser Ser
450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
                500                 505                 510

Lys His Leu Gln Cys Leu Glu Glu Glu Leu Lys Pro Leu Glu Glu Val
            515                 520                 525

Leu Asn Leu Ala Gln Ser Lys Asn Phe His Leu Arg Pro Arg Asp Leu
530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
                580                 585                 590

<210> SEQ ID NO 33
<211> LENGTH: 1848
<212> TYPE: DNA
<213> ORGANISM: Artificial Sequence
<220> FEATURE:
<223> OTHER INFORMATION: nucleotiedes coding fusion protein (mGI102-M61)

<400> SEQUENCE: 33
atggatgcta tgctgagagg cctgtgttgc gtgctgctgc tgtgtggcgc tgtgttcgtg      60
tctccttctc acgctgtgga cgagcagctc tccaagtccg tgaaggataa ggtcctgctg     120
ccttgccggt acaactctcc tcacgaggac gagtctgagg accggatcta ctggcagaaa     180
cacgacaagg tggtgctgtc cgtgatcgcc ggaaagctga agtgtggcc tgagtacaag      240 aacaggaccc tgtacgacaa caccacctac agcctgatca tcctgggcct cgtgctgagc     300
gatagaggca cctattcttg cgtggtgcag aagaaagagc ggggcaccta cgaagtgaag     360

```
cacctggctc tggtcaagct gtccatcaag gccgacttca gcaccccctaa catcaccgag    420 tctggcaacc cttccgccga caccaagaga atcacctgtt tcgcctctgg cggcttccct    480
aagcctcggt tctcttggct ggaaaacggc agagagctgc ccggcatcaa taccaccatt    540
tctcaggacc cagagtccga gctgtacacc atctccagcc agctcgactt taacaccacc    600
agaaaccaca ccatcaagtg cctgattaag tacggcgacg cccacgtgtc cgaggacttt    660
acttgggaga aacctcctga ggaccctcct gactctggat ctggcggcgg aggttctggc    720
ggaggtggaa gcggaggcgg aggatctgct gagtctaagt atggccctcc ttgtcctcca    780
tgtcctgctc cagaagctgc tggcggaccc tctgtgttcc tgtttcctcc aaagcctaag    840
gaccagctca tgatctctcg gacccctgaa gtgacctgcg tggtggtgga tgtgtctcaa    900
gaggaccctg aggtgcagtt caattggtac gtggacggcg tggaagtgca caacgccaag    960
accaagccta gagaggaaca gttcaactcc acctatagag tggtgtccgt gctgaccgtg   1020
ctgcaccagg attggctgaa cggcaaagag tacaagtgca aggtgtccaa caagggcctg   1080
ccttccagca tcgaaaagac catcagcaag gctaagggcc agcctaggga accccaggtt   1140
tacaccctgc ctccaagcca agaggaaatg accaagaacc aggtgtccct gacctgcctg   1200
gtcaagggct ctaccccttc cgacattgcc gtggaatggg agtccaatgg ccagcctgag   1260
aacaactaca agaccacacc tcctgtgctg gactccgacg gctccttctt tctgtactct   1320
cgcctgaccg tggacaagtc taggtggcaa gagggcaacg tgttctcctg ctctgtgctg   1380
cacgaggctc tgcacaacca ctacacccag aagtccctgt ctctgtctct ggaggtggt    1440 ggcggttctg cccctacctc cagctctacc aagaaaaccc agctccagtt ggagcatctg   1500
ctgctggacc tccagatgat cctgaatggc atcaacaatt acaagaaccc caagctgacc   1560
gccatgctga ccgctaagtt ctacatgccc aagaaggcca ccgagctgaa gcacttgcag   1620
tgcctggaaa gggaactgaa gcccctggaa gaagtgctga atctggccca gtccaagaac   1680
ttccacctga ggcctaggga cctgatctcc aacatcaacg tgatcgtgct ggaactgaaa   1740
ggctccgaga caaccttcat gtgcgagtac gccgacgaga cagccaccat cgtggaattt   1800
ctgaaccggt ggatcacctt ctgccagagc atcatctcca cactgacc              1848
```

<210> SEQ ID NO 34
<211> LENGTH: 616
<212> TYPE: PRT
<213> ORGANISM: Artificial Sequence
<220> FEATURE:
<223> OTHER INFORMATION: fusion protein (mGI102-M61)

<400> SEQUENCE: 34

```
Met Asp Ala Met Leu Arg Gly Leu Cys Cys Val Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
```

-continued

```
                100                 105                 110
Glu Arg Gly Thr Tyr Glu Val Lys His Leu Ala Leu Val Lys Leu Ser
            115                 120                 125

Ile Lys Ala Asp Phe Ser Thr Pro Asn Ile Thr Glu Ser Gly Asn Pro
130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
            165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
            195                 200                 205

Ile Lys Tyr Gly Asp Ala His Val Ser Glu Asp Phe Thr Trp Glu Lys
            210                 215                 220

Pro Pro Glu Asp Pro Pro Asp Ser Gly Ser Gly Gly Gly Ser Gly
225                 230                 235                 240

Gly Gly Gly Ser Gly Gly Gly Ser Ala Glu Ser Lys Tyr Gly Pro
            245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
            275                 280                 285

Pro Glu Val Thr Cys Val Val Val Asp Val Ser Gln Glu Asp Pro Glu
290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
            355                 360                 365

Ser Lys Ala Lys Gly Gln Pro Arg Glu Pro Gln Val Tyr Thr Leu Pro
            370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
            435                 440                 445

Trp Gln Glu Gly Asn Val Phe Ser Cys Ser Val Leu His Glu Ala Leu
            450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
            485                 490                 495

Leu Glu His Leu Leu Leu Asp Leu Gln Met Ile Leu Asn Gly Ile Asn
            500                 505                 510

Asn Tyr Lys Asn Pro Lys Leu Thr Ala Met Leu Thr Ala Lys Phe Tyr
            515                 520                 525
```

```
Met Pro Lys Lys Ala Thr Glu Leu Lys His Leu Gln Cys Leu Glu Arg
    530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
        595                 600                 605

Gln Ser Ile Ile Ser Thr Leu Thr
        610                 615

<210> SEQ ID NO 35
<211> LENGTH: 153
<212> TYPE: PRT
<213> ORGANISM: Artificial Sequence
<220> FEATURE:
<223> OTHER INFORMATION: wild type hIL-2

<400> SEQUENCE: 35

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 36
<211> LENGTH: 158
<212> TYPE: PRT
<213> ORGANISM: Artificial Sequence
<220> FEATURE:
<223> OTHER INFORMATION: IL-2 with signal sequence

<400> SEQUENCE: 36

Met Asp Ala Met Leu Arg Gly Leu Cys Cys Val Leu Leu Leu Cys Gly
1               5                   10                  15

Ala Val Phe Val Ser Pro Ser His Ala Ala Pro Thr Ser Ser Ser Thr
            20                  25                  30

Lys Lys Thr Gln Leu Gln Leu Glu His Leu Leu Leu Asp Leu Gln Met
        35                  40                  45

Ile Leu Asn Gly Ile Asn Asn Tyr Lys Asn Pro Lys Leu Thr Arg Met
```

```
            50                   55                  60
Leu Thr Phe Lys Phe Tyr Met Pro Lys Ala Thr Glu Leu Lys His
 65                  70                  75                  80

Leu Gln Cys Leu Glu Glu Glu Leu Lys Pro Leu Glu Glu Val Leu Asn
                 85                  90                  95

Leu Ala Gln Ser Lys Asn Phe His Leu Arg Pro Arg Asp Leu Ile Ser
                100                 105                 110

Asn Ile Asn Val Ile Val Leu Glu Leu Lys Gly Ser Glu Thr Thr Phe
            115                 120                 125

Met Cys Glu Tyr Ala Asp Glu Thr Ala Thr Ile Val Glu Phe Leu Asn
130                 135                 140

Arg Trp Ile Thr Phe Cys Gln Ser Ile Ile Ser Thr Leu Thr
145                 150                 155

<210> SEQ ID NO 37
<211> LENGTH: 474
<212> TYPE: DNA
<213> ORGANISM: Artificial Sequence
<220> FEATURE:
<223> OTHER INFORMATION: nucleotide sequence coding IL-2 with signal
      sequence

<400> SEQUENCE: 37
atggatgcta tgctgagagg cctgtgttgc gtgctgctgc tgtgtggcgc tgtgttcgtg     60
tctccttctc acgctgcccc taccagctcc tctaccaaga aaacccagct ccagttggag    120
catctgctgc tggacctcca gatgattctg aacgggatca caactataa gaaccccaag    180 ctgacccgca tgctgacctt taagttctac atgcccaaga aggccaccga gctgaagcac    240
ctccagtgcc tggaagaaga actgaagccc ctggaagagg tgctgaatct ggcccagtcc    300
aagaacttcc acctgaggcc acgggacctg atcagcaaca tcaacgtgat cgtgctggaa    360
ctgaagggct ccgagacaac ctttatgtgc gagtacgccg acgagacagc caccatcgtg    420
gaatttctga accggtggat caccttctgc cagagcatca tctccacact gacc           474

<210> SEQ ID NO 38
<211> LENGTH: 591
<212> TYPE: PRT
<213> ORGANISM: Artificial Sequence
<220> FEATURE:
<223> OTHER INFORMATION: mGI-101

<400> SEQUENCE: 38

Val Asp Glu Gln Leu Ser Lys Ser Val Lys Asp Lys Val Leu Leu Pro
  1               5                  10                  15

Cys Arg Tyr Asn Ser Pro His Glu Asp Glu Ser Glu Asp Arg Ile Tyr
                 20                  25                  30

Trp Gln Lys His Asp Lys Val Val Leu Ser Val Ile Ala Gly Lys Leu
             35                  40                  45

Lys Val Trp Pro Glu Tyr Lys Asn Arg Thr Leu Tyr Asp Asn Thr Thr
         50                  55                  60

Tyr Ser Leu Ile Ile Leu Gly Leu Val Leu Ser Asp Arg Gly Thr Tyr
 65                  70                  75                  80

Ser Cys Val Val Gln Lys Lys Glu Arg Gly Thr Tyr Glu Val Lys His
                 85                  90                  95

Leu Ala Leu Val Lys Leu Ser Ile Lys Ala Asp Phe Ser Thr Pro Asn
                100                 105                 110

Ile Thr Glu Ser Gly Asn Pro Ser Ala Asp Thr Lys Arg Ile Thr Cys
```

```
            115                 120                 125
Phe Ala Ser Gly Gly Phe Pro Lys Pro Arg Phe Ser Trp Leu Glu Asn
    130                 135                 140
Gly Arg Glu Leu Pro Gly Ile Asn Thr Thr Ile Ser Gln Asp Pro Glu
145                 150                 155                 160
Ser Glu Leu Tyr Thr Ile Ser Ser Gln Leu Asp Phe Asn Thr Thr Arg
                165                 170                 175
Asn His Thr Ile Lys Cys Leu Ile Lys Tyr Gly Asp Ala His Val Ser
            180                 185                 190
Glu Asp Phe Thr Trp Glu Lys Pro Pro Glu Asp Pro Pro Asp Ser Gly
        195                 200                 205
Ser Gly Gly Gly Ser Gly Gly Gly Ser Gly Gly Gly Ser
    210                 215                 220
Ala Glu Ser Lys Tyr Gly Pro Pro Cys Pro Pro Cys Pro Ala Pro Glu
225                 230                 235                 240
Ala Ala Gly Gly Pro Ser Val Phe Leu Phe Pro Pro Lys Pro Lys Asp
                245                 250                 255
Gln Leu Met Ile Ser Arg Thr Pro Glu Val Thr Cys Val Val Val Asp
            260                 265                 270
Val Ser Gln Glu Asp Pro Glu Val Gln Phe Asn Trp Tyr Val Asp Gly
        275                 280                 285
Val Glu Val His Asn Ala Lys Thr Lys Pro Arg Glu Glu Gln Phe Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Gly Leu Pro
                325                 330                 335
Ser Ser Ile Glu Lys Thr Ile Ser Lys Ala Lys Gly Gln Pro Arg Glu
            340                 345                 350
Pro Gln Val Tyr Thr Leu Pro Pro Ser Gln Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Arg
                405                 410                 415
Leu Thr Val Asp Lys Ser Arg Trp Gln Glu Gly Asn Val Phe Ser Cys
            420                 425                 430
Ser Val Leu His Glu Ala Leu His Asn His Tyr Thr Gln Lys Ser Leu
        435                 440                 445
Ser Leu Ser Leu Gly Gly Gly Gly Ser Ala Pro Thr Ser Ser Ser
    450                 455                 460
Thr Lys Lys Thr Gln Leu Gln Leu Glu His Leu Leu Leu Asp Leu Gln
465                 470                 475                 480
Met Ile Leu Asn Gly Ile Asn Asn Tyr Lys Asn Pro Lys Leu Thr Ala
                485                 490                 495
Met Leu Thr Ala Lys Phe Tyr Met Pro Lys Lys Ala Thr Glu Leu Lys
            500                 505                 510
His Leu Gln Cys Leu Glu Glu Glu Leu Lys Pro Leu Glu Glu Val Leu
        515                 520                 525
Asn Leu Ala Gln Ser Lys Asn Phe His Leu Arg Pro Arg Asp Leu Ile
    530                 535                 540
```

```
Ser Asn Ile Asn Val Ile Val Leu Glu Leu Lys Gly Ser Glu Thr Thr
545                 550                 555                 560

Phe Met Cys Glu Tyr Ala Asp Glu Thr Ala Thr Ile Val Glu Phe Leu
                565                 570                 575

Asn Arg Trp Ile Thr Phe Cys Gln Ser Ile Ile Ser Thr Leu Thr
                580                 585                 590

<210> SEQ ID NO 39
<211> LENGTH: 120
<212> TYPE: PRT
<213> ORGANISM: Artificial Sequence
<220> FEATURE:
<223> OTHER INFORMATION: TIGIT ECD

<400> SEQUENCE: 39

Met Met Thr Gly Thr Ile Glu Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
        50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
                100                 105                 110

His Gly Ala Arg Phe Gln Ile Pro
                115                 120
```